(12) United States Patent
Cain et al.

(10) Patent No.: US 6,239,143 B1
(45) Date of Patent: May 29, 2001

(54) 5-HT$_7$ RECEPTOR ANTAGONISTS

(75) Inventors: Gary Avonn Cain; John Francis McElroy, both of Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/344,916

(22) Filed: Jun. 25, 1999

Related U.S. Application Data

(60) Provisional application No. 60/091,254, filed on Jun. 30, 1998.

(51) Int. Cl.$^7$ .................. C07D 217/04; A61K 31/47
(52) U.S. Cl. .................. 514/307; 514/290; 546/101; 546/148; 546/149
(58) Field of Search .................. 546/139, 101, 546/148, 149; 514/307, 290

(56) References Cited

U.S. PATENT DOCUMENTS

| | | | |
|---|---|---|---|
| 4,127,580 | 11/1978 | Braye | 546/114 |
| 5,250,540 | 10/1993 | Arlt et al. | 514/302 |
| 5,294,621 | 3/1994 | Russell | 514/301 |

FOREIGN PATENT DOCUMENTS

| | | |
|---|---|---|
| 868365 | 4/1971 | (CA) . |
| 2628045a1 | 6/1976 | (DK) . |
| 0026749A1 | 6/1980 | (EP) . |
| 0519291A1 | 6/1992 | (EP) . |
| WO93/16050 | 8/1993 | (WO) . |
| WO 97/29097 | 1/1997 | (WO) . |
| WO 97/48681 | 6/1997 | (WO) . |
| WO 97/49695 | 6/1997 | (WO) . |

OTHER PUBLICATIONS

Chemical Abstracts, vol. 79, No. 5, Aug. 6, 1973 (CP002118127).

Chemical Abstracts, vol. 92, No. 5, Feb. 4, 1980 (XP002118128).

Forbes, Ian T.; Dabbs, Steven; et al., (R)–3,N–Dimethyl–N–[1–methyl–3–(methyl–piperdin–1–yl)propyl]benzene-sulfonamide: The First Selective 5–HT7 Receptor Antagonist, *Journal of Medicinal Chemistry*, 41, 655–657, Feb. 26, 1998.

Roth, Bryan L.; Craigo, Sean C.; et al., Binding of Typical and Atypical Antipsychotic Agents to 5–Hydroxytryptamine–6 and 5–Hydroxytryptamine–7 Receptors, *Journal of Pharmacology and Experimental Thera.*, 268, 1403–1410, 1997.

Leung, E.; Walsh, L.K.M. et al., Characterization of putative 5–ht7 receptors mediating direct relaxation in Cynomolgus monkey isolated jugular vein, *British Journal of Pharmacology*, 117, 926–930, 1996.

Heidmann, Doris E.A.; Metcalf, Mark; et al., Four 5–Hydroxytryptamine7 (5–HT7) Receptor Isoforms in Human and Rat Produced by Alternative Splicing: Species Differences Due to Altered Intron–Exon Organization, *Journal of Neurochemistry*, 68, 1372–1381, 1997.

To, Z.P.; Bonhaus, D.W.; et al., Characterization and distribution of putative 5–ht7 receptors in guinea–pig brain, *Journal of Pharmacology*, 115, 107–116, 1995.

Cushing, Daniel J.; Zgombick, John M.; et al., LY215840, a High–Affinity 5–HT7 Receptor Ligand, Blocks Serotonin–Induced Relaxation in Canine Coronary Artery, *Journal of Pharmacology and Experimental Thera.*, 277, 1560–1566, 1996.

Schwartz, William J. M.D., A Clinician's Primer on the Circadian Clock: Its Localization, Function and Resetting, *Advances in Internal Medicine*, 38, 81–106, 1993.

Primary Examiner—Zinna Northington Davis

(57) ABSTRACT

The present invention relates to compounds having pharmacological activity toward the 5-HT$_7$ receptor. Pharmaceutical compositions and methods for their use in the treatment of CNS disorders are described.

15 Claims, No Drawings

5-HT7 RECEPTOR ANTAGONISTS

This application claims the benefit of U.S. Provisional Application Ser. No. 60/091,254 filed on Jun. 30, 1998.

FIELD OF THE INVENTION

The present invention relates to compounds having pharmacological activity toward the 5-HT$_7$ receptor. Pharmaceutical compositions and methods for their use in the treatment of CNS disorders are described.

BACKGROUND OF THE INVENTION

The 5-HT$_7$ receptor is the most recent addition to the burgeoning family of 5-HT receptors. 5-HT$_7$ receptors have been cloned from rat, mouse, guinea pig, and human cDNA and exhibit a high degree of interspecies homology, (approximately 95%) but a low sequence homology with other 5-HT receptors (<40%). The pharmacological profile of this receptor is unique yet consistent across species. Thus, high 5-HT$_7$ receptor affinity is observed from 5-CT, 5-HT, 5-MeOT, and methiothepin, moderate affinity for 8-OHDPAT, clozapine, and ritanserin, and low affinity for pindolol, sumatriptan, and buspirone. Recent data have demonstrated the existence of four 5-HT$_7$ splice variants in humans and three in rat (Heidmann, et al., *J. Neurochem.*, 1997, 68, 1372–1381). Preliminary pharmacological comparison of the long (5-HT$_{7a}$) and short (5-HT$_{7b}$) forms of the receptor have revealed no substantial differences in receptor binding affinity (Jasper et al., *J. Pharmocol.*, 1997, 120, 298). 5-HT$_7$ receptors are positively coupled to adenylate cyclase when expressed in cell lines, native guinea pig hippocampus, and cultured vascular smooth muscle cells.

The greatest abundance of 5-HT$_7$ mRNA is found in the brain where it is discretely located within thalamus, hypothalamus, and various limbic and cortical regions. Autoradiographic techniques confirm that the distribution of 5-HT$_7$ receptor binding sites in rat and guinea pig brain matches, to a large extent, the mRNA distribution (To, et al., *J. Pharmocol.*, 1995, 115, 107–116).

Preliminary data support that the 5-HT$_7$ receptor may be involved in the pathophysiology of sleep disorders, depression, (Schwartz, et al., *Adv. Int. Med.* 1993, 38, 81–106) and schizophrenia (Roth, et al., *J. Pharmacol. Exp. Ther.*, 1994, 268, 1403–1410). The 5-HT$_7$ receptor stimulation has caused relaxation of the blood vessels in monkey (Leung, et al. *Br. J. Pharmocol.*, 1996, 117, 926–930), dog (Cushing, et al. *J. Pharmocol. Exp. Ther.*, 1996, 277, 1560–1566) and rabbit (Martin, et al., *Br. J. Pharmocol.*, 1995, 114, 383). Therefore, the therapeutic utility of 5-HT$_7$ receptor ligands requires the discovery of selective therapeutic agents. The present invention discloses novel 5-HT$_7$ receptor antagonists.

SUMMARY OF THE INVENTION

Accordingly, one object of the present invention is to provide novel inhibitors of the 5-HT$_7$ receptor or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

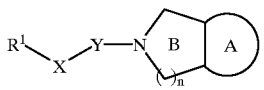

or pharmaceutically acceptable salt forms thereof, wherein $R^1$, X, Y, n and A are defined below, are effective 5-HT$_7$ inhibitors.

DETAILED DESCRIPTION OF PREFERRED EMBODIMENTS

[1] Thus, in a first embodiment, the present invention provides a novel compound of formula (I):

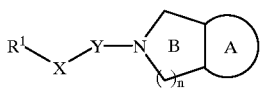

or a stereoisomer or pharmaceutically acceptable salt form thereof, wherein:

$R^1$ is selected from a $C_{6-10}$ carbocyclic aromatic residue substituted with 1–3 $R_{1a}$, and a 5–10 membered aromatic heterocyclic system containing from 1–4 heteroatoms selected from N, O, and S substituted with 0–2 $R^{1a}$;

$R^{1a}$ is independently selected at each occurrence from halo, —NO$_2$, —CN, —CF$_3$ and —CF$_2$CF$_3$;

X is selected from -S(O)p—, —C(O)—, —O—, —CH(OH)—, —CH(OC(O)CH$_3$)—, —NR$^{4a}$—, —S(O)$_2$NR$^4$— and a five membered saturated, partially saturated or unsaturated ring containing 0–2 heteroatoms selected from the group consisting of O and N; with the proviso that when X is a five membered saturated, partially saturated or unsaturated ring containing 0–2 heteroatoms selected from O and N, $R^1$ may be an unsubstituted $C_{6-10}$ carbocyclic aromatic residue;

$R^4$ is selected from hydrogen and $C_{1-6}$ alkyl;

$R^{4a}$ is taken together with $R^1$ to form a 5 or 6-membered fused heterocyclic ring containing 1–2 heteroatoms selected from O or N, and substituted with 1 or 2 carbonyl groups;

Y is $C_{1-3}$ alkylene;

A is selected from a 5 or 6 membered saturated, partially saturated or unsaturated ring which contains from 0–1 heteroatoms selected from N, O, and S substituted with 0–3 $R^5$, napthyl substituted with 0–3 $R^5$, and napthyl fused with ring B substituted with 0–3 $R^5$;

$R^5$ is selected from $C_{1-5}$ alkyl, halo and —OCH$_3$;

n is selected from 1, 2, and 3; and p is selected from 0, 1, and 2.

[2] In a preferred embodiment, the present invention provides novel compounds, wherein:

$R^1$ is phenyl substituted with 1–3 $R^{1a}$;

$R^{1a}$ is selected independently at each occurrence from halo, —CN, —CF$_3$ and —CF$_2$CF$_3$;

X is selected from —S(O)$_2$—, —S—, —NR$^{4a}$—, —C(O)—, isoxazolyl and isoxazolinyl;
R$^{4a}$ is taken together when R$^1$ is phenyl to form a 5 membered fused cyclic urea;
Y is propylene;
A is selected from phenyl substituted with 0–3 R$^5$, napthyl substituted with 0–3 R$^5$ and napthyl fused with ring B substituted with 0–3 R$^5$;
R$^5$ is selected independently at each occurrence from Cl-S alkyl, halo and —OCH$_3$; and
n is selected from 1 and 2.

[3] In a more preferred embodiment, the present invention provides novel compounds, wherein:
R$^1$ is phenyl substituted with 1–3 R$^{1a}$;
R$^{1a}$ is selected independently at each occurrence from para-halo and meta-fluoro;
X is selected from —S(O)$_2$—, —S— and —C(O)—;
Y is propylene;
A is phenyl substituted with 0–2 R$^5$;
R$^5$ is selected independently at each occurrence from C$_{1-5}$ alkyl, halo and —OCH$_3$; and
n is selected from 1 and 2.

[4] In a further more preferred embodiment, the present invention provides novel compounds, wherein:
R$^1$ is phenyl substituted with 1–3 R$^{1a}$;
R$^{1a}$ is meta-fluoro;
X is selected from —S(O)$_2$—, —S— and —C(O)—;
Y is propylene;
A is phenyl substituted with 0–2 R$^5$;
R$^5$ is selected independently at each occurrence from C$_{1-5}$ alkyl, halo and —OCH$_3$; and n is selected from 1 and 2.

[5] In an even further more preferred embodiment, the present invention provides a compound selected from the group:
1,3-Dihydro-2-((4-(4-fluorophenyl)-4-oxobutyl))isoindole,
1,3-Dihydro-2-((4-(4-fluorophenyl)-4-hydroxybutyl)) isoindole,
1,3-Dihydro-2-((4-(4-fluorophenyl)-4-acetoxybutyl)) isoindole,
2-((4-(4-Fluorophenyl)-4-oxobutyl))-1,2,3,4-tetrahydroisoquinoline,
1,3-Dihydro-2-((4-(4-fluorophenyl)-4-oxobutyl)) benz[f] isoindole,
2-((4-(4-Pyridyl)-4-oxobutyl))-1,2,3,4-tetrahydroisoquinoline,
2-((4-(3-Fluorophenyl)-4-oxobutyl))-1,2,3,4-tetrahydroisoquinoline,
1,3-Dihydro-2-((4-(4-fluorophenyl)-4-oxobutyl))-1H-benz[de] isoquinoline, 2-((4-Oxo-4-(2-thienyl)butyl))-1,2,3,4-tetrahydroisoquinoline,
6,7-Dimethoxy-2-((4-(4-fluorophenyl)oxobutyl))-1,2,3,4-tetrahydroisoquinoline,
2-((3-(1,3-Dihydro-2H-benzimidazol-2-one)-1-ylpropyl))-1,2,3,4-tetrahydroisoquinoline,
2-(3-Phenylisoxazol-5-yl)methyl-1,2,3,4-tetrahydroisoquinoline,
(+/−)-2-((3-(4-Fluorophenyl)-2-isoxazolin-5-yl)methyl-1,2,3,4-tetrahydroisoquinoline,
1,3-Dihydro-2-((3-(4-fluorophenoxy)propyl))isoindole,
2-((3-(4-Fluorophenylthio)propyl))-1,2,3,4-tetrahydroisoquinoline,
1,3-Dihydro-2-((3-(4-fluorophenylthio)propyl))isoindole,
1,3-Dihydro-2-((3-(4-fluorophenylsulfonyl)propyl)) isoindole,
2-((3-(4-Fluorophenylsulfonyl)propyl))-1,2,3,4-tetrahydroisoquinoline
2-((3-(3-Fluorophenylthio)propyl))-1,2,3,4-tetrahydroisoquinoline
2-((3-(3-Fluorophenylsulfonyl)propyl))-1,2,3,4-tetrahydroisoquinoline
1,3-Dihydro-2-((4-(4-pyridyl)-4-oxobutyl))isoindole,
1,3-Dihydro-2-((4-(3-pyridyl)-4-oxobutyl))isoindole,
1,3-Dihydro-2-((4-(4-nitrophenyl)-4-oxobutyl))isoindole,
1,3-Dihydro-2-((4-(3-nitrophenyl)-4-oxobutyl))isoindole,
1,3-Dihydro-2-((4-(2-thienyl)-4-oxobutyl))isoindole,
1,3-Dihydro-2-((4-(3-thienyl)-4-oxobutyl))isoindole,
2-((4-(3-Pyridyl)-4-oxobutyl))-1,2,3,4-tetrahydroisoquinoline,
2-((4-(4-Nitrophenyl)-4-oxobutyl))-1,2,3,4-tetrahydroisoquinoline,
2-((4-(3-Nitrophenyl)-4-oxobutyl))-1,2,3,4-tetrahydroisoquinoline,
2-((4-(3-Thienyl)-4-oxobutyl))-1,2,3,4-tetrahydroisoquinoline,
2-((3-(4-Fluorophenylsulfonyl)propyl))-1,2,3,4-tetrahydroisoquinoline,
2-((3-(4-Pyridylsulfonyl)propyl))-1,2,3,4-tetrahydroisoquinoline,
2-((3-(4-Nitrophenylsulfonyl)propyl))-1,2,3,4-tetrahydroisoquinoline,
2-((3-(3-Nitrophenylsulfonyl)propyl))-1,2,3,4-tetrahydroisoquinoline,
2-((3-(2-Thienylsulfonyl)propyl))-1,2,3,4-tetrahydroisoquinoline,
2-((3-(3-Thienylsulfonyl)propyl))-1,2,3,4-tetrahydroisoquinoline,
1,3-Dihydro-2-((1-(3-thienylsulfonyl)propyl))isoindole,
1,3-Dihydro-2-((1-(2-thienylsulfonyl)propyl))isoindole,
1,3-Dihydro-2-((1-(4-fluorophenylsulfonyl)propyl)) isoindole,
1,3-Dihydro-2-((1-(3-fluorophenylsulfonyl)propyl)) isoindole,
1,3-Dihydro-2-((1-(4-nitrophenylsulfonyl)propyl)) isoindole,
1,3-Dihydro-2-((1-(3-nitrophenylsulfonyl)propyl)) isoindole,
1,3-Dihydro-2-((-(4-pyridylsulfonyl)propyl))isoindole, and
1,3-Dihydro-2-((1-(3-pyridylsultonyl)propyl))isoindole.

[6] In a second embodiment, the present invention provides a novel compound of formula (II):

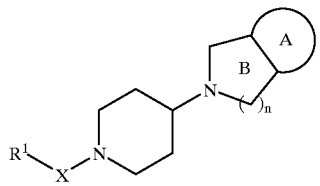

(II)

or a stereoisomer or pharmaceutically acceptable salt form thereof, wherein:
R$^1$ is selected from a C$_{6-10}$ carbocyclic aromatic residue substituted with 1–3 R$_{1a}$, and a 5–10 membered aromatic heterocyclic system containing from 1–4 heteroatoms selected from N, O, and S, substituted with 0–2 R$^{1a}$;
R$^{1a}$ is independently selected at each occurrence from (CH$_2$)$_r$OR$^{1d}$, halo, C$_{1-4}$ alkyl, (CH$_2$)$_r$—C$_{3-6}$ cycloalkyl, C$_{2-6}$ alkenyl, C$_{2-6}$ alkynyl, —CN, —NO$_2$, —OCF$_3$, (CH$_2$)$_r$NR$^{1b}$R$^{1c}$, (CH$_2$)$_r$SO$_2$R$^{1d}$, (CH$_2$)$_r$C(O)OH, (CH$_2$)$_r$C(O)OR$^{1d}$, (CH$_2$)$_r$OC(O)R$^{1d}$, (CH$_2$)$_r$C(O)R$^{1d}$, (CH$_2$)$_r$NR$^{1b}$C(O)R$^{1c}$, (CH$_2$)$_r$C(O)NR$^{1b}$R$^{1c}$, (CH$_2$)$_r$SR$^{1d}$, (CH$_2$)$_r$CH(=NR$^{1b}$)NR$^{1b}$R$^{1c}$, (CH$_2$)$_r$SO$_2$NR$^{1b}$R$^{1c}$, (CH$_2$)$_r$SO$_2$NR$^{1b}$R$^{1c}$, (CH$_2$)$_r$(CF$_2$)$_r$CF$_3$ and (CH$_2$)$_r$—phenyl substituted with 0–3 R$^{1e}$;

$R^{1b}$ and $R^{1c}$ are independently selected at each occurrence from hydrogen, $C_{1-6}$ alkyl, $C_{3-6}$ cycloalkyl, $C_{2-6}$ alkenyl, $C_{2-6}$ alkynyl and $(CH_2)_r$—phenyl substituted with 0–3 $R^{1e}$;

$R^{1d}$ is independently selected at each occurrence from $C_{1-6}$ alkyl and $(CH_2)_r$—phenyl substituted with 0–2 $R^{1e}$;

$R^{1e}$ is independently selected at each occurrence from H, —$(CH_2)_r$OR1f, halo, $C_{1-4}$ alkyl, CN, $NO_2$, and —$CF_3$;

$R^{1f}$ is selected from hydrogen and $C_{1-5}$ alkyl;

$R^{1g}$ is $C_{1-5}$ alkyl;

X is selected from —$CR^6R^7$—, —$CR^2R^3$—, —C(O)—, —O—, —$S(O)_2$—, —$S(O)_2NR^4$— and $NR^{4a}$;

$R^4$ is selected independently at each occurrence from hydrogen, $C_{1-6}$ alkyl, $(CH_2)_r$—$C_{3-7}$ cycloalkyl, $(CH_2)_r$—aryl, and $(OH_2)_r$—heteroaryl;

$R^{4a}$ is taken together with $R^1$ to form a 5 or 6-membered fused heterocyclic ring containing 1–2 heteroatoms selected from O and N, substituted with 1 or 2 carbonyl groups;

$R^6$ is selected independently at each occurrence from hydrogen, $C_{1-6}$ alkyl, $C_{2-6}$ alkenyl, $C_{2-6}$ alkynyl, $(CH_2)_r$—$C_{3-6}$ cycloalkyl, $(CH_2)_r$—phenyl, —OH, —OC(O)$R^{6a}$, $C(O)R^{6a}$ and $C(O)OR^{6a}$;

$R^{6a}$ is selected independently from $C_{1-6}$ alkyl, phenyl and benzyl;

$R^7$ is selected from hydrogen and $C_{1-5}$ alkyl;

A is selected from a 5 or 6 membered saturated, partially saturated or unsaturated ring which contains from 0–1 heteroatoms selected from N, O, and S substituted with 0–3 $R^5$, napthyl substituted with 0–3 $R^5$, and napthyl fused with ring B substituted with 0–3 $R^5$;

$R^5$ is selected independently at each occurrence from $(CH_2)_r$OR$^{5d}$, halo, $C_{1-4}$ alkyl, $(CH_2)_r$—$C_{3-6}$ cycloalkyl, $C_{2-6}$ alkenyl, $C_{2-6}$ alkynyl, —CN, —$NO_2$, —$OCF_3$, $(CH_2)_r$NR$^{5b}$R$^{5c}$, $(CH_2)_r$SO$_2$R$^{5d}$, $(CH_2)_r$C(O)OH, $(CH_2)_r$C(O)OR$^{5d}$, $(CH_2)_r$OC(O)R$^{5d}$, $(CH_2)_r$C(O)R$^{5b}$, $(CH_2)_r$NR$^{5b}$C(O)R$^{5c}$, $(CH_2)_r$C(O)NR$^{5b}$R$^{5c}$, $(CH_2)_r$SR$^{5d}$, $(CH_2)_r$CH($=$NR$^{5b}$)NR$^{5b}$R$^{5c}$, $(CH_2)_r$SO$_2$NR$^{5b}$R$^{5c}$, $(CH_2)_r$SO$_2$NR$^{5b}$R$^{5c}$, $(CH_2)_r(CF_2)_rCF_3$ and $(CH_2)_r$—phenyl substituted with 0–3 $R^{5e}$;

$R^{5b}$ and $R^{5c}$ are independently selected at each occurrence from hydrogen, $C_{1-6}$ alkyl, $C_{3-6}$ cycloalkyl, $C_{2-6}$ alkenyl, $C_{2-6}$ alkynyl, $(CH_2)_r$—phenyl;

$R^{5d}$ is independently selected at each occurrence from $C_{1-6}$ alkyl, phenyl substituted with 0–2 $R^{5e}$, and benzyl substituted with 0–2 $R^{5e}$;

$R^{5e}$ is independently selected at each occurrence from hydrogen, —$(CH_2)_r$oR$^{5f}$, halo, $C_{1-4}$ alkyl, CN, $NO_2$, and —$CF_3$;

$R^{5f}$ is selected from hydrogen and $C_{1-5}$ alkyl;

$R^{5g}$ is $C_{1-5}$ alkyl;

n is selected from 1, 2, and 3;

r is selected from 0, 1, and 2.

[7] In a preferred embodiment, the present invention provides novel compounds, wherein:

$R^1$ is phenyl substituted with 1–3 $R^{1a}$;

$R^{1a}$ is selected from halo, —CN, —$CF_3$ and —$CF_2CF_3$;

A is selected from phenyl substituted with 0–3 $R^5$, napthyl substituted with 0–3 $R^5$ and napthyl fused to ring B substituted with 0–3 $R^5$;

X is selected from —C(O)— and —$S(O)_2$—;

$R^5$ is independently selected at each occurrence from $C_{1-5}$ alkyl, halo and —$OCH_3$; and n is selected from 1 and 2.

[8] In a more preferred embodiment, the present invention provides novel compounds, wherein:

$R^1$ is phenyl substituted with 1–2 $R^{1a}$;

$R^{1a}$ is selected from para-halo and meta-halo;

A is phenyl substituted with 0–3 $R^5$;

X is selected from —C(O)— and —$S(O)_2$—;

$R^5$ is independently selected at each occurrence from $C_{1-5}$ alkyl, halo and —$OCH_3$; and n is selected from 1 and 2.

[9] In a further more preferred embodiment, the present invention provides a compound selected from the group:

2-((1-(4-Fluorophenylsulfonyl)-4-piperidyl))-1,2,3,4-tetrahydroisoquinoline, 2-((1-(3-Fluorophenylsulfonyl)-4-piperidyl))-1,2,3,4-tetrahydroisoquinoline, 2-((1-(3-Fluorophenylsulfonyl)-4-piperidyl))-1,2,3,4-tetrahydroisoquinoline, 2-((1-(4-Pyridylsulfonyl)-4-piperidyl))-1,2,3,4-tetrahydroisoquinoline, 2-((1-(3-Pyridylsulfonyl)-4-piperidyl))-1,2,3,4-tetrahydroisoquinoline, 2-((1-(4-Nitrophenylsulfonyl)-4-piperidyl))-1,2,3,4 tetrahydroisoquinoline, 2-((1-(3-Nitrophenylsulfonyl)-4-piperidyl))-1,2,3,4-tetrahydroisoquinoline, 2-((1-(2-Thienylsulfonyl)-4-piperidyl))-1,2,3,4-tetrahydroisoquinoline, 2-((1-(3-Thienylsulfonyl)-4-piperidyl))-1,2,3,4-tetrahydroisoquinoline, 1,3-Dihydro-2-((1-(3-thienylsulfonyl)-4-piperidyl)) isoindole, 1,3-Dihydro-2-((1-(2-thienylsulfonyl)-4-piperidyl)) isoindole, 1,3-Dihydro-2-((1-(4-fluorophenylsulfonyl)-4-piperidyl)) isoindole, 1,3-Dihydro-2-((1-(3-fluorophenylsulfonyl)-4-piperidyl)) isoindole, 1,3-Dihydro-2-((1-(4-nitrophenylsulfonyl)-4-piperidyl)) isoindole, 1,3-Dihydro-2-((1-(3-nitrophenylsulfonyl)-4-piperidyl)) isoindole, 1,3-Dihydro-2-((1-(4-pyridylsulfonyl)-4-piperidyl)) isoindole, and 1,3-Dihydro-2-((1-(3-pyridylsulfonyl)-4-piperidyl)) isoindole, or a pharmaceutically acceptable salt form thereof.

[10] In a third embodiment, the present invention provides for a novel compound of formula (III):

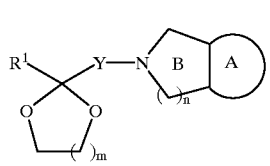

(III)

or a stereoisomer or pharmaceutically acceptable salt form thereof, wherein:

$R^1$ is selected from a $C_{6-10}$ carbocyclic aromatic residue substituted with 1–3 $R_{1a}$, and a 5–10 membered aromatic heterocyclic system containing from 1–4 heteroatoms selected from N, O, and S, substituted with 0–2 $R^{1a}$;

$R^{1a}$ is independently selected at each occurrence from $(CH_2)_r$OR$^{1d}$, halo, $C_{1-4}$ alkyl, $(CH_2)_r$—$C_{3-6}$ cycloalkyl, $C_{2-6}$ alkenyl, $C_{2-6}$ alkynyl, —CN, —$NO_2$, —$OCF_3$, $(CH_2)_r$NR$^{1b}$R$^{1c}$, $(CH_2)_r$SO$_2$R$^{1d}$, $(CH_2)_r$C(O)OH, $(CH_2)_r$C(O)OR$^{1d}$, $(CH_2)_r$OC(O)R$^{1d}$, $(CH_2)_r$C(O)R$^{1d}$, $(CH_2)_r$NR$^{1b}$C(O)R$^{1c}$, $(CH_2)_r$C(O)NR$^{1b}$R$^{1c}$, $(CH_2)_r$SR$^{1d}$, $(CH_2)$rCH($=$NR$^{1b}$)NR$^{1b}$R$^{1c}$, $(CH_2)_r$SO$_2$NR$^{1b}$R$^{1c}$, $(CH_2)_r$SO$_2$NR$^{1b}$R$^{1c}$, $(CH_2)_r(CF_2)_rCF_3$ and $(CH_2)_r$—phenyl substituted with 0–3 $R^{1e}$;

$R^{1b}$ and $R^{1c}$ are independently selected at each occurrence from hydrogen, $C_{1-6}$ alkyl, $C_{3-6}$ cycloalkyl, $C_{2-6}$ alkenyl, $C_{2-6}$ alkynyl and $(CH_2)_r$—phenyl substituted with 0–3 $R^{1e}$;

$R^{1d}$ is independently selected at each occurrence from $C_{1-6}$ alkyl and $(CH_2)_r$—phenyl substituted with 0–2 $R^{1e}$;

$R^{1e}$ is independently selected at each occurrence from H, —$(CH_2)_r$OR1f, halo, $C_{1-4}$ alkyl, CN, $NO_2$, and —$CF_3$;

$R^{1f}$ is selected from hydrogen and $C_{1-5}$ alkyl;

$R^{1g}$ is $C_{1-5}$ alkyl;

$R^4$ is selected independently at each occurrence from hydrogen, $C_{1-6}$ alkyl, $(CH_2)_r$—$C_{3-7}$ cycloalkyl, $(CH_2)_r$—aryl, and $(CH_2)_r$—heteroaryl;

$R^{4a}$ is taken together with $R^1$ to form a 5 or 6-membered fused heterocyclic ring containing 1–2 heteroatoms selected from O and N substituted with 1 or 2 carbonyl groups;

$R^6$ is selected independently at each occurrence from hydrogen, $C_{1-6}$ alkyl, $C_{2-6}$ alkenyl, $C_{2-6}$ alkynyl, $(CH_2)_r$—$C_{3-6}$ cycloalkyl, $(CH_2)_r$—phenyl, —OH, —OC(O)$R^{6a}$, C(O)$R^{6a}$, C(O)OR$^{6a}$;

$R^{6a}$ is selected independently from $C_{1-6}$ alkyl, phenyl and benzyl; $R^7$ is selected from hydrogen and $C_{1-5}$ alkyl;

Y is $C_{1-3}$ alkylene;

A is selected from a 5 or 6 membered saturated, partially saturated or unsaturated ring which contains from 0–1 heteroatoms selected from N, O, and S, substituted with 0–3 $R^5$, napthyl substituted with 0–3 $R^5$, and napthyl fused with ring B substituted with 0–3 $R^5$;

$R^5$ is selected independently at each occurrence from $(CH_2)_r$OR$^{5d}$, halo, $C_{1-4}$ alkyl, $(CH_2)_r$—$C_{3-6}$ cycloalkyl, $C_{2-6}$ alkenyl, $C_{2-6}$ alkynyl, —CN, —$NO_2$, —$OCF_3$, $(CH_2)_r$NRbR$^{5c}$, $(CH_2)_r$SO$_2$R$^{5d}$, $(CH_2)_r$C(O)OH, $(CH_2)_r$C(O)OR$^{5d}$, $(CH_2)_r$OC(O)R$^{5d}$, $(CH_2)_r$C(O)R$^{5b}$, $(CH_2)_r$NR$^{5b}$C(O)R$^{5c}$, $(CH_2)_r$C(O)NR$^{5b}$R$^{5c}$, $(CH_2)_r$SR$^{5d}$, $(CH_2)_r$CH(=NR$^{5b}$)NR$^{5b}$R$^{5c}$, $(CH_2)_r$SO$_2$NR$^{5b}$R$^{5c}$, $(CH_2)_r$SO$_2$NR$^{5b}$R$^{5c}$, $(CH_2)_r(CF_2)_r$CF$_3$ and $(CH_2)_r$—phenyl substituted with 0–3 $R^{5e}$;

$R^{5b}$ and $R^{5c}$ are independently selected at each occurrence from hydrogen, $C_{1-6}$ alkyl, $C_{3-6}$ cycloalkyl, $C_{2-6}$ alkenyl, $C_{2-6}$ alkynyl, $(CH_2)_r$—phenyl;

$R^{5d}$ is independently selected at each occurrence from $C_{1-6}$ alkyl, phenyl substituted with 0–2 $R^{5e}$, and benzyl substituted with 0–2 $R^{5e}$;

$R^{5e}$ is independently selected at each occurrence from hydrogen, —$(CH_2)_r$OR$^{5f}$, halo, $C_{1-4}$ alkyl, CN, $NO_2$, and —$CF_3$;

$R^{5f}$ is selected from hydrogen and $C_{1-5}$ alkyl;

$R^{5g}$ is $C_{1-5}$ alkyl;

n is selected from 1, 2, and 3;

r is selected from 0, 1, and 2; and m is selected from 1, 2, and 3.

[11] In a preferred embodiment, the present invention provides for novel compounds, wherein:

$R^1$ is phenyl substituted with 1–3 $R^{1a}$;

$R^{1a}$ is selected independently at each occurrence from halo, —CN, —$CF_3$ and —$CF_2CF_3$;

Y is propylene;

A is selected from phenyl substituted with 0–3 $R^5$, napthyl substituted with 0–3 $R^5$ and napthyl fused to ring B substituted with 0–3 $R^5$;

$R^5$ is selected independently at each occurrence from $C_{1-5}$ alkyl, halo and —$OCH_3$;

n is selected from 1 and 2; and m is 1.

[12] In a more preferred embodiment, the present invention provides for novel compounds, wherein:

$R^1$ is phenyl substituted with 1–2 $R^{1a}$;

$R^{1a}$ is selected from para-halo and meta-halo;

A is phenyl substituted with 0–3 $R^5$;

Y is $C_{1-3}$ alkylene;

$R^5$ is independently selected at each occurrence from $C_{1-5}$ alkyl, halo and —$OCH_3$; and n is selected from 1 and 2; and m is 1.

[13] In a more preferred embodiment, the present invention provides for novel compounds, wherein:

1,3-Dihydro-2-[3-((2-(4-fluorophenyl)-1,3-dioxolan-2-yl))propyl]isoindole, 1,3-Dihydro-2-[3-((2-(4-bromophenyl)-1,3-dioxolan-2-yl))propyl]isoindole, 1,3-Dihydro-2-[3-((2-(4-methylphenyl)-1,3-dioxolan-2-yl))propyl]isoindole, and 2-[3-((2-(4-Fluorophenyl)-1,3-dioxolan-2-yl))propyl]-1,2,3,4-tetrahydroisoquinoline.

In a fourth embodiment, the present invention provides pharmaceutical compositions comprising a pharmaceutically acceptable carrier and a therapeutically effective amount of at least one of the compounds of the present invention or a pharmaceutically acceptable salt form thereof.

In a fifth embodiment, the present invention provides a method of treating a central nervous system disorder, including sleep disorders, depression and schizophrenia comprising administering to a patient in need thereof a therapeutically effective amount of a compound of formula (I), (II) or (III), or a pharmaceutically acceptable salt thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^{1a}$) occurs more than one time in any constituent or formula for a compound, its definition at each occurrence is independent of its definition at every other occurrence. Thus, for example, if a group is shown to be substituted with 0–2 $R^{1a}$, then said group may optionally be substituted with up to two $R^{1a}$ groups and $R^{1a}$ at each occurrence is selected independently from the definition of $R^{1a}$. Also, combinations of substituents and/or variables are permissible only if such combinations result in stable compounds. When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

As used herein, "halo" or "halogen" refers to fluoro, chloro, bromo, and iodo.

As used herein, "carbocycle" or "carbocyclic residue" is intended to mean any stable 6- or 10-membered monocyclic or bicyclic aromatic compound. Examples of such carbocycles include phenyl, indanyl, indenyl and naphthyl.

As used herein, the term "aromatic heterocyclic system" or "aromatic heterocycle" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and C atoms in the aromatic heterocycle is not more than 1.

Examples of such aromatic heterocyclic systems include, but are not limited to, pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl and indazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amine prodrugs the amine group is attached to a group selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{14}$ alkoxycarbonyl. More preferred prodrugs are OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Preferred methods include, but are not limited to, those described below. All references cited herein are hereby incorporated in their entirety herein by reference.

Some compounds of Formula 1 may be prepared, as shown in Scheme 1, by treatment of an alkylating agent (1–1) with an amine (1–2) in the presence of a base in an appropriate solvent.

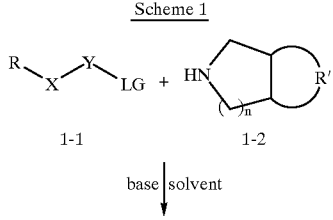

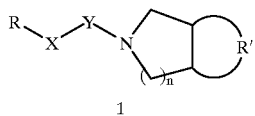

Examples of useful alkylating agents (1–1) are those where LG is a good leaving group, such as Cl, Br, I, alkylsulfonate, arylsulfonate, or perhaloalkylsulfonate. Useful bases include, but are not limited to, an excess of amine (1–2) itself, metal carbonates such as $K_2CO_3$ or $Cs_2CO_3$, metal hydroxides such as NaOH or KOH, hindered alkoxides such as potassium t-butoxide, or non-nucleophilic tertiary organic amines such as N,N-diisopropylethylamine. These bases are required to absorb the acid H-LG which is liberated during the reaction. Typical solvents include polar aprotic liquids such as DMF or THF, or protic liquids such as alcohols, including ethanol or isopropanol. It is known by those skilled in the art that the rates of alkylations of amines may be enhanced, particularly where LG is Cl or Br, by the addition of a catalytic amount of an iodide salt, such as NaI or KI, typically in the amount of 0.1 to 5 mole percent.

An alternate set of useful amine alkylation conditions utilize an organic solvent which is poorly miscible with water, such as toluene or dichloromethane, and an aqueous solution of the base, particularly metal alkoxides, along with a phase transfer catalyst (PTC). Typical phase transfer catalysts include tetraalkylammonium halides or hydroxides.

Alternatively, amine (1–2) may be initially converted into its conjugate base by treatment with a strong base, such as n-butyllithium, in an inert solvent, typically THF, near or below ambient temperature under an inert atmosphere such as nitrogen or argon. The resulting amine amion is then treated with alkylating agent (1–1), which may be introduced in an inert solvent.

In order to achieve useful reaction rates, any of the above reactions of Scheme 1 may require the application of heat from an external source.

The required alkylating agents (1–1), when not commercially available, are generally well known to those skilled in the art and are readily prepared by usual methods. In certain instances, it may be advantageous to prepare reagents (1–1) in the same reaction vessel to be used for the alkylation without purification or isolation, before addition of the amine (1–2).

Many examples of the needed amine reagents (1–2) are commercially available or are known in the literature. When the desired amine (1–2) is new, a number of literature methods are generally applicable. These include, but are not limited to, reduction of amides or imides with borane (Gawley et al., *J. Org. Chem.* 1988, 53, 5381) or lithium aluminum hydride (Uffer et al., *Helv. Chim. Acta* 1948 31, 1397; Moffett, *Org. Syn. Coll. Vol. IV* 1963, 354).

An alternate sequence for the synthesis of some compounds of Formula 1 is illustrated in Scheme 2.

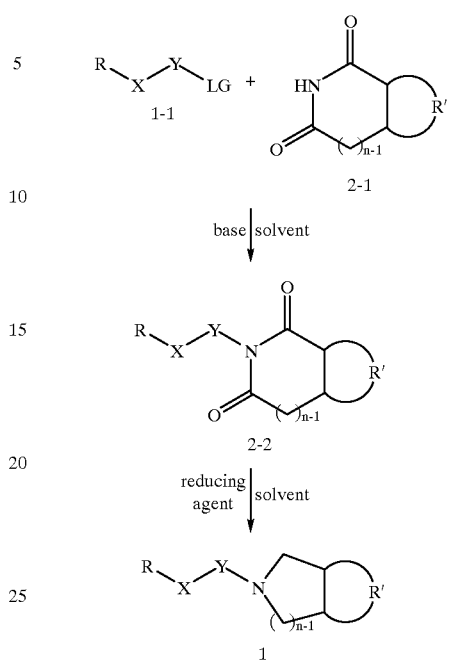

Scheme 2

An imide (2–1) is converted to its conjugate base by treatment with a base in an appropriate silvent, then allowed to react with alkylating agent (1–1) described in Scheme 1. An alkyl imide (2–2) intermediate is formed and isolated. The conjugate base of imide (2–1) may be isolated and purified in some instances, such as by precipitation by a non-polar solvent followed by filtration. Useful bases include metal alkoxides and carbonates. Alternatively, this conjugate base may be generated in situ by mixing with a non-nucleophilic base either before or after the addition of the alkylating agent (1-1).

The alkyl imide intermediate (2-2) is then converted to the amine (1) by treatment with a reducing agent, such as borane or lithium aluminum hydride, in an appropriate solvent, typically THF.

It will be recognized by those skilled in the art that certain functional group substituents on reagents (1-1) or (2-1) may not be compatible with the strongly reducing conditions described in Step 2 of Scheme 2. In such instances, these functional groups may be carried through the reaction sequence in a protected form, then released after the reduction reaction. The choice of protecting groups, and conditions for their introduction and subsequent removal, will be known to those skilled in the art, and are generally as described in Green and Wuts, *Protective Groups in Organic Synthesis*, 2nd Ed., Wiley and Sons, NY, 1991.

Where convenient, some compounds of Formula (I) may be prepared as shown in Scheme 3.

Scheme 3

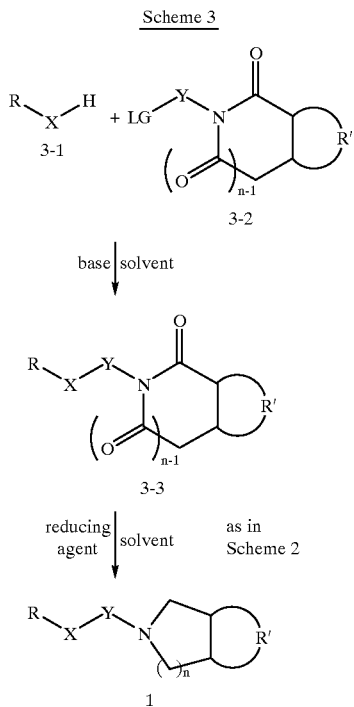

Here, the functional group X—H of reagent (3-1) is converted into its nucleophilic conjugate base by treatment with an appropriate base in a useful solvent, and allowed to react with an electrophile (3-2) wherein the leaving group LG, as described above, is connected by linker group Y to the ring nitrogen. The ring nitrogen is rendered in non-nucleophilic form in (3-2) by its incorporation into an amide or imide functional group as shown. The resulting amide or imide adduct (3-3) is then reduced to the desired amine (1) as described in Scheme 2.

The choice of base for the first reaction of Scheme 3 is dependent on the acidity of functional group X—H of (3-1). Where X—H of (3-1) is relatively acidic, such as —S—H, a fairly weak base such as a metal carbonate or hydroxide, is appropriate. For less acidic X—H such as —O—H, a stronger base such as metal hydride (e.g. sodium hydride) or alkyllithium will be useful.

The synthesis of the required electrophile (3-2) is by conversion of amide or imide (2-1) to its conjugate base and treatment with bifunctional reagent LG—Y—LG, wherein LG is a leaving group as described above. The two leaving groups may be the same, in which case an excess of the reagent would be employed to statistically ensure monoadduct (3-2), or different, whereby a stoichiometric amount is acceptable and the less reactive LG would remain in (3-2). In some instances the electrophile (3-2) may be prepared in situ and not isolated or purified, but then allowed to react with nucleophile (3-1) as just described. In such an in situ preparation of the electrophile, it may be necessary to preform the conjugate base of reagent (3-1) in a separate reaction vessel, then transfer it into the vessel containing the electrophile.

Another method useful for the preparation of some compounds of Formula 1 is shown in Scheme 4.

Scheme 4

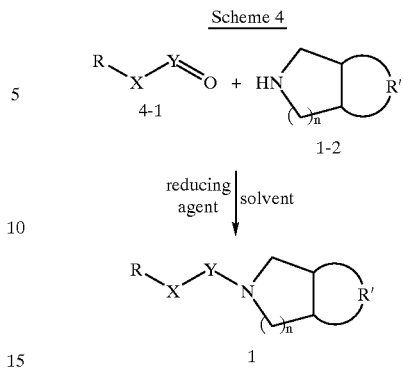

Amine (1-2) is condensed with an aldehyde or ketone (4-1) to form an enamine intermediate, which frequently is not isolated but is reduced in situ to form amine adduct (1). Many such reductive amination conditions are well known in the chemical literature by those skilled in the art, and these are not further detailed here.

Another method for the preparation of some members of Formula 1 is given in Scheme 5.

Scheme 5

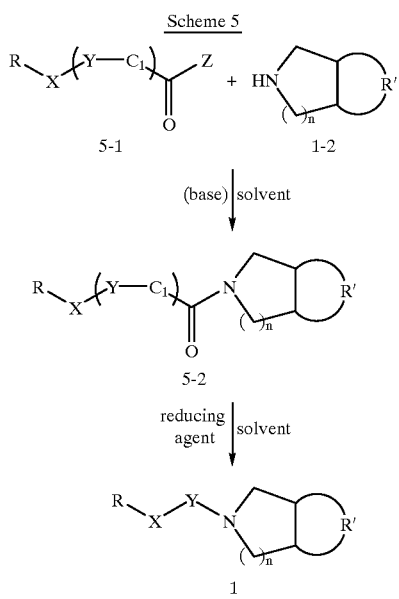

Amine (1-2) is condensed with carboxy compound (5-1) to form amide (5–2). The amide is then treated with a reducing agent, commonly borane or lithium aluminum hydride as described earlier, to generate the desired amine (1).

The carboxy group can be the parent carboxylic acid (Z is OH) in which case a coupling reagent must also be used. Many coupling reagents are known in the literature for forming amide bonds from carboxylic acids and amines; examples include, but are not limited to DCC, HBTU, TBTU, HATU, BOP, PYBOP, and alkyl chloroformates. Some of these coupling reagents, such as alkyl chloroformates, also require the presence of a non-nucleophilic base to consume the acid formed. Appropriate bases for such coupling reactions include tertiary amines such as N,N-diisopropyl-ethylamine, triethylamine, or N-methylmorpholine. Under coupling conditions such as these, the carboxy group is converted into an activated species (Z is a leaving group) which is usually not isolated, but is allowed to react in situ with the amine partner (1-2).

Alternatively to the in situ activation of the carboxylic acid for coupling, the acid can be converted into a relatively stable, activated derivative which is isolable in pure form. Examples of this type include, but are not limited to, formation of an acid halide (X is F, Cl, Br), an N-hydroxysuccinimide ester, or a pentafluorophenyl ester. Carboxylic acid pre-activating methods such as these are well known, especially in the peptide literature.

It will be recognized by those skilled in the art that one type of functional group substituent on a compound of Formula 1 may be converted into another functional group by the appropriate chemical reaction at an advantageous point in the synthetic sequence after the ring nitrogen to carbon bond formation in the Schemes is complete. Of course, such manipulations must be chemically compatible with the newly formed tertiary amine present in the compound of Formula 1.

Typically, the free base amine products of Formula 1, once prepared, are treated with an acid in an appropriate solvent to yield a salt adduct. These salt forms are often advantageous because they generally exhibit improved crystallinity, formulatability, and water solubility relative to the parent amines. Frequently, the salt adducts crystallize directly from the salt formation solvent medium, and can be isolated by filtration. In some cases, a co-solvent, usually of lesser polarity, must be added to induce crystallization.

The following examples further illustrate details for the preparation of the compounds of the present invention, and are not to be construed as limiting the inventors scope. Those skilled in the art will readily understand that known variations of the conditions and processes of the following preparative procedures can alternatively be used to prepare compounds of the present invention. All temperatures are degrees Celsius.

EXAMPLES

EXAMPLE 1
1,3-Dihydro-2-[3-((2-(4-Fluorophenyl)-1,3-Dioxolan-2-yl)) Propyl]Isoindole (1:1) Maleic Acid Salt.

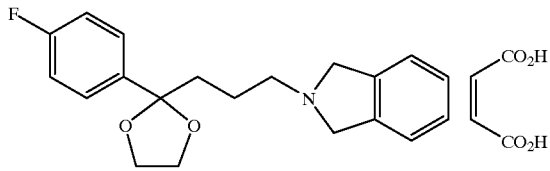

Method A, Part A: 1,3-Dihydro-2-[3-((2-(4-Fluorophenyl)-1,3-Dioxolan-2-yl))Propyl]Isoindole (1AA).

1,3-Dihydroisoindole (Gawley et al., *J. Org. Chem.* 1988, 53, 5381) (1.19 g, 10 mmol), 2-(3-chloropropyl)-2-(4-fluorophenyl)-1,3-dioxolane (2.44 g, 10 inmol), sodium iodide (10 mg), and potassium carbonate (1.52 g, 11 mmol) were heated at reflux in MeOH (25 mL) for 8 days under nitrogen. After solvent removal in vacuo, the mixture was extracted with ethyl acetate and water, then half-saturated brine. The solution was dried (magnesium sulfate), filtered, and concentrated to a brown oil. This crude product was purified by flash chromatography on silica gel 60, eluting with a gradient of hexane to ethyl acetate. Solvent removal in vacuo gave 1AA as a brown oil (0.50 g). MS (CI, $NH_3$) m/e 328 (base, $M+H^+$).

Method A, Part B: 1 1,3-Dihydro-2-[3-((2-(4-Fluorophenyl)-1,3-Dioxolan-2-yl))Propyl]Isoindole (1:1) Maleic Acid Salt A solution of maleic acid (0.18 g, 1.6 mmol) in THF (5 mL) was added to a solution of the Part A amine 1AA (0.48 g, 1.5 mmol) with stirring at room temperature (RT). The resulting clear solution was diluted with diethyl ether to generate a solid. The solid was collected by filtration, rinsed, and dried to yield 1 (0.49 g). m.p. 141–142° C. Elemental analysis. Calcld for $C_{24}H_{26}FNO_6$: C, 65.00; H, 5.91; N, 3.16. Found: C, 64.79; H, 5.96; N, 3.09. $^1$H NMR(300 MHz, $CDCl_3$, δ): 7.42–7.28 (m, 6H), 7.06–7.00 (m, 2H), 6.23 (s, 2H), 5.20–4.20 (v br, 4H), 4.05–4.00 (m, 2H), 3.78–3.73 (m, 2H), 3.33–3.28 (m, 2H), 2.00–1.89 (m, 4H), 1.60 (v br, 2H).

Method B: 1,3-Dihydro-2-[3-((2-(4-Fluorophenyl)-1,3-Dioxolan-2-yl))Propyl]Isoindole (1AA).

1,3-Dihydroisoindole (5.0 g, 85% pure, 36 mmol), 2-(3-chloropropyl)-2-(4-fluorophenyl)-1,3-dioxolane (7.4 mL, 36 mmol), potassium iodide (66 mg), and powdered potassium carbonate (5.5 g, 40 mmol) were heated to 55° C. in DMF (20 mL) for 4 days under nitrogen. Extractive work-up followed by flash chromatography as in Method A, Part A gave the same brown oil 1AA (4.4 g). The oil eventually solidified upon standing.

Method C: 1,3-Dihydro-2-[3-((2-(4-Fluorophenyl)-1,3-Dioxolan-2-yl))Propyl]Isoindole (1AA).

n-Butyllithium (2.5 M in hexanes, 34 mL, 84 mmol) was added dropwise over 10 min to a −50° solution of 1,3-dihydroisoindole (10.8 g, 93% pure, 84 mmol) in dry THF (400 mL) with stirring under nitrogen. After 1 h, 2-(3-chloropropyl)-2-(4-fluorophenyl)-1,3-dioxolane (16 mL, 80 mmol) was added, followed by a few mg of sodium iodide. The reaction was allowed to slowly warm and stir at RT overnight. The crude reaction mixture was preabsorbed onto silica gel 60 (150 g) by concentration in vacuo, then loaded on top of a silica gel flash column and eluted as above. The purest fractions were combined and evaporated to yield the same desired amine 1AA (3.3 g) as a dark solid.

Method D, Part A: N-[3-((2-(4-Fluorophenyl)-1,3-Dioxolan-2-yl))Propyl]Phthalimide (lDA).

Potassium phthalimide (37 g, 200 mmol), 2-(3-chloropropyl)-2-(4-fluorophenyl)-1,3-dioxolane (50 g, 200 mmol), and sodium iodide (0.2 g) were stirred in DMF (200 mL) under nitrogen with heating to 83° C. After 18.75 h, the reaction was concentrated in vacuo. After extractive work-up (ethyl acetate/water, then brine), drying (sodium sulfate), filtration, and concentration, the crude solid product was purified by recrystallization from boiling abs. EtOH (700 mL). The resulting solid was collected by filtration, rinsed, and dried under high vacuum at 70° C. to yield the imide adduct 1DA (56.5 g) as colorless needles. m.p. 151–152° C. Elemental analysis. Calcld for $C_{20}H_{18}FNO_4$: C, 67.60; H, 5.12; N, 3.94; F, 5.36. Found: C, 67.36; H, 4.90; N, 3.88; F, 5.39. $^1$H NMR(300 MHz, $CDCl_3$, δ): 7.84–7.80 (m, 2H), 7.73–7.69 (m, 2H), 7.42–7.37 (m, 2H), 7.02–6.96 (m, 2H), 4.05–3.94 (m, 2H), 3.79–3.67 (m, 4H), 1.96–1.91 (m, 2H), 1.80–1.70 (m, 2H). $^{13}$C NMR(300 MHz, $CDCl_3$, δ): 168.29, 162.43 (d, J=246 Hz), 138.29, 133.79, 132.14, 127.46 (d, J=9 Hz), 123.09, 114.94 (d, J=21 Hz), 109.67, 64.57, 37.90, 37.74, 22.92. IR(KBr, $cm^{-1}$): 1770 (m), 1716 (s), 1704 (s). UV(MeOH): λmax 293 nm, ε2300; λmax 268 nm, ε1600; λmax 262 nm, ε1500; λmax 241 nm, ε12,000; λmax 220 nm, ε49,000. ). MS (CI, $NH_3$) m/e 373 (base, $M+H^+$). HRMS(CI, $NH_3$) m/e Calc'd for ($M+H^+$): 356.1298. Found: 356.1319.

Method D, Part B: 1,3-Dihydro-2-[3-((2-(4-Fluorophenyl)-1,3-Dioxolan-2-yl))Propyl]Isoindole (1AA).

Imide 1DA (56.3 g, 160 mmol) and lithium aluminum hydride pellets (26 g, 640 mmol) were boiled in dry THF (1L) with mechanical stirring under nitrogen. After 22 h, $^1$H NMR analysis of an aliquot revealed incomplete reaction, so more LiAlH$_4$ (7.6 g) was added. The mixture was boiled another 16.5 h, then cooled to RT. Celite was slurried into the reaction mixture, which was then quenched by portionwise addition of Na$_2$SO$_4$.10H$_2$O (160 g) with vigorous stirring. Tetrahydrofuran was added periodically to maintain efficient stirring during the quenching. After gas evolution had ceased the mixture was filtered through additional Celite and rinsed well with THF and EtOAc. Flash chromatographic purification yielded the desired amine 1AA (43 g) as a brown solid of good purity.

Instead of chromatographic purification, the crude amine product was alternately purified by converting to the maleic acid salt as usual, recrystallizing from boiling isopropanol, and filtering to produce 1 in 41% overall yield of excellent purity from 1DA.

EXAMPLE 2

1,3-Dihydro-2-[3-((2-(4-Bromophenyl)-1,3-Dioxolan-2-yl))Propyl]Isoindole (1:1) Maleic Acid Salt

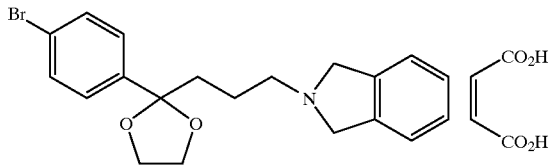

Part A: 2-(3-Chloropropyl)-2-(4-Bromophenyl)-1,3-Dioxolane (2A).

4'-Bromo-4-chlorobutyrophenone (25 g, 96 mmol), ethylene glycol (5.9 mL, 105 mmol), and p-toluenesulfonic acid monohydrate (50 mg) were heated to reflux in benzene (100 mL) under a Dean-Stark trap under nitrogen for 21 h. After cooling, half saturated aq. NaHCO$_3$ (50 mL) was added and the mixture extracted with EtOAc. The organic phase was extracted further with water, then brine, dried (Na$_2$SO$_4$), filtered, concentrated, and Kugelrohr distilled, bp (oven T) 126–146° C. (1.1 mm Hg) to yield 2A (26.4 g) as a colorless liquid. Elemental analysis. Calcld for C$_{12}$H$_{14}$BrClO$_2$: C, 47.16; H, 4.63; Cl, 11.60; Br, 26.15. Found: C, 47.24; H, 4.51; Cl, 11.67; Br, 26.31. H NMR(300 MHz, CDCl$_3$, δ): 7.48 (d, 2H, J=8 Hz), 7.33 (d, 2H, J=8 Hz), 4.08–3.96 (m, 2H), 3.81–3.69 (m, 2H), 3.53 (t, 2H, J=7 Hz), 2.10–1.98 (m, 2H), 1.91–1.80 (m, 2H). $^{13}$C NMR(300 MHz, CDCl$_3$, δ): 141.48, 131.34, 127.53, 122.09, 109.62, 64.62, 45.00, 37.62, 26.93. IR(KBr, cm$^{-1}$) 1740 (w), 1688 (w), 1590 (m), 1072 (s), 1042 (s), 1010 (s). UV(MeOH): λmax 257 nm, ϵ720; λmax 220 nm, ϵ10,650. MS (CI, NH$_3$) m/e 307 (base, M+H$^+$, 1 Br+1 Cl isotope pattern), 227 (37%). HRMS(CI, NH$_3$) m/e Calc'd for (M+H$^+$: 304.9944. Found: 304.9956.

Part B: 1,3-Dihydro-2-[3-((2-(4-Bromophenyl)-1,3-Dioxolan-2-yl))Propyl]Isoindole (2B).

1,3-Dihydroisoindole was treated with chloride 2A under conditions of Example 1, Method B, except no KI was used and the bath T was 75–80° C. The amine 2B was isolated after flash chromatographic purification as a brown solid (38% yield). MS (CI, NH$_3$) m/e 388 (base, M+H$^+$, 1 Br isotope pattern). HRMS(CI, NH$_3$) m/e Calc'd for (M+H$^+$): 390.0892. Found: 390.0895.

Part C: 1,3-Dihydro-2-[3-((2-(4-Bromophenyl)-1,3-Dioxolan-2-yl))Propyl]Isoindole (1:1) Maleic Acid Salt (2).

A solution of maleic acid (0.21 g, 1.8 mmol) was added to a solution of amine 2B (1.0 g, 70% pure, 1.8 mmol) in THF (20 mL) with stirring at RT. The resulting salt precipitate was collected by filtration, rinsed, and dried, then recrystallized from boiling abs. EtOH to yield 2 (0.47 g) as colorless flakes. m.p. 172° (dec). Elemental analysis. Calc'd for C$_{24}$H$_{26}$BrNO$_6$: C, 57.15; H, 5.21; N, 2.79; Br, 15.84. Found: C, 56.85; H, 5.21; N, 2.63; Br, 15.99. $^1$H NMR(300 MHz, DMSO-d$_6$, δ): 7.59 (d, 2H, J=8 Hz), 7.41–7.35 (m, 6H), 6.03 (s, 2H), 4.60 (br s, 2H), 4.08–3.96 (m, 2H), 3.76–3.65 (m, 2H), 3.38–3.33 (m, 2H), 1.94–1.89 (m, 2H), 1.74–1.64 (m, 2H). $^{13}$C NMR(300 MHz, DMSO-d$_6$, δ): 167.70, 141.94, 136.31, 135.02, 131.66, 128.88, 128.27, 123.29, 121.83, 109.29, 64.88, 58.35, 54.35, 36.70, 20.55. IR(KBr, cm$^{-1}$): 2800–2300 (m, br), 1704 (m), 1484 (s), 1466 (s). UV(MeOH): λmax 270 nm, ϵ1055; λmax 264 nm, ϵ1322; λmax 257 rm, ϵ1296. MS (CI, NH$_3$) m/e 388 (base, M+H$^+$, 1 Br isotope pattern). HRMS(CI, NH$_3$) m/e Calc'd for (M+H$^{+,81}$Br isotope): 390.0892. Found: 390.0887.

EXAMPLE 3

1,3-Dihydro-2-[3-((2-(4-Methylphenyl)-1,3-Dioxolan-2-yl))Propyl]Isoindole (1:1) Maleic Acid Salt

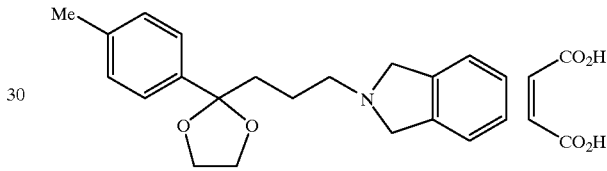

Part A: 2-(3-Chloropropyl)-2-(4-Methylphenyl)-1,3-Dioxolane (3A).

4'-Methyl-4-chlorobutyrophenone was converted to ketal 3A (99% yield) as a colorless liquid under conditions analogous to Example 2, Part A. B.p. (oven T) 110–130° C. (1.1 mm Hg). Elemental analysis. Calc'd for C$_{13}$H$_{17}$ClO$_2$: C, 64.86; H, 7.13; Cl, 14.73. Found: C, 65.23; H, 6.97; Cl, 14.43. $^1$H NMR(300 MHz, CDCl$_3$, δ): 7.33 (d, 2H, J=8 Hz), 7.15 (d, 2H, J=8 Hz), 4.05–3.94 (m, 2H), 3.82–3.71 (m, 2H), 3.51 (t, 2H, J=7 Hz), 2.34 (s, 3H), 2.04–1.99 (m, 2H), 1.87–1.80 (m, 2H). $^{13}$C NMR(300 MHz, CDCl$_3$, δ): 139.30, 137.65, 128.88, 125.60, 110.05, 64.51, 45.17, 37.81, 27.14, 21.12.

Part B: 1,3-Dihydro-2-[3-((2-(4-Methylphenyl)-1,3-Dioxolan-2-yl))Propyl]Isoindole (3B).

Prepared from chloride 3A and 1,3-dihydroisoindole analogously to Example 2B. Yield amine 3B (26% yield) as a brown viscous oil. . MS (CI, NH$_3$) m/e 324 (base, M+H$^+$). HRMS(CI, NH$_3$) m/e Calc'd for (M+H$^+$): 324.1964. Found: 324.1950.

Part C: 1,3-Dihydro-2-[3-((2-(4-Methylphenyl)-1,3-Dioxolan-2-yl))Propyl]Isoindole (1:1) Maleic Acid Salt (3).

The salt was prepared analogously to Example 1, Method A, Part B to yield 3 (50% yield) as off-white flakes. m.p. 159–161° C. (dec.). Elemental analysis. Calc'd for C$_{25}$H$_{29}$NO$_6$: C, 68.32; H, 6.65; N, 3.20. Found: C, 68.07; H, 6.72; N, 3.08. $^1$H NMR(300 MHz, DMSO-d$_6$, δ): 7.41–7.34 (m, 4H), 7.30 (d, 2H, J=8Hz), 7.19 (d, 2H, J=8Hz), 6.03 (s, 2H), 4.57 (br s, 4H), 4.05–3.94 (m, 2H), 3.74–3.63 (m, 2H), 3.37–3.31 (m, 2H), 2.30 (s, 3H), 1.93–1.88 (m, 2H), 1.74–1.63 (m, 2H). $^{13}$C NMR(300 MHz, DMSO-d$_6$, δ): 167.65, 139.50, 137.61, 136.26, 134.94, 129.20, 128.84, 125.77, 123.24, 109.60, 64.64, 58.33, 54.42, 36.88, 21.10,

EXAMPLE 4

2-[3-((2-(4-Fluorophenyl)-1,3-Dioxolan-2-yl))Propyl]-1,2,3,4-Tetrahydroisoquinoline (1:1) Maleic Acid Salt.

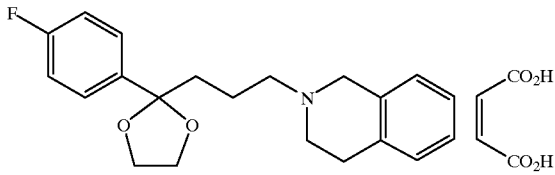

Part A: 2-[3-((2-(4-Fluorophenyl)-1,3-Dioxolan-2-yl)) Propyl]-1,2,3,4-Tetrahydroisoquinoline (4A)

1,2,3,4-Tetrahydroisoquinoline, n-BuLi, and 2-(3-chloropropyl)-2-(4-fluorophenyl)-1,3-dioxolane were allowed to react under conditions analogous to Example 1, Method C. Flash chromatographic purification provided 4A (16% yield) as a yellow oil. $^1$H NMR(300 MHz, CDCl$_3$, δ): 7.44–7.39 (m, 2H), 7.15–6.98 (m, 6H), 4.08–3.96 (m, 2H), 3.83–3.71 (m, 2H), 3.57 (s, 2H), 2.87 (t, 2H, J=6 Hz), 2.67 (t, 2H, J=6 Hz), 2.47 (t, 2H, J=7 Hz), 1.96–1.91 (m, 2H), 1.69–1.59 (m, 2H).

Part B: 2-[3-((2-(4-Fluorophenyl)-1,3-Dioxolan-2-yl)) Propyl]-1,2,3,4-Tetrahydroisoquinoline (1:1) Maleic Acid Salt (4)

Amine 4A (4.4 g) was converted to its maleic acid salt in the usual fashion to produce a colorless powder 4 (4.9 g). m.p. 160–162° C. Elemental analysis. Calc'd for C$_{25}$H$_{28}$FNO$_6$: C, 65.63; H, 6.18; N, 3.06; F, 4.15. Found: C, 65.69; H, 6.23; N, 3.02; F, 4.30. $^1$H NMR(300 MHz, DMSO-d$_6$, δ): 7.44–7.40 (m, 2H), 7.23–7.13 (m, 6H), 6.01 (s, 2H), 4.35 (br s, 2H), 4.04–3.92 (m, 2H), 3.73–3.62 (m, 2H), 3.44 (br s, 2H), 3.20–3.15 (m, 2H), 3.05–2.98 (m, 2H), 1.91–1.74 (m, 4H). 13 C NMR(300 MHz, DMSO-d$_6$, δ): 167.71, 162.29 (d, J=244 Hz), 138.81, 136.26, 131.74, 129.04, 128.95, 128.09, 127.97, 127.04 (d, J=4 Hz), 115.39 (d, J=21 Hz), 109.31, 64.78, 55.68, 52.59, 49.50, 36.97, 25.50, 18.88. IR(KBr, cm$^{-1}$): 2800–2336 (m-s, br), 1576 (s), 1506 (s). UV(MeOH): λmax 268 nm, ε860; .max 262 nm, ε1100; λmax 255 nm, ε1000. MS (CI, NH$_3$) m/e 342 (base, M+H$^+$). HRMS(CI, NH$_3$) m/e Calc'd for (M+H$^+$) 342.1869. Found: 342.1870.

EXAMPLE 5

1,3-Dihydro-2-((4-(4-Fluorophenyl)-4-Oxobutyl)) Isoindole (1:1) Maleic Acid Salt.

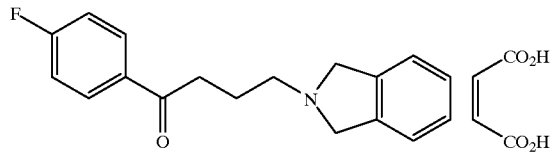

Part A: 1,3-Dihydro-2-((4-(4-Fluorophenyl)-4-Oxobutyl)) Isoindole (5A).

Ketal 1AA (3.3 g, 10 mmol) and 1 M aq. HCl (15 mL) were stirred in MeOH (60 mL) at RT for 2 days. The reaction mixture was combined with another (0.6 g of 1AA) for work-up. The MeOH was evaporated in vacuo. The remainder was extracted with EtOAc (250 mL) and 1 M aq. NaOH (30 mL), then H$_{20}$ (25 mL), and brine (10 mL). After drying (Na$_2$SO$_4$) and concentration, the product was purified by flash chromatography, eluting with a gradient of hexane to EtOAc to 20% MeOH in EtOAc. Concentration and drying in vacuo produced the amino ketone 5A as a brown solid in quantitative yield. $^1$H NMR(300 MHz, CDCl$_3$, δ): 8.02–7.97 (m, 2H), 7.19 (s, 4H), 7.17–7.08 (m, 2H), 3.93 (s, 4H), 3.09 (t, 2H, J=7 Hz), 2.82 (t, 2H, J=7 Hz), 2.03 (pentet, 2H, J=7 Hz). IR(KBr, cm-$^1$): 1682 (s), 1598 (s), 1506 (m), 1234 (s), 1156 (s), 744 (s). UV(MeOH): λmax 331 nm, ε1200; λmax 272 nm, ε2400; λmax 243 nm, ε14,000. MS (CI, NH$_3$) m/e 284 (base, M+H$^+$). HRMS(CI, NH$_3$) m/e Calc'd for (M+H$^+$): 284.1451. Found: 284.1435.

Part B: 1,3-Dihydro-2-((4-(4-Fluorophenyl)-4-Oxobutyl)) Isoindole (1:1) Maleic Acid Salt (5).

Standard procedure from 5A. m.p. 114–115° C. Elemental analysis. Calc'd for C$_{22}$H$_{22}$FNO$_5$: C, 66.16; H, 5.55; N, 3.52; F, 4.77. Found: C, 66.17; H, 5.56; N, 3.50; F, 4.67. $^1$H NMR(300 MHz, DMSO-d$_6$, δ): 8.10–8.04 (m, 2H), 7.45–7.35 (m, 6H), 6.05 (s, 2H), 4.70 (br s, 4H), 3.45 (t, 2H, J=8 Hz), 3.24 (t, 2H, J=7 Hz), 2.12–2.02 (m, 2H). $^{13}$C NMR(300 MHz, DMSO-d$_6$, δ): 197.70, 167.71, 165.50 (d, J=252 Hz), 136.18, 135.05, 133.62, 131.31 (d, J=10 Hz), 128.85, 123.26, 116.16, 58.38, 54.01,35.14, 20.26. IR(KBr, cm$^{-1}$): 3440 (w, br), 2800–2300 (m-s, br), 1684 (s), 1598 (s), 1576 (s). UV(MeOH): λmax 243 nm, ε9200. MS (CI, NH$_3$) m/e 284 (base, M+H$^+$). HRMS(CI, NH$_3$) m/e Calc'd for (M+H$^+$): 284.1451. Found: 284.1469.

EXAMPLE 6

1,3-Dihydro-2-((4-(4-Fluorophenyl)-4-Oxobutyl)) Isoindole (1:1) Hydrochloric Acid Salt.

1,3-Dihydroisoindole hydrochloride (35 g, 220 mmol), 4-chloro-(4'-fluoro)butyrophenone (44 g, 220 mmol), N,N-diisopropylethylamine (78 mL, 450 mmol), and NaI (200 mg) were heated to 950 in DMF (220 mL) with stirring under N$_2$ for 3 days. After concentration in vacuo, the mixture was extracted with EtOAc (3 L) and 1 M NaOH (500 mL), then H$_{20}$ (5×500 mL), and brine (300 mL). The mixture was dried (Na$_2$SO$_4$), filtered, concentrated, and flash chromatographed with gradient elution hexane to EtOAc to 2% MeOH in EtOAc. All major product containing fractions were combined and concentrated to yield 5A (26.2 g) as a brown solid of 75% purity (estimated by $^1$H NMR). This amine 5A was purified by conversion to its hydrochloride salt as follows. 1.0 M HCl/Et$_2$O (125 mL) was added to a solution of amine 5A (26 g, ca. 93 mmol) in CH$_2$Cl$_2$ (100 mL). The resulting solid was diluted with Et$_2$O and collected by filtration. The purity of the product salt was upgraded by sequentially recrystallizing from boiling benzene, then MeOH/Et$_2$O (2×) to yield a pale grey powder 6 (16.4 g). m.p. 174–175° C. Elemental analysis. Calc'd for C$_{18}$H$_{19}$FClNO: C, 67.60; H, 6.00; N, 4.39; F, 5.94; Cl, 11.09. Found: C, 67.62; H, 5.99; N, 4.28; F, 5.93; Cl, 10.96. $^1$H NMR(300 MHz, DMSO-d$_6$, δ): 11.35 (br s, 1H), 8.10–8.05 (m, 2H), 7.43–7.36 (m, 6H), 4.82 (br s, 2H), 4.54 (br s, 2H), 3.45–3.40 (br t, 2H, J=8 Hz), 3.25 (t, 2H, J =7 Hz), 2.07 (pentet, 2H, J=8 Hz). $^{13}$C NMR(300 MHz, DMSO-d$_6$, δ): 197.76, 165.48 (d, J=251 Hz), 134.85, 133.63, 131.34 (d, J=10 Hz), 128.75, 123.19, 116.14 (d, J=22 Hz), 57.90, 53.94, 35.66, 19.95. IR(KBr, cm$^{-1}$): 2800–2400 (m, br), 1684 (s), 1598 (s). WV(MeOH): λmax 244 nm, ε15,000. MS (CI, NH$_3$) m/e 284 (base, M+H$^+$). HRMS(CI, NH$_3$) m/e Calc'd for (M+H$^+$: 284.1451. Found: 284.1452.

EXAMPLE 7
1,3-Dihydro-2-((4-(4-Fluorophenyl)-4-Oxobutyl)) Isoindole (1:1) Methanesulfonic Acid Salt.

Methanesulfonic acid (6.3 g, 65 mmol) was added to a solution of amine 5A (18.5 g, 65 mmol) in $CH_2Cl_2$ with stirring at RT. After solvent removal in vacuo, the crude salt was recrystallized twice from boiling 2-propanol to yield 7 (11.8 g) as pale grey flakes. m.p. 145–150° C. Elemental analysis. Calc'd for $C_{19}H_{22}FNO_4S$: C, 60.14; H, 5.84; N, 3.69; F, 5.02; S, 8.45. Found: C, 60.17; H, 5.82; N, 3.59; F, 5.02; S, 8.45. $^1H$ NMR(300 MHz, DMSO-$d_6$, δ): 10.64 (br s, 1H), 8.07–8.03 (m, 2H), 7.41–7.31 (m, 6H), 4.95–4.55 (v br s, 4H), 3.45 (br t, 2H, J=8 Hz), 3.21 (t, 2H, J=7 Hz), 2.28 (s, 3H), 2.05 (pentet, 2H, J -8 Hz). $^{13}C$ NMR(300 MHz, DMSO-$d_6$, δ): 197.73, 165.51 (d, J =251 Hz), 134.79, 133.57, 131.36 (d, J=10 Hz), 128.89, 123.29, 116.16 (d, J=21 Hz), 58.35, 54.01,35.24, 20.10. IR(KBr, $cm^{-1}$): 3600–2400 (w-s, br), 1684 (s), 1598 (m), 1226 (s), 1208 (s), 1192 (s). UV(MeOH): λmax 244 nm, ε15,000. MS (CI, $NH_3$) m/e 284 (base, M+H$^+$). HRMS(CI, $NH_3$) m/e Calc'd for (M+H$^+$): 284.1451. Found: 284.1438.

EXAMPLE 8
1,3-Dihydro-2-((4-(4-Fluorophenyl)-4-Oxobutyl)) Isoindole (1:1) Fumaric Acid Salt.

Fumaric acid (9.1 g, 78 mmol) was added to a solution of amine 5A (22.2 g, 78 mmol) in $CH_2Cl_2$ (100 mL) with stirring at RT. After solvent removal in vacuo, the crude salt was stirred in $Et_2O$ (500 mL) breaking the solid chunks into small pieces with a spatula, then filtered. The resulting solid was recrystallized twice from boiling 2-propanol to yield 8 (12 g) as pale brown needles. m.p. 156–158° C. Elemental analysis, sample dried further by analyst. Calc'd for $C_{22}H_{22}FNO_5$: C, 66.16; H, 5.55; N, 3.52; F, 4.77. Found: C, 66.42; H, 5.53; N, 3.32; F, 4.91. $^1H$ NMR(300 MHz, DMSO-$d_6$, δ): 8.07–8.01 (m, 2H), 7.37–7.29 (m, 2H), 7.26–7.18 (m, 4H), 6.60 (s, 2H), 3.94 (s, 4H), 3.11 (t, 2H, J=7 Hz), 2.81 (t, 2H, J=7 Hz), 13 1.89 (pentet, 2H, J=7 Hz). $^{13}C$ NMR(300 MHz, DMSO-$d_6$, δ): 198.21, 167.60, 165.37 (d, J 251 Hz), 137.89, 134.96, 133.77, 131.21 (d, J=9 Hz), 127.76, 122.84, 116.03 (d, J=21 Hz), 58.18, 54.39, 35.66, 21.73. IR(KBr, $cm^{-1}$): 2638–2390 (m, br), 1684 (s), 1598 (s). UV(MeOH): λmax 243 nm, ε19,000. MS (CI, $NH_3$) m/e 284 (base, M+H$^+$). HRMS(CI, $NH_3$) m/e Calc'd for (M+H$^+$): 284.1451. Found: 284.1458.

EXAMPLE 9
1,3-Dihydro-2-((4-(4-Fluorophenyl)-4-Hydroxybutyl)) Isoindole (1:1) Maleic Acid Salt

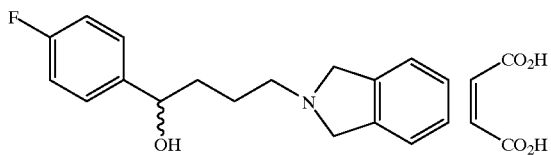

Part A: 1,3-Dihydro-2-((4-(4-Fluorophenyl)-4-Hydroxybutyl)) Isoindole (9A).

Sodium borohydride (0.26 g, 7.0 mmol) was added in two equal portions over 1.57 h to a solution of aminoketone 5A (1.0 g, 3.5 mmol) in MeOH (10 mL) with stirring at RT. After 70 min more, the solvent was evaporated in vacuo to yield alcohol 9A (1.03 g) as a brown gum. $^1H$ NMR(300 MHz, CDCl$_3$, δ): 7.36–7.31 (m, 2H), 7.20 (s, 4H), 7.02–6.96 (m, 2H), 4.74–4.66 (m, 1H), 4.03 and 3.96 (AB quartet, 4H, J=12 Hz), 2.86–2.83 (m, 2H), 2.03–1.76 (m, 4H). IR(KBr, cm 1): 3370 (m, br), 1604, (m), 1508 (s), 1220 (s), 836 (s), 744 (s).

Part B: 1,3-Dihydro-2-((4-(4-Fluorophenyl)-4-Hydroxybutyl)) Isoindole (1:1) Maleic Acid Salt (9)

Aminoalcohol 9A was converted to the 1:1 maleic acid salt in the usual way and dried under high vacuum at 56° C. to yield 9 as a grey powder. m.p. 113–114° C. Elemental analysis. Calc'd for $C_{22}H_{24}FNO_5$: C, 65.82; H, 6.04; N, 3.50; F, 4.73. Found: C, 65.68; H, 6.06; N, 3.46; F, 4.43. $^1H$ NMR(300 MHz, DMSO-$d_6$, δ): 7.38–7.35 (m, 6H), 7.12 (t, 2H, J=9 Hz), 6.02 (s, 2H), 4.70–4.52 (br s, 5H), 3.36–3.34 (m, 2H), 1.74–1.64 (m, 4H). $^{13}C$ NMR(300 MHz, DMSO-$d_6$, δ): 167.72, 161.55 (d, J=242 Hz), 142.42, 136.21, 134.88, 128.87, 128.04 (d, J=8 Hz), 123.26, 115.14 (d, J=21 Hz), 71.31, 58.31, 54.53, 36.27, 22.31. IR(KBr, $cm^{-1}$): 3368 (m, br), 2750–2300 (m, br), 1576 (s), 1508 (s). UV(MeOH): λmax 270 nm, ε2100; λmax 264 nm, ε2300; λmax 257 nm, ε2000. MS (CI, $CH_4$) m/e 286 (base, M+H$^+$), 268 (45%, M+H$^+$—$H_2O$), 190 (23%). HRMS(CI, $NH_3$) m/e Calc'd for (M+H$^+$): 286.1607. Found: 286.1603.

EXAMPLE 10
1,3-Dihydro-2-((4-(4-fluorophenyl)-4-Acetoxybutyl)) Isoindole (1:1) Maleic Acid Salt.

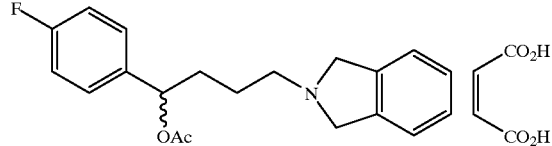

Hydroxyamine 9A (0.52 g, 1.8 mmol), acetic anhydride (0.17 mL, 1.8 mmol), and $Et_3N$ (0.25 mL, 1.8 mmol) were stirred at RT in CHC$_{13}$ (5 mL) containing a catalytic amount of 4-DMAP for 24 h. Solvent was evaporated in vacuo and the residue was extracted with EtOAc (50 mL) and 1 M NaOH (6 mL), H$_{20}$ (5 mL), and brine (5 mL). The solution was dried (Na$_2$SO$_4$), filtered, and concentrated to yield the acetate as a brown solid. The crude product was directly converted to its maleic acid salt as usual to provide 10 (0.51 g) as a grey amorphous solid. m.p. 92–95° C. (dec.). Elemental analysis. Calc'd for $C_{24}H_{26}FNO_6$: C, 65.00; H, 5.92; N, 3.17; F, 4.28. Found: C, 64.92; H, 5.92; N, 3.03; F, 4.12. $^1H$ NMR(300 MHz, DMSO-$d_6$, δ): 7.46–7.38 (m, 6H), 7.22 (t, 2H, J=9 Hz), 6.06 (s, 2H), 5.76–5.71 (m, 1H), 4.63 (br s, 4H), 3.42–3.37 (m, 2H), 2.08 (s, 3H), i 2.00–1.66 (m, 4H). $^{13}C$ NMR(300 MHz, DMSO-$d_6$, δ): 170.17, 167.70, 161.62 (d, J=244 Hz), 136.94, 136.17, 134.96, 128.84, 128.78 (d, J=8 Hz), 123.23, 115.69 (d, J=21 Hz), 74.34, 58.32, 54.02, 32.99, 22.05, 21.34. IR(KBr, cm 1): 2800–2400 (m-s, br), 1728 (s), 1574 (s), 1514 (s), 1234 (s), 1222 (s). UV(MeOH): λmax 270 nm, ε1800; λmax 263 nm, ε2000; λmax 257 nm, ε1800. MS (CI, $CH_4$) m/e 328 (42%, M+H$^+$), 268 (base), 107 (25%). HRMS(CI, $NH_3$) m/e Calc'd for (M+H$^+$): 328.1713. Found: 328.1696.

EXAMPLE 11
2-((4-(4-Fluorophenyl)-4-Oxobutyl))-1,2,3,4-Tetrahydroisoquinoline (1:1) Maleic Acid Salt.

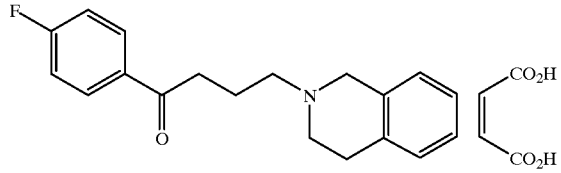

Method A. Part A: 2-((4-(4-Fluorophenyl)-4-Oxobutyl))-1,2,3,4-Tetrahydroisoquinoline (11A).

Dioxolane 4A (2.75 g, 6.0 mmol) and 1 M HCl (15 mL) were stirred in MeOH (50 mL) at RT for 3 days. After concentration in vacuo the residue was extracted with EtOAc (400 mL) and 1 M NaOH (100 mL), then $H_{20}$ (2×50 mL), and brine (25 mL). The solution was dried ($Na_2SO_4$), filtered, and concentrated to yield ketone 11A (1.9 g, quant.) as a yellow solid. $^{13}$C NMR(300 MHz, $CDCl_3$, δ): 198.60, 165.59 (d, J=254 Hz), 134.85, 134.38, 133.56, 131.65 (d, J=9 Hz), 128.61, 126.56, 126.08, 125.56, 115.52 (d, J=22 Hz), 57.36, 56.08, 50.87, 36.14, 29.12, 21.79.

Method A, Part B: 2-((4-(4-Fluorophenyl)-4-Oxobutyl))-1,2,3,4-Tetrahydroisoquinoline (1:1) Maleic Acid Salt (11).

Aminoketone 11A (1.9 g) was converted to its maleic acid salt as usual to provide 11 (2.4 g) as a colorless solid. m.p. 129–130° C. Elemental analysis. Calc'd for $C_{23}H_{24}FNO_5$: C, 66.82; H, 5.85; N, 3.40; F, 4.61. Found: C, 66.46; H, 5.62; N, 3.27; F, 4.64. $^1$H NMR(300 MHz, DMSO-$d_6$, δ): 8.10–8.03 (m, 2H), 7.43–7.21 (m, 6H), 6.03 (s, 2H), 4.41 (br s, 2H), 3.63–3.10 (m, 8H), 2.14–2.04 (m, 2H). $^{13}$C NMR (300 MHz, DMSO-$d_6$, δ): 197.75, 167.70, 165.50 (d, J=252 Hz), 136.20, 133.59, 131.83, 131.31 (d, J=9 Hz), 129.17, 128.14, 127.13, 127.07, 116.15 (d, J=21 Hz), 55.24, 52.81, 49.49, 35.26, 25.52, 18.75. IR(KBr, cm$^{-1}$): 3600–2400 (m-s, br), 1690 (s), 1596 (s), 1506 (s). UV(MeOH): λmax 243 nm, ε16,000. MS (ESI) m/e 298 (base, M+H$^+$). HRMS(CI, $NH_3$) m/e Calc'd for (M+H$^+$): 298.1607. Found: 298.1599.

Method B, Part A: 2-((4-(4-Fluorophenyl)-4-Oxobutyl))-1,2,3,4-Tetrahydroisoquinoline (11A).

Aminoketone 11A was alternatively synthesized in a single step from commercial reagents 4-chloro-4'-fluorobutyrophenone, 1,2,3,4-tetrahydroisoquinoline, N,N-diisopropylethylamine, and catalytic NaI in DMF in similar fashion to Example 6. Flash chromatographic purification, eluting with a gradient of hexane to EtOAc provided the same aminoketone 11A (49% yield) as a solid. m.p. 69–71° C. Additional 11A was recovered in mixed column fractions which could be further purified to improve the total yield.

EXAMPLE 12
1,3-Dihydro-2-((4-(4-Fluorophenyl)-4-Oxobutyl))Benz[f]Isoindole (1:1) Maleic Acid Salt.

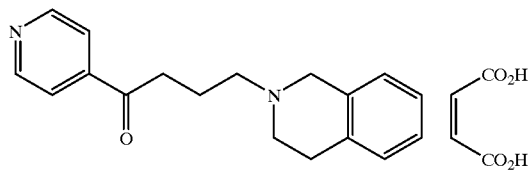

Part A: 1,3-Dihydrobenz[f]Isoindole (12A).

2,3-Naphthalene dicarboximide (5.0 g, 25 mmol) was reduced with $BH_3$-THF (1 M in THF, 100 mL, 100 mmol) according to the Gawley method used for 1,3-dihydroisoindole in Example 1, Method A, Part A. The crude product was purified by flash chromatography on silica gel 60, eluting with a gradient of 2% to 10% MeOH in $CHC_{13}$ to produce 12A (1.8 g, 43%) as a solid. m.p. 127–129° C. $^1$H NMR(300 MHz, MeOH-$d_4$, δ): 7.80–7.72 (m, 2H), 7.71 (s, 1H), 7.42–7.38 (m, 2H), 4.32 (s, 4H). MS (GC/MS, $H_{20}$) m/e 170 (base, M+H$^+$).

Part B: 1,3-Dihydro-2-((4-(4-Fluorophenyl)-4-Oxobutyl))Benz[f]Isoindole (12B).

Amine 12A was alkylated with 4-chloro-4'-fluoro butyrophenone analogously to Example 6. The crude product was purified by flash chromatography on silica gel 60, eluting with 1:1 EtOAc/hexane to yield aminoketone 12B (39% yield) as a brown solid. m.p. 148–149° C. $^1$H NMR (300 MHz, $CDCl_3$, δ): 7.98–7.93 (m, 2H), 7.78–7.73 (m, 2H), 7.58 (s, 2H), 7.42–7.35 (m, 2H), 7.06 (t, 2H, J=9 Hz), 3.98 (s, 4H), 3.06 (t, 2H, J=7 Hz), 2.81 (t, 2H, J=7 Hz), 2.09–2.00 (m, 2H). $^{13}$C NMR(300 MHz, $CDCl_3$, δ): 198.47, 165.60 (d), 139.14, 133.60 (d), 133.03, 130.60 (d), 127.74, 125.29, 120.37, 115.50 (d), 58.57, 55.35, 36.04, 23.35. IR(KBr, cm$^{-1}$): 1686 (s). MS (CI, $NH_3$) m/e 334 (base, M+H$^+$). HRMS(CI, $NH_3$) m/e Calc'd for (M+H$^+$): 334.1607. Found: 334.1623.

Part C: 1,3-Dihydro-2-((4-(4-Fluorophenyl)-4-Oxobutyl))Benz[f]Isoindole (1:1) Maleic Acid Salt (12).

Method from 12B. Recrystallized from boiling isopropanol to produce solid 12. m.p. 157–158° C. Elemental analysis. Calc'd for $C_{26}H_{24}FNO_5$: C, 69.48; H, 5.38; N, 3.13; F, 4.24. Found: C, 69.81; H, 5.40; N, 2.98; F, 4.30. $^1$H NMR(300 MHz, DMSO-$d_6$, δ): 8.10–8.05 (m, 2H), 7.95–7.85 (m, 4H), 7.55–7.50 (m, 2H), 7.22 (t, 2H, J=9 Hz), 6.20 (s, 2H), 4.90 (s, 4H), 3.60–3.52 (m, 2H), 3.25 (t, 2H, J=6 Hz), 2.30–2.19 (m, 2H). IR(KBr, cm$^{-1}$): 3600–2400 (m-s, br), 1684 (s). MS (CI, $NH_3$) m/e 334 (base, M+H$^+$). HRMS(CI, $NH_3$) m/e Calc'd for (M+H$^+$): 334.1607. Found: 334.1610.

EXAMPLE 13
2-((4-(4-Pyridyl)-4-Oxobutyl))-1,2,3,4-Tetrahydroisoquinoline (1:1) Maleic Acid Salt

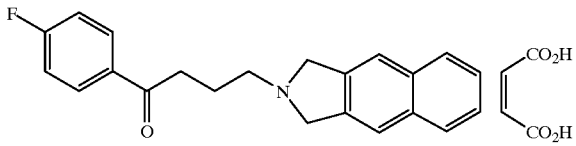

Part A: 4-(4'-Chloro-1'-Oxobutyl)Pyridine (13A).

Prepared according to Sato et. al., *Chem. Phar. Bull.* 1978 26(1), 3296 to produce 13A as a brown oil. $^1$H NMR(300 MHz, $CDCl_3$, δ): 8.85–8.80 (m, 2H), 7.80–7.75 (m, 2H), 3.69 (t, 2H, J=6 Hz), 3.20 (t, 2H, J=7 Hz), 2.30–2.30 (m, 2H). IR(KBr, cm -): 1698 (s).

Part B: 2-((4-(4-Pyridyl)-4-Oxobutyl))-1,2,3,4-Tetrahydroisoquinoline (13B).

1,2,3,4-Tetrahydroisoquinoline was alkylated with chloride 13A analogously to Example 6 to yield amine 13B (37% yield) as a solid after flash chromatographic 1 purification. $^1$H NMR(300 MHz, $CDCl_3$, δ): 8.76–8.71 (m, 2H), 7.73–7.68 (m, 2H), 7.15–6.95 (m, 4H), 3.56 (s, 2H), 3.05 (t, 2H, J=7 Hz), 2.80 (t, 2H, J=6 Hz), 2.69 (t, 2H, J=6 Hz), 2.57 (t, 2H, J=7 Hz), 2.06 (pentet, 2H, J =7 Hz). $^{13}$C NMR(300 MHz, $CDCl_3$, δ): 199.43, 150.77, 143.07, 134.67, 134.29, 128.86, 126.51, 126.10, 125.56, 121.00, 57.09, 55.88, 50.84, 36.48, 28.92, 21.84. IR(KBr, cm$^{-1}$): 1696 (s). UV(MeOH): λmax 273 nm, ε3460; λmax 267 nm, ε3090; MS(ESI) m/e 281 (base, M+H$^+$). HRMS(CI, $NH_3$) m/e Calc'd for (M+H$^+$): 281.1654. Found: 281.1638.

Part C: 2-((4-(4-Pyridyl)-4-Oxobutyl))-1,2,3,4-Tetrahydroisoquinoline (1:1) Maleic Acid Salt (13).

Usual method from 13B. m.p. 108–109° C. Elemental analysis. Calc'd for $C_{22}H_{24}NO_5$: C, 66.65; H, 6.10; N,7.08. Found: C, 66.54; H, 6.07; N, 7.01. $^1$H NMR(300 MHz, $CD_3OD$, δ): 8.76–8.74 (m, 2H), 7.90–7.88 (m, 2H), 7.30–7.19 (m, 4H), 6.21 (s, 2H), 4.88 (s, 2H), 4.46 (s, 2H), 3.61 (t, 2H, J=7 Hz), 3.40–3.18 (in, 6H), 2.30–2.20 (m, 2H). $^{13}$C NMR(300 MHz, $CDCl_3$, δ): 200.32, 171.65, 152.34, 145.34, 137.49, 133.10, 130.75, 130.31, 129.95, 129.13, 128.78, 123.65, 57.46, 55.27, 52.06, 37.31, 27.31, 20.25. IR(KBr, cm$^{-1}$): 3600–2300 (m, br), 1698 (s). UV(MeOH): λmax 272 nm, ε2340. MS(CI, NH$_3$) m/e 281 (base, M+H$^+$). HRMS(CI, NH$_3$) m/e Calc'd for (M+H$^+$): 281.1654. Found: 281.1659.

EXAMPLE 14
2-((4-(3-Fluorophenyl)-4-Oxobutyl))-1,2,3,4-Tetrahydroisoquinoline (1:1) Maleic Acid Salt
Part A: 4-Chloro-3'-Fluorobutyrophenone (14A) Prepared According to Janssen, U.S. Pat. No. 2,973,365 (1961).
Part B: 2-((4-(3-Fluorophenyl)-4-Oxobutyl))-1,2,3,4-Tetrahydroisoquinoline (14B)

1,2,3,4-Tetrahydroisoquinoline was alkylated with chloride 14A in the usual way to afford adduct 14B (58% yield) as an oil. $^1$H NMR(300 MHz, CDCl$_3$, δ): 7.74–7.71 (m, 1H), 7.65–7.60 (m, 1H), 7.43–7.36 (m, 1H), 7.25–7.19 (m, 1H), 7.15–7.08 (m, 3H), 7.00–6.98 (m, 1H), 3.61 (s, 2H), 3.05 (t, 2H, J=7 Hz), 2.88 (t, 2H, J=6 Hz), 2.72 (t, 2H, J=7 Hz), 2.59 (t, 2H, J=7 Hz), 2.05 (pentet, 2H, J =7 Hz). $^{13}$C NMR(300 MHz, CDCl$_3$, δ): 198.84, 162.80 (d), 139.30, 134.60, 130.10, 128.62, 126.56, 126.09, 125.57, 123.80, 119.80, 114.76, 57.31, 56.07, 50.87, 36.39, 29.11, 21.78. IR(KBr, cm$^{-1}$): 1688 (s). UV(MeOH): λmax 283 nm, g 2910; λmax 273 nm, ε2880; )max 266 nm, ε2430; λmax 238 nm, F 16,300. MS(CI, NH$_3$) m/e 298 (base, M+H$^+$). HRMS(CI, NH$_3$) m/e Calc'd for (M+H$^+$): 298.1607. Found: 298.1619.
Part C: 2-((4-(3-Fluorophenyl)-4-Oxobutyl))-1,2,3,4-Tetrahydroisoquinoline (1:1) Maleic Acid Salt (14)

Usual method from 14B. Recrystallized from benzene as a white solid. m.p. 139–140° C. Elemental analysis. Calc'd for C$_{23}$H$_{24}$FNO$_5$: C, 66.82; H, 5.85; N, 3.40; F, 4.61. Found: C, 66.89; H, 5.75; N, 3.26; F, 4.69. $^1$H NMR(300 MHz, CD$_3$OD, δ): 7.83 (d, 1H, J=8 Hz), 7.71–7.66 (m, 1H), 7.60–7.48 (m, 1H), 7.40–7.20 (m, 5H), 6.18 (m, 2H), 4.96 (br s, 2H), 4.50 (s, 4H), 3.64 (t, 2H, J=6 Hz), 3.39–3.29 (m, 2H), 3.28–3.19 (m, 4H), 2.29–2.19 (m, 2H). $^{13}$C NMR(300 MHz, CDCl$_3$, δ): 197.53, 169.37, 162.80, 138.60, 135.18, 130.80, 130.40, 128.02, 127.75, 126.60, 123.80, 119.80, 114.00, 55.31, 52.95, 49.74, 34.81, 24.98, 18.18. IR(KBr, cm$^{-1}$): 3600–2300 (m, br), 1688 (s). UV(MeOH): λmax 283 nm, ε2500; xmax 272 nm, ε2290; λmax 238 nn, ε16,600. MS(GC/MS, H$_2$O) m/e 298 (base, M+H$^+$).

EXAMPLE 15
1,3-Dihydro-2-((4-(3-Fluorophenyl)-4-Oxobutyl)) Isoindole (1:1) Maleic Acid Salt (15)
Part A: 1,3-Dihydro-2-((4-(3-Fluorophenyl)-4-Oxobutyl)) Isoindole (15A)

1,3-Dihydroisoindole hydrochloride was alkylated with chloride 14A in standard fashion. The product was purified by two successive flash chromatographies, eluting first with 2% MeOH in CHCl$_3$, then 33% EtOAc in hexane to provide 15A (10% yield) as a solid. $^1$H NMR(300 MHz, CDCl$_3$, δ): 7.76–7.72 (m, 2H), 7.66–7.60 (m, 1H), 7.45–7.37 (m, 1H), 7.26–7.19 (m, 1H), 7.18 (s, 4H), 3.91 (s, 4H), 3.09 (t, 2H, J=7 Hz), 2.81 (t, 2H, J=7 Hz), 2.08–1.98 (m, 2H). $^{13}$C NMR(300 MHz, CDCl$_3$, δ): 198.76, 140.05, 130.16, 130.06, 126.65, 123.71, 122.20, 119.80, 114.70, 58.94, 55.09, 36.26, 23.43. UV(MeOH): λmax 282 nm, ε3080; λmax 272 nm, ε3430; )Lmax 266 nm, ε3120; λmax 237 nm, ε17,200. MS(GC/MS, H$_{20}$) m/e 284 (base, M+H$^+$).
Part B: 1,3-Dihydro-2-((4-(3-Fluorophenyl)-4-Oxobutyl)) Isoindole (1:1) Maleic Acid Salt (15)

Standard method from 15A. Recrystallized from benzene. m.p. 130–131° C. Elemental analysis. Calc'd for C$_{22}$H$_{22}$FNO$_5$: C, 66.16; H, 5.55; N, 3.52; F, 4.77. Found: C, 66.01; H, 5.50; N, 3.47; F, 4.80. $^1$H NMR(300 MHz, CD$_3$OD, δ): 7.85–7.82 (m, 1H), 7.72–7.68 (m, 1H), 7.57–7.49 (m, 1H), 7.40–7.31 (m, 5H), 6.20 (s, 2H), 4.90 (br s, 2H), 4.76 (s, 4H), 3.53–3.48 (m, 2H), 3.24 (t, 2H, J=7 Hz), 2.25–2.15 (m, 2H). $^{13}$C NMR(300 MHz, CD$_3$OD, δ): 197.47, 169.36, 162.80, 138.60, 135.07, 133.60, 130.37, 128.74, 123.79, 122.58, 119.80, 114.00, 58.42, 54.25, 34.70, 19.59. IR(KBr, cm $^1$): 1694 (s), 1686 (s). UV(MeOH): λmax 283 nm, ε1760; λmax 271 nm, ε1830; λmax 238 nm, ε11,600. MS(GC/MS, H$_{20}$) m/e 284 (base, M+H$^+$). HRMS (CI, NH$_3$) m/e Calc'd for (M+): 283.1372. Found: 283.1373.

EXAMPLE 16
2,3-Dihydro-2-((4-(4-Fluorophenyl)-4-Oxobutyl))-1H-Benz[de]Isoquinoline (1:1) Maleic Acid Salt (16)

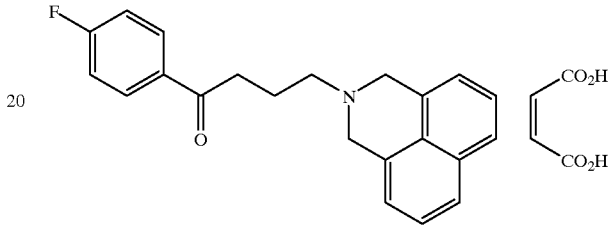

Part A: 2,3-Dihydro-1H-Benz[de]Isoquinoline (16A)

1,8-Naphthalimide (94% pure, 10 g, 48 mmol) and LiAlH$_4$ (10.4 g, 270 inmol) were stirred in dry THF (500 mL) at RT under N$_2$ for 4 days. After careful quenching with Na$_2$SO$_4$.10H$_2$O, filtration, and concentration in vacuo, the residue was extracted with EtOAc and H$_2$O, then brine, dried (MgSO$_4$), and concentrated. The crude product was purified by flash chromatography on silica gel 60, eluting with 3% to 15% MeOH in CHC$_{13}$ to provide the amine 16A (1.05 g) as a dark solid. $^1$H NMR(300 MHz, CDCl$_3$, δ): 7.68 (d, 2H, J=8 Hz), 7.38 (dd, 2H, J=8, 7 Hz), 7.15 (d, 2H, J=7 Hz), 4.29 (s, 4H), 2.60–2.40 (br s, 1H). MS(CI, NH$_3$) m/e 170 (base, M+H$^+$).
Part B: 2,3-Dihydro-2-((4-(4-Fluorophenyl)-4-Oxobutyl))-1H-Benz[de]Isoquinoline (16B)

Amine 16A (1.0 g, 5.9 mmol) was alkylated with 4-chloro-4'-fluorobutyrophenone (1.19 g, 5.9 mmol) in the usual way. The crude product was purified by flash chromatography on silica gel 60, eluting with 2% MeOH in CHCl$_3$ to provide amine adduct 16B as a brown oil. $^1$H NMR(300 MHz, CDCl$_3$, δ): 8.95–8.80 (m, 2H), 7.65 (d, 2H, J , 8 Hz), 7.36 (t, 2H, J=7 Hz), 7.15 (d, 2H, 7 Hz), 6.91 (t, 2H, J=9 Hz), 3.91 (s, 4H), 2.99 (t, 2H, J=7 Hz), 2.67 (t, 2H, J=7 Hz), 2.15–2.00 (m, 2H). IR(KBr, cm$^1$): 1684 (s). UV(MeOH): λmax 242 nm, ε27,700; λmax 227 nm, ε22,700. MS(CI, NH$_3$) m/e 334 (base, M+H$^+$). HRMS(CI, NH$_3$) m/e Calc'd for (M+H$^+$): 334.1607. Found: 334.1595.
Part C: 2,3-Dihydro-2-((4-(4-Fluorophenyl)-4-Oxobutyl))-1H-Benz[de]Isoquinoline (1:1) Maleic Acid Salt (16)

Standard method from 16B. Yield yellow solid 16. m.p. 153–155° C. Elemental analysis. Calc'd for C$_{26}$H$_{24}$FNO$_5$: C, 69.48; H, 5.38; N, 3.13; F, 4.24. Found: C, 69.21; H, 5.40; N, 3.02; F, 4.47. $^1$H NMR (300 MHz, CD$_3$OD, δ): 8.10–8.00 (m, 2H), 7.90–7.85 (m, 2H), 7.60–7.40 (m, 4H), 7.19 (t, 2H, J=9 Hz), 6.20 (s, 2H), 4.72 (s, 4H), 3.45–3.30 (m, 2H), 3.22 (t, 2H, J=7 Hz), 2.35–2.20 (m, 2H). $^{13}$C NMR(300 MHz, CD$_3$OD, δ): 197.33, 169.35, 166.00, 135.18, 132.91, 130.58, 127.94, 126.06, 125.95, 123.83, 115.20, 55.17, 54.40, 34.61, 18.62. IR(KBr, cm$^{-1}$): 3600–2400 (m, br), 1684 (s). UV(MeOH): λmax 316 nm, ε700; λmax 285 nm, ε5,700; λmax 275 nm, ε5400; λmax 226 nm, ε57,000. MS(CI, NH$_3$)

EXAMPLE 17
2-((4-Oxo-4-(2-Thienyl)Butyl))-1,2,3,4-Tetrahydroisoquinoline (1:1) Maleic Acid Salt

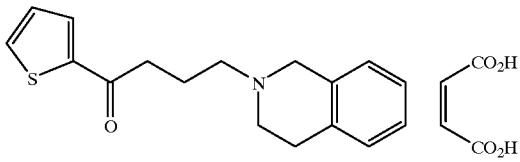

Part A: 2-((4-Oxo-4-(2-Thienyl)Butyl))-1,2,3,4-Tetrahydroisoquinoline (17A)

Prepared in standard fashion from commercially available 4-chloro-2'-butyrothienone and 1,2,3,4-tetrahydroisoquinoline. Purified by flash chromatography, eluting with 1:1 EtOAc/hexane to provide 17A (58% yield) as a yellow oil. $^1$H NMR(300 MHz, CDCl$_3$, δ): 7.72–7.70 (m, 1H), 7.60–7.58 (m, 1H), 7.15–6.98 (m, 5H), 3.62 (s, 2H), 3.01 (t, 2H, J=7 Hz), 2.87 (t, 2H, J=6 Hz), 2.72 (t, 2H, J=6 Hz), 2.59 (t, 2H, J=7 Hz), 2.10–2.00 (m, 2H). C NMR(300 MHz, CDCl$_3$, δ): 193.10, 144.56, 134.92, 134.43, 133.34, 131.79, 128.64, 128.05, 126.59, 126.08, 125.58, 57.37, 56.10, 50.83, 37.01, 29.19, 22.14. . IR(KBr, cm$^{-1}$): 1662 (s). UV(MeOH): )max 282 nm, ε260. MS(CI, NH$_3$) m/e 286 (base, M+H$^+$). HRMS(CI, NH$_3$) m/e Calc'd for (M+H$^+$): 286.1266. Found: 286.1259.

Part B: 2-((4-Oxo-4-(2-Thienyl)Butyl))-1,2,3,4-Tetrahydroisoquinoline (1:1) Maleic Acid Salt (17)

Standard method from 17A to provide solid 17. m.p. 154–155° C. Elemental analysis. Calc'd for C$_{21}$H$_{23}$NO$_5$S: C, 62.82; H, 5.77; N, 3.50; S, 8.00. Found: C, 62.58; H, 5.67; N, 3.41; S, 7.86. $^1$H NMR(300 MHz, DMSO-d$_6$, δ): 8.01 (d, 1H, J=5 Hz), 7.98–7.96 (m, 1H), 7.35–7.20 (m, 6H), 6.03 (s, 2H), 4.50–4.30 (br s, 2H), 3.60–3.00 (m, 10H), 2.15–2.00 (m, 2H). IR(KBr, cm$^{-1}$): 3600–2400 (m, br), 1666 (s). MS(CI, NH$_3$) m/e 286 (base, M+H$^+$). HRMS(CI, NH$_3$) m/e Calc'd for (M+H$^+$: 286.1266. Found: 286.1206.

EXAMPLE 18
6,7-Dimethoxy-2-((4-(4-Fluorophenyl)Oxobutyl))-1,2,3,4-Tetrahydroisoquinoline (1:1) Maleic Acid Salt

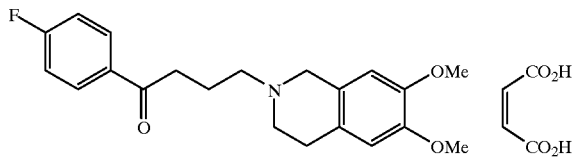

Part A: 6,7-Dimethoxy-2-((4-(4-Fluorophenyl)Oxobutyl))-1,2,3,4-Tetrahydroisoquinoline (18A)

Commercially available 6,7-dimethoxy-1,2,3,4-tetrahydroisoquinoline hydrochloride was alkylated in standard fashion to provide amine 18A (54% yield) as a brown oil. $^1$H NMR(300 MHz, CDCl$_3$, δ): 8.01–7.95 (m, 2H), 7.10 (t, 2H, J=9 Hz), 6.59 (s, 1H), 6.51 (s, 1H), 3.84 (s, 6H), 3.54 (s, 2H), 3.05 (t, 2H, J=7 Hz), 2.81–2.77 (m, 2H), 2.72–2.70 (m, 2H), 2.58 (t, 2H, J=7 Hz), 2.08–1.99 (m, 2H). IR(KBr, cm$^{-1}$): 1684 (s). MS(CI, NH$_3$) m/e 358 (base, M+H$^+$). HRMS(CI, NH$_3$) m/e Calc'd for (M+H$^+$): 358.1818. Found: 358.1828.

Part B: 6,7-Dimethoxy-2-((4-(4-Fluorophenyl)Oxobutyl))-1,2,3,4-Tetrahydroisoquinoline (1:1) Maleic Acid Salt (18)

Standard method from 18A. Yield colorless solid 18. m.p. 144–146° C. Elemental analysis, sample dried by analyst. Calc'd for C$_{25}$H$_{28}$FNO$_7$: C, 63.42; H, 5.96; N, 2.97; F, 4.01. Found: C, 63.59; H, 5.92; N, 2.73; F, 4.07. $^1$H NMR(300 MHz, DMSO-d$_6$, δ): 8.06 (dd, 2H, J=7, 6 Hz), 7.39 (t, 2H, J=9 Hz), 6.84 (s, 1H), 6.82 (s, 1H), 6.03 (s, 2H), 4.40–4.20 (br s, 2H), 3.74 (s, 3H), 3.73 (s, 3H), 3.70–3.15 (m, 8H), 3.10–2.95 (br s, 2H), 2.20–2.00 (m, 2H). IR(KBr, cm$^{-1}$): 3600–2400 (m, br), 1686 (s, br). UV(MeOH): λmax 281 nm, ε6700; λmax 236 nm, ε23,100. MS(CI, NH$_3$) m/e 358 (base, M+H$^+$). HRMS(CI, NH$_3$) m/e Calc'd for (M+H$^+$): 358.1818. Found: 358.1829.

EXAMPLE 19
(+/−)-Trans-2-((4-(4-Fluorophenyl)Oxobutyl))-Perhydroisoquinoline (1:1) Maleic Acid Salt

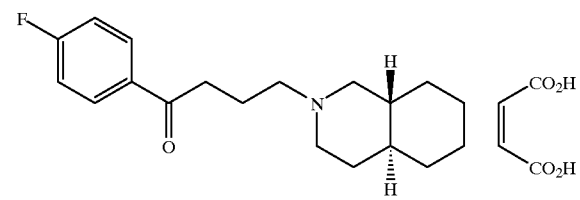

Part A: (+/−)-trans-2-((4-(4-Fluorophenyl)Oxobutyl))-Oerhydroisoquinoline (19A)

Commercially available (+/−)-trans-perhydro-isoquinoline was alkylated in the usual way, then purified by flash chromatography on silica gel 60, eluting with 1:1 EtOAc/hexane to provide 19A (65% yield) as a brown oil. $^1$H NMR(300 MHz, CDCl$_3$, δ): 8.05–7.95 (m, 2H), 7.12 (t, 2H, J=9 Hz), 2.96 (t, 2H, J=7 Hz), 2.93–2.85 (m, 1H), 2.76–2.72 (m, 1H), 2.36 (t, 2H, J=7 Hz), 2.00–1.90 (m, 3H), 1.80–1.45 (m, 6H), 1.38–1.05 (m, 4H), 1.00–0.80 (m, 3H). IR(KBr, cm$^{-1}$): 1686 (s). UV(MeOH): Jmax 337 nm, ε1700; λmax 243 nm, ε10,900.

Part B: (+/−)-trans-2-((4-(4-Fluorophenyl)Oxobutyl))-Perhydroisoquinoline (1:1) Maleic Acid Salt (19)

Standard method from 19A. Yield colorless solid 19. m.p. 157–158° C. Elemental analysis. Calc'd for C$_{23}$H$_{30}$FNO$_5$: C, 65.85; H, 7.22; N, 3.35; F, 4.54. Found: C, 65.66; H, 7.17; N, 3.23; F, 4.55. $^1$H NMR(300 MHz, DMSO-d$_6$, δ): 8.12–8.04 (m, 2H), 7.39 (t, 2H, J=9 Hz), 6.02 (s, 2H), 3.52–3.48 (m, 1H), 3.37–3.30 (m, 2H), 3.16 (t, 2H, J=7 Hz), 3.14–3.00 (m, 2H), 3.00–2.90 (m, 1H), 2.70–2.60 (m, 1H), 2.04–1.95 (m, 5H), 1.45–1.05 (m, 5 H), 1.00–0.85 (m, 2H). MS(CI, NH$_3$) m/e 304 (base, M+H$^+$). HRMS(CI, NH$_3$) m/e Calc'd for (M+H$^+$): 304.2077. Found: 304.2091.

EXAMPLE 20
2-((3-(1,3-Dihydro-2H-Benzimidazol-2-One)-1-ylpropyl))-1,2,3,4-Tetrahydroisoquinoline (1:1) Maleic Acid Salt

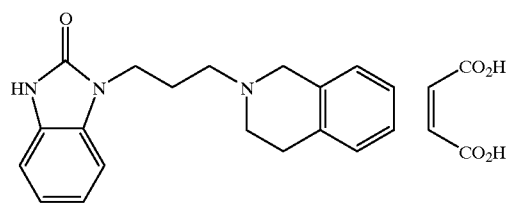

Part A: 2-((3-(1,3-Dihydro-2H-Benzimidazol-2-One)-1-ylpropyl))-1,2,3,4-Tetrahydroisoquinoline (20A)

1,2,3,4-Tetrahydroisoquinoline was alkylated with commercially available 1-(3-chloropropyl)-1,3-dihydro-2H-benzimidazole-2-one in typical fashion to provide solid 20A (90% yield) after flash chromatography, eluting with 8% MeOH in CHC$_{13}$. m.p. 141–143° C. $^1$H NMR(300 MHz, CDCl$_3$, δ): 7.20–7.00 (m, 9H), 4.01 (t, 2H, J=7 Hz), 3.62 (s, 2H), 2.91 (t, 2H, J=6 Hz), 2.71 (t, 2H, J=6 Hz), 2.58 (t, 2H, J=7 Hz), 2.08 (pentet, 2H, J=7 Hz). $^{13}$C NMR(300 MHz, CDCl$_3$, δ): 156.03, 134.78, 134.35, 130.58, 128.66, 128.20, 126.59, 126.15, 125.63, 121.36, 121.09, 109.71, 108.04, 56.08, 55.05, 50.94, 38.87, 29.19, 26.06. IR(KBr, cm$^{-1}$): 1716 (s), 1664 (m). MS(CI, NH$_3$) m/e 308 (base, M+H$^+$). HRMS(CI, NH$_3$) m/e Calc'd for (M+H$^+$): 308.1763. Found: 308.1774.

Part B: 2-((3-(1,3-Dihydro-2H-Benzimidazol-2-One)-1-ylpropyl))-1,2,3,4-Tetrahydroisoquinoline (1:1) Maleic Acid Salt (20)

Standard method from 20A to yield a solid 20. m.p. 153–154 ° C. Elemental analysis. Calc'd for C$_{23}$H$_{25}$FN$_3$O$_5$: C, 65.24; H, 5.95; N, 9.92. Found: C, 64.97; H, 5.89; N, 9.90. $^1$H NMR(300 MHz, DMSO-d$_6$, δ): 7.30–7.15 (m, 6H), 7.10–7.00 (m, 4H), 6.03 (s, 2H), 3.92 (t, 2H, J=7 Hz), 3.60–3.00 (m, 10H), 2.20–2.05 (m, 2H). UV(MeOH): λmax 281 nm, ε6400. MS(CI, NH$_3$) m/e 308 (base, M+H$^+$). HRMS(CI, NH$_3$) m/e Calc'd for (M+H$^+$): 308.1763. Found: 308.1762.

EXAMPLE 21

2-(3-Phenylisoxazol-5-yl)Methyl-1,2,3,4-Tetrahydroisoquinoline (1:1) Maleic Acid Salt

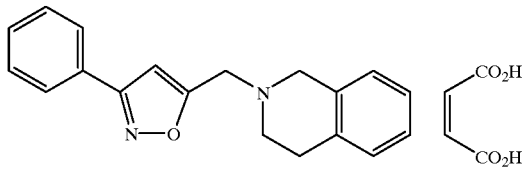

Part A: 2-(3-Phenylisoxazol-5-yl)Methyl-1,2,3,4-Tetrahydroisoquinoline (21A)

Prepared from 1,2,3,4-tetrahydroisoquinoline and 5-(bromomethyl)-3-phenylisoxazole under typical conditions. Purification by flash chromatography on silica gel 60, eluting with 25% EtOAc in hexane produced adduct 21A (81% yield). $^1$H NMR(300 MHz, CDCl$_3$, δ): 7.83–7.80 (m, 2H), 7.48–7.40 (m, 3H), 7.16–7.11 (m, 3H), 7.08–6.99 (m, 1H), 6.57 (s, 1H), 3.91 (s, 2H), 3.76 (s, 2H), 3.00–2.80 (m, 4H). $^{13}$C NMR(300 MHz, CDCl$_3$, δ): 170.25, 162.45, 134.04, 133.75, 129.97, 129.12, 128.92, 128.72, 126.81, 126.56, 126.36, 125.78, 101.26, 85.61, 53.20, 50.75, 29.03. MS(CI, NH$_3$) m/e 291 (base, M+H$^+$). HRMS(CI, NH$_3$) m/e Calc'd for (M+H$^+$): 291.1497. Found: 291.1512.

Part B: 2-(3-Phenylisoxazol-5-yl)Methyl-1,2,3,4-Tetrahydroisoquinoline (1:1) Maleic Acid Salt (21)

Standard method. Recrystallized from isopropanol. m.p. 190–192° C. UV (MeOH): λmax 240 nm, ε13,900. MS(CI, NH$_3$) m/e 308 (base, M+H$^+$+NH$_3$), 291 (98%, M+H$^+$). HRMS(EI) m/e Calc'd for (M+): 290.1419. Found: 290.1402.

EXAMPLE 22

(+/−)-2-((3-(4-Fluorophenyl)-2-Isoxazolin-5-yl)Methyl-1,2,3,4-Tetrahydroisoquinoline (1:1) Maleic Acid Salt

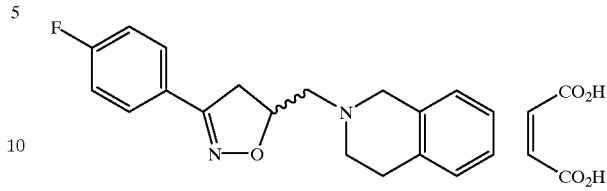

Part A: (+/−)-5-(Chloromethyl)-3-(4-Fluorophenyl)-2-Isoxazoline (22A).

Chlorox bleach (200 mL, ca. 140 mmol) was added dropwise over 20 min to a 0° C. solution of allyl chloride (5.7 mL, 70 mmol) and syn-4-fluorobenzaldoxime (10 g, 70 mmol) in CH$_2$Cl$_2$ (350 mL). After 15 min more, phases were separated. The aqueous layer was extracted with more CH$_2$Cl$_2$ (400 mL). The combined organic phases were extracted with H$_2$O (100 mL), dried (Na$_2$SO$_4$), filtered, and concentrated. The crude product was purified by flash chromatography, eluting with a gradient of hexane to 25% EtOAc in hexane to yield 22A (4.5 g) as a yellow solid after concentration. m.p. 60–62° C. $^1$H NMR(300 MHz, CDCl$_3$, δ): 7.71–7.64 (m, 2H), 7.15–7.07 (m, 2H), 5.05–4.96 (m, 1H), 3.71 (dd, 1H, J=11, 4 Hz), 3.59 (dd, 1H, J=11, 7 Hz), 3.50 (dd, 1H, J=17, 10 Hz), 3.34 (dd, 1H, J=17, 6 Hz). $^{13}$C NMR(300 MHz, CDCl$_3$, δ): 163.85 (d, J=250 Hz), 155.19, 128.73 (d, J=9 Hz), 125.37, 115.89 (d, J=22 Hz), 79.89, 44.89, 38.55. IR(KBr, cm$^{-1}$): 1604 (m-s), 1514 (s), 1232 (m-s), 838 (s). UV(MeOH): λmax 259 nm, ε15,0000. MS(H$_{20}$-GC/MS) m/e 214 (base, M+H$^+$, 1 Cl isotope pattern). HRMS(EI) m/e Calc'd for (M+): 213.0357. Found: 213.0355.

Part B: (+/−)-2-((3-(4-Fluorophenyl)-2-Isoxazolin-5-yl)Methyl-1,2,3,4-Tetrahydroisoquinoline (22B).

1,2,3,4-Tetrahydroisoquinoline was alkylated with chloride 22A in the usual way. The crude product was purified by flash chromatography on silica gel 60, eluting with 33% EtOAc in hexane to provide, after solvent 1 evaporation, amine 22B (55% yield) as a yellow solid. H NMR(300 MHz, CDCl$_3$, δ): 7.69–7.62 (m, 2H), 7.16–7.01 (m, 6H), 5.07–4.97 (m, 1H), 3.79–3.26 (m, 4H), 2.96–2.74 (m, 6H). $^{13}$C NMR(300 MHz, CDCl$_3$, δ): 163.72 (d, J=250 Hz), 155.64, 152.03, 150.32, 143.33, 134.34 (d, J=34 Hz), 128.70, 128.62, 126.41 (d, J=17 Hz), 125.71, 115.90 (d, J=22 Hz), 80.01, 61.22, 56.62, 51.63, 39.01, 29.01. IR(KBr, cm$^{-1}$): 1604 (s). UV(MeOH): xmax 319 nm, ε930; ‰max 261 nm, ε16,900. MS(CI, NH$_3$) m/e 311 (base, M+H$^+$). HRMS(CI, NH$_3$) m/e Calc'd for (M+H$^+$): 311.1560. Found: 311.1557.

Part C: (+/−)-2-((3-(4-Fluorophenyl)-2-Isoxazolin-5-yl)Methyl-1,2,3,4-Tetrahydroisoquinoline (1:1) Maleic Acid Salt (22)

Standard procedure. Recrystallized from isopropanol. m.p. 153–155° C. $^1$H NMR(300 MHz, CD$_3$OD, δ): 7.80–7.70 (m, 2H), 7.33–7.14 (m, 6H), 6.21 (s, 2H), 5,40–5.25 (m, 1H), 4.88 (br s, 2H), 4.53 (s, 2H), 3.80–3.65 (m, 3H), 3.60–3.45 (m, 2H), 3.30–3.20 (m, 3H). MS(CI, NH$_3$) m/e 311 (base, M+H$^+$). HRMS(CI, NH$_3$) m/e Calc'd for (M+H$^+$): 311.1560. Found: 311.1540.

EXAMPLE 23

1,3-Dihydro-2-((3-(4-Fluorophenoxy)Propyl)) Isoindole (1:1) Maleic Acid Salt.

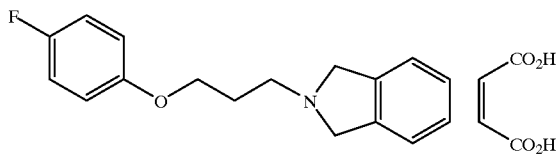

Part A: N-((3-(4-Fluorophenoxy)Propyl))Phthalimide (23A)

4-Fluorophenol (5.0 g, 45 mmol), N-(3-bromopropyl) phthalimide (12 g, 45 mmol), and $K_2CO_3$ (6.2 g, 45 mmol) were stirred in DMF (30 mL) for 14 h at RT under $N_2$. The mixture was then diluted with EtOAc, stirred with $MgSO_4$, filtered, and concentrated in vacuo. The product was purified by flash chromatography on silica gel 60, eluting with 20% EtOAc in hexane to yield, after solvent evaporation, imide 23A (10.7 g) as a colorless solid. m.p. 110–112° C. $^1$H NMR(300 MHz, $CDCl_3$, δ): 7.88–7.82 (m, 2H), 7.78–7.69 (mn, 2H), 6.96–6.88 (m, 2H), 6.78–6.71 (m, 2H), 3.99 (t, 2H, J=6 Hz), 3.91 (t, 2H, J=7 Hz), 2.17 (pentet, 2H, J=7 Hz). $^{13}$C NMR(300 MHz, $CDCl_3$, δ): 168.33, 157.20, 154.79, 133.92, 132.13, 123.21, 115.60, 115.41, 66.30, 35.42, 28.32. UV(MeOH): lmax 286 nm, e 3900; lmax 280 nm, e 4200; lmax 241 nm, e 12,300; lmax 219 nm, e 51,000. MS(CI, $NH_3$) m/e 317 (base, $M+H^++NH_3$), 300 (63%, $M+H^+$). HRMS(CI, $NH_3$) m/e Calc'd for $(M+H^+)$: 300.1036. Found: 300.1039.

Part B: 1,3-Dihydro-2-((3-(4-Fluorophenoxy)Propyl)) Isoindole (23B)

Imide 23A (5.0 g, 17 mmol) was reduced with $LiAlH_4$ (3.3 g, 86 mmol) in dry THF (400 mL) at reflux under $N_2$ overnight. After careful quenching with $Na_2SO_4.10H_2O$, the mixture was filtered through Celite, rinsed with more THF, and concentrated. The product was purified by flash chromatography on silica gel 60, eluting with a gradient of 20% to 50% EtOAc in hexane to yield, after solvent evaporation, amine 23B (3.1 g). $^1$H NMR(300 MHz, $CDCl_3$, δ): 7.20 (s, 4H), 7.00–6.80 (m, 4H), 4.05 (t, 2H, J=7 Hz), 3.95 (s, 4H), 2.91 (t, 2H, J=7 Hz), 2.15–2.00 (m, 2H). $^{13}$C NMR(300 MHz, $CDCl_3$, δ): 157.30, 155.19, 140.07, 126.72, 122.26, 115.60, 115.57, 66.74, 59.18, 52.67, 28.83. IR(KBr, $cm^{-1}$): 1206 (s). UV(MeOH): lmax 280 nin, e 2700; lmax 272 nm, e 2900. MS(CI, $CH_4$) m/e 272 (base, $M+H^+$).

Part C: 1,3-Dihydro-2-((3-(4-Fluorophenoxy)Propyl)) Isoindole (1:1) Maleic Acid Salt (23)

Standard procedure. m.p. 115–117° C. Elemental analysis. Calc'd for $C_2lH_{22}FNOS$: C, 65.11; H, 5.72; N, 3.63; F, 4.90. Found: C, 65.06; H, 5.60; N, 3.53; F, 5.00. $^1$H NMR(300 MHz, DMSO-$d_6$, δ): 7.43–7.35 (m, 4H), 7.20–7.10 (m, 2H), 7.00–6.95 (m, 2H), 6.03 (s, 2H), 4.07 (t, 2H, J=6 Hz), 3.49 (t, 2H, J=7 Hz), 3.40–3.30 (br s, 1H), 2.20–2.09 (m, 2H). $^{13}$C NMR(300 MHz, DMSO-$d_6$, δ): 167.78, 157.10, 155.00, 136.11, 135.05, 128.85, 123.34, 116.31, 116.20, 65.72, 58.47, 51.98, 25.82. IR(KBr, $cm^{-1}$): 2800–2350 (m, br), 1576 (s), 1206 (s). UV(MeOH): lmax 279 nm, e 2300; lmax 271 nm, e 2400. MS(CI, $NH_3$) m/e 272 (base, $M+H^+$). HRMS(CI, $NH_3$) m/e Calc'd for $(M+H^+)$: 272.1451. Found: 272.1443.

EXAMPLE 24

2-((3-(4-Fluorophenylthio)propyl))-1,2,3,4-Tetrahydroisoquinoline (1:1) Hydrochloride Salt.

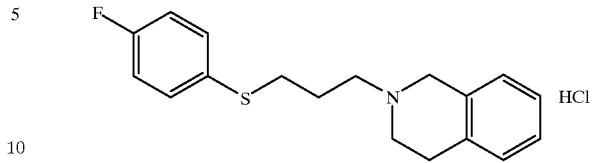

4-Fluorothiophenol (6.2 g, 48 mmol), 1-bromo-3-chloropropane (4.7 mL, 48 mmol), and powdered $K_2CO_3$ (3.5 g, 25 mmol) were stirred in DMF (25 mL) from 0° C. to RT overnight. The next morning, a small reaction aliquot was removed and extracted with EtOAc and 1 M HCl; the organic phase was evaporated and dried under vacuum, then analyzed by $^1$H NMR. The NMR spectrum indicated near quantitative conversion to 1-(4-fluorophenylthio)-3-chloropropane. $^1$H NMR(300 MHz, $CDCl_3$, δ): 7.40–7.33 (m, 2H), 7.05–6.97 (m, 2H), 3.65 (t, 2H, J=6 Hz), 3.02 (t, 2H, J=7 Hz), 2.03 (pentet, 2H, J=7 Hz).

Diisopropylethylamine (8.3 mL, 48 mmol), 1,2,3,4-tetrahydroisoquinoline (6.0 mL, 48 mmol), and NaI (0.75 g, 5 mmol) were added to the above reaction mixture containing the just made chlorosulfide. The resulting mixture was then heated to ca. 70° C. for 18 h, then to 90° C. for 4 h. After cooling, the mixture was extracted with EtOAc (lL) and 0.5 M NaOH (200 mL), then $H_{20}$(5×250 mL), finally brine (50 mL). The solution was dried ($Na_2SO_4$), filtered, and concentrated to yield crude amine 2-((3-(4-fluoro-phenylthio) propyl))-1,2,3,4-tetrahydroisoquinoline. This crude amine product was immediately converted to the salt by diluting with $CH_2Cl_2$ (50 mL) and adding 1 M HCl (75 mL). Diethyl ether was added, and the resulting salt precipitate was collected by filtration. Recrystallization from isopropanol produced salt 24 (9.3 g, 57% overall) of excellent purity. m.p. 171–173° C. Elemental analysis. Calc'd for $C_{18}H_{21}ClFNS$: C, 63.98; H, 6.26; N, 4.16; F, 5.62; Cl, 10.49; S, 9.49. Found: C, 63.70; H, 6.36; N, 4.13; F, 5.71; Cl, 10.22; S, 9.50. $^1$H NMR(300 MHz, $CD_3OD$, δ): 7.50–7.43 (m, 2H), 7.32–7.16 (m, 4H), 7.12–7.04 (m, 2H), 4.88 (br s, 1H), 4.43 (br s, 2H), 3.57 (br s, 2H), 3.43–3.38 (m, 2H), 3.17 (t, 2H, J=6 Hz), 3.03 (t, 2H, J=7 Hz), 2.16–2.06 (m, 2H). $^{13}$C NMR(300 MHz, $CD_3OD$, δ): 162.09 (d, J=246 Hz), 132.72 (d, J=8 Hz), 130.63, 130.24, 128.42, 128.06, 127.32, 126.86, 126.43, 115.77, 54.64, 52.86, 49.86, 31.20, 24.89, 23.53. IR(KBr, $cm^{-1}$): 2724–2418 (s, br), 1490 (s), 1222 (s), 822 (s), 756 (s). UV(MeOH): λmax 252 nm, ϵ6600. MS(CI, $NH_3$) m/e 302 (base, $M+H^+$). HRMS(CI, $NH_3$) m/e Calc'd for $(M+H^+)$: 302.1379. Found: 302.1383.

EXAMPLE 25

1,3-Dihydro-2-((3-(4-Fluorophenylthio) Propyl))Isoindole (1:1) Hydrochloride Salt

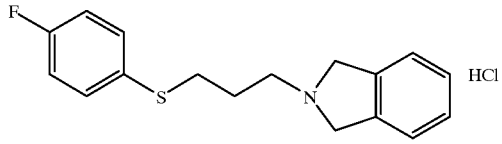

Part A: N-((3-(4-Fluorophenylthio)Propyl)Phthalimide (25A)

4-Fluorothiophenol (6.0 mL, 56 mmol), N-(3-bromopropyl)phthalimide (15 g, 56 mmol), and powdered K$_2$CO$_3$ (7.7 g, 56 mmol) were stirred in DMF (50 mL) at RT under N$_2$ for 29 h. Solvent was removed in vacuo, and the residue was extracted with EtOAc (1 L) and H$_{20}$ (5×200 mL), then brine (50 mL). The solution was dried (Na$_2$SO$_4$), filtered, and concentrated to yield sulfide imide 25A in quantitative yield as a crystalline solid. m.p. 73–75° C. Elemental analysis. Calc'd for C$_{17}$H$_{14}$FNO$_2$S: C, 64.75; H, 4.47; N, 4.44; F, 6.02; S, 10.17. Found: C, 64.73; H, 4.42; N, 4.37; F, 6.16; S, 9.90. $^1$H NMR(300 MHz, CDCl$_3$, δ): 7.88–7.81 (mn, 2H), 7.75–7.69 (m, 2H), 7.41–7.34 (m, 2H), 7.02–6.94 (in, 2H), 3.81 (t, 2H, J=7 Hz), 2.88 (t, 2H, J-7 Hz), 1.95 (pentet, 2H, J=7 Hz). $^{13}$C NMR(300 MHz, CDCl$_3$, δ): 168.23, 161.95 (d, J=247 Hz), 133.95, 133.11 (d, J=8 Hz), 132.03, 130.54, 123.20, 116.02, 36.86, 32.77, 28.07. IR(KBr, cm I): 1772 (w), 1712 (s). UV(MeOH): λmax 219 nin, ε78,000. MS(CI, NH$_3$) ml/e 333 (base, M+NH$_4^+$), 316 (45%, M+H$^+$). HRMS(CI, NH$_3$) ml/e Calc'd for (M+H$^+$): 316.0808. Found: 316.0795.

Part B: 1,3-Dihydro-2-((3-(4-Fluorophenylthio)Propyl)) Isoindole (25B)

Sulfide linide 25A (7.9 g, 25 rnmol) was reduced with BH$_3$-THF (0.7 M in THF, 100 inL, 70 mnmol) in dry THF (25 mL) under N$_2$ at RT for 2 days, then at ref lux for 2 days. After cooling, the excess borane was quenched by slow addition of MeOH (5OirL), then boiling for 1 h. After cooling and concentration in vacuo, 0.1 M HCl (200 inL) was added; the resulting mixture was stirred for 75 min at RT. The solution was basified by adding 1 M NaOH (50 rnL) and extracted with EtOAc (500 mL) plus brine (100 mL) to speed phase separation. The organic phase was then extracted with half-saturated brine (100 mL), dried (Na$_2$SO$_4$), filtered, and concentrated. Flash chromatographic purification on silica gel 60, eluting with hexane to 4:1 EtOAc/hexane provided, after solvent evaporation, amine 25B (4.04 g) as a tan solid. m.p. 58–63° C. Elemental analysis. Calcld for C$_{17}$H$_{18}$FNS: C, 71.05; H, 6.31; N, 4.87; F, 6.61; S, 11.16. Found: C, 70.93; H, 6.25; N, 4.85; F, 6.68; S, 10.95. $^1$H NMR(300 MHz, CDCl$_3$, δ): 7.37–7.31 (mn, 2H), 7.17 (s, 4H), 7.01–6.93 (m, 2H), 3.80 (s, 4H), 2.98 (t, 2H, J=7 Hz), 2.81 (t, 2H, J=7 Hz), 1.86 (pentet, 2H, J=7 Hz).1 C NMR(300 MHz, CDCl$_3$, δ) 161.71 (d, J=246 Hz), 140.02, 132.21 (d, J=8 Hz), 131.47, 126.74, 122.27, 115.99, (d, J=22 Hz), 59.08, 54.61,32.78, 28.52. IR(KBr, cm$^{-1}$): 1590 (w), 1490 (s), 1220 (m), 824 (m), 746 (m). UV (MeOH): λmax 253 nm, ε6900. MS(CI, NH$_3$) m/e 288 (base, M+H$^+$). HRMS(CI, NH$_3$) m/e Calc'd for (M+H$^+$): 288.1222. Found: 288.1216.

Part C: 1,3-Dihydro-2-((3-(4-Fluorophenylthio)Propyl)) Isoindole (1:1) Hydrochloride Salt (25)

The crude solid salt was prepared as described for Example 24. The salt was purified by boiling in benzene, decanting after slight cooling from a small amount of dark oily ppt. After cooling further and standing at RT, 25 (81% yield) was collected as off-white flakes. m.p. 125–1260. Elemental analysis. Calc'd for C$_{17}$H$_{19}$ClFNS: C, 63.05; H, 5.91; N, 4.32; Cl, 10.95; F, 5.88; S, 9.90. Found: C, 63.09; H, 5.85; N, 4.25; Cl, 11.05; F, 6.05; S, 9.66. $^1$H NMR(300 MHz, DMSO-d$_6$, δ): 12.43 (br s, 1H), 7.52–7.45 (m, 2H), 7.40–7.33 (m, 4H), 7.25–7.17 (m, 2H), 4.72 (br s, 2H), 4.49 (br s, 2H), 3.49–3.44 (m, 2H), 3.09 (t, 2H, J=7 Hz), 2.05 (pentet, 2H, J=7 Hz). $^{13}$C NMR(300 MHz, DMSO-d$_6$, δ): 161.43 (d, J=244 Hz), 134.81, 132.04 (d, J=8 Hz), 131.12, 128.75, 123.17, 116.52 (d, J=23 Hz), 57.90, 53.19, 30.91, 25.04. IR(KBr, cm$^{-1}$): 2632 (s), 2540 (m), 2382 (m), 1588 (m), 1490 (s), 1218 (m), 828 (m), 750 (m). UV(MeOH): λmax 252 nm, ε6600. MS(CI, NH$_3$) m/e 288 (base, M+H$^+$). HRMS(CI, NH$_3$) m/e Calc'd for (M+H$^+$): 288.1222. Found: 288.1220.

EXAMPLE 26

1,3-Dihydro-2-((3-(4-Fluorophenylsulfonyl) Propyl)) Isoindole (1:1) Maleic Acid Salt.

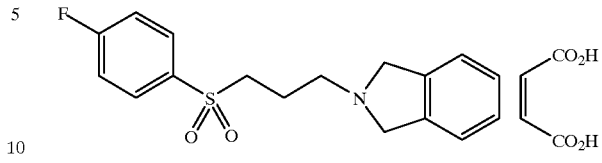

Part A: 1,3-Dihydro-2-((3-(4-Fluorophenylsulfonyl) Propyl))Isoindole (26A).

Sulfide amine-hydrochloride 25 (2.0 g, 6.2 mmol) was stirred with Oxone (2KHSO$_5$-KHSO$_4$-K$_2$SO$_4$, 7.62 g, 12.4 mmol) in MeOH at RT overnight. After concentration in vacuo the mixture was extracted with EtOAc (200 mL) and 1 _NaOH (100 mL), then H$_{20}$ (100 mL), finally brine (25 mL). The solution was dried (Na$_2$SO$_4$), filtered, and evaporated to yield the sulfone amine free base 26A (2.1 g). MS(ESI) m/e 320 (base, M+H$^+$).

Part B:1,3-Dihydro-2-((3-(4-Fluorophenylsulfonyl) Propyl))Isoindole (1:1) Maleic Acid Salt (26).

Standard method from crude 26A. Recrystallized from hot benzene/EtOH (2:1) to yield 26 as pale grey needles. m.p. 151–2° C. Elemental analysis. Calc'd for C$_{21}$H$_{22}$FNO$_6$S: C, 57.92; H, 5.09; N, 3.23; F, 4.36; S, 7.36. Found: C, 57.89; H, 4.96; N, 3.10; F, 4.48; S, 7.14. $^1$H NMR(300 MHz, DMSO-d$_6$, δ): 8.05–8.00 (m, 2H), 7.56 (t, 2H, J=9 Hz), 7.42–7.35 (m, 4H), 6.08 (s, 2H), 4.61 (br s, 4H), 3.52 (br t, 2H, J=8 Hz), 3.43 (br t, 2H, J=8 Hz), 2.07–1.97 (br pentet, 2H, J=9 Hz). $^{13}$C NMR(300 MHz, DMSO-d$_6$): 167.73, 165.64 (d, J=253 Hz), 135.84, 135.34, 135.18, 131.52 (d, J=10 Hz), 128.76, 123.19, 117.24, 58.39, 52.66, 52.26, 19.97. IR(KBr, cm$^{-1}$): 2800–2350 (m, br), 1702 (w), 1620 (m), 1588 (s), 1492 (s). UV(MeOH): λmax 270 nm, ε920; λmax 263 nm, ε1200; max 257 nm, 6 1300. MS(CI, NH$_3$) m/e 320 (base, M+H$^+$). HRMS(CI, NH$_3$) m/e Calc'd for (M+H$^+$): 320.1121. Found: 320.1136.

EXAMPLE 27

2-((3-(4-Fluorophenylsulfonyl)propyl))-1,2,3,4-Tetrahydroisoquinoline (1:1) Hydrochloride Salt.

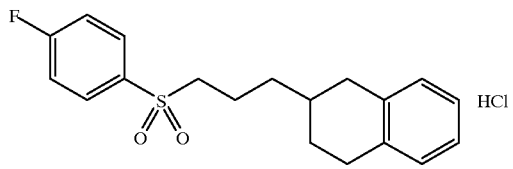

Sulfide 24 was treated with Oxone as in Example 26, Part A to provide the free base sulfone 27A (quantitative) as an orange-brown oil. The crude product was immediately converted to its hydrochloride salt in standard fashion. The salt was recrystallized from boiling isopropanol (4x) to upgrade to the desired purity. Yield 27 (34% overall) as a colorless solid. m.p. 212–215° C. $^1$H NMR(300 MHz, DMSO-d$_6$, δ): 10.90 (br s, 1H), 8.05–7.99 (m, 2H), 7.58–7.52 (m, 2H), 7.28–7.19 (m, 4H), 4.53–4.22 (m, 2H), 3.63–2.96 (m, 8H), 2.16–2.11 (m, 2H). $^{13}$C NMR(300 MHz, DMSO-d$_6$, δ): 165.61 (d, J=253 Hz), 135.48, 131.77, 131.52 (d, J=10 Hz), 128.91, 128.78, 128.02, 127.05, 117.23 (d, J=23 Hz), 53.61, 52.43, 52.06, 49.07, 25.14, 17.90. IR(KBr, cm$^{-1}$): 2900–2300 (s, br), 1588 (m), 1494 (s), 1144 (s). UV(MeOH): λmax 258 nm, ε590; )Lmax 252 nm, ε520. MS(ESI) m/e 334 (base, M+H$^+$). HRMS(CI, NH$_3$) m/e Calc'd for (M+H$^+$): 334.1277. Found: 334.1282.

EXAMPLE 28

2-((3-(3-Fluorophenylthio)propyl))-1,2,3,4-Tetrahydroisoquinoline (1:1) Hydrochloride Salt.

Prepared from 3-fluorothiophenol in analogous fashion to Example 24. The hydrochloride salt was recrystallized from isopropanol to yield a pale pink solid 28 (57% overall). m.p. 158–160° C. Elemental analysis. Calcld for $C_{19}H_{21}ClFNS$: C, 63.98; H, 6.26; Cl, 10.49; N, 4.16; F, 5.62; S, 9.49. Found: C, 63.67; H, 6.38; Cl, 10.35; N, 4.03; F, 5.51; S, 9.77. $^1$H NMR(300 MHz, DMSO-$d_6$, δ): 11.06 (br s, 1H), 7.41–7.00 (m, 8H), 4.53–4.48 (m, 1H), 4.30–4.22 (m, 1H), 3.72–3.60 (m, 1H), 3.34–2.96 (m, 7H), 2.14 (pentet, 2H, J=8 Hz). $^{13}$C NMR(300 MHz, DMSO-$d_6$, δ): 162.88 (d, J=246 Hz), 139.05 (d, J=7 Hz), 131.93, 131.24 (d, J=8 Hz), 128.92 (d, J=4 Hz), 127.89, 126.95, 124.15, 114.62 (d, J=23 Hz), 112.89 (d, J=21 Hz), 54.33, 51.87, 48.94, 29.41, 25.16, 23.41. IR(KBr, cm$^{-1}$): 2800–2400 (m-s, br), 1598 (m-s), 1576 (m-s), 1472 (s). UV(MeOH): λmax 253 nm, ε9650. MS(ESI) m/e 302 (base, M+H$^+$). HRMS(CI, NH$_3$) m/e Calc'd for (M+H$^+$): 302.1379. Found: 302.1379.

EXAMPLE 29

2-((3-(3-Fluorophenylsulfonyl)propyl))-1,2,3,4-Tetrahydroisoquinoline (1:1) Hydrochloride Salt.

Prepared from sulfide hydrochloride 28 as in Example 27 to yield 29 (45% overall) as an off-white solid after recrystallization (isopropanol). m.p. 171–173° C. Elemental analysis. Calc'd for $C_{19}H_{21}ClFNO_2S$: C, 58.45; H, 5.72; Cl, 9.58; N, 3.80; F, 5.15; S, 8.68. Found: C, 58.18; H, 5.82; Cl, 9.30; N, 3.71; F, 4.97; S, 8.63. $^1$H NMR(300 MHz, DMSO-$d_6$, δ): 11.01 (br s, 1H), 7.82–7.64 (m, 4H), 7.30–7.18 (m, 4H), 4.53–4.48 (m, 1H), 4.30–4.22 (m, 1H), 3.70–3.57 (m, 3H), 3.27–3.15 (m, 4H), 3.06–2.85 (m, 1H), 2.18–2.10 (m, 2H). $^{13}$C NMR(300 MHz, DMSO-$d_6$, δ): 162.26 (d, J=249 Hz), 141.15 (d, J=6 Hz), 132.43 (d, J=7 Hz), 131.86, 128.88, 128.83, 127.91, 126.96, 124.53, 121.73 (d, J=21 Hz), 115.35 (d, J=24 Hz), 53.52, 52.20, 51.81, 48.88, 25.09, 17.71. IR(KBr, cm$^{-1}$): 2724–2400 (m-s, br), 1594 (m), 1138 (s). UV(MeOH): λmax 275 nm, c 17,400; λmax 268 nm, ε20,800. MS(ESI) m/e 334 (base, M+H$^+$). HRMS(CI, NH$_3$) m/e Calc'd for (M+H$^+$): 334.1277. Found: 334.1266.

EXAMPLE 30

2-((1-(4-Fluorophenylsulfonyl)-4-Piperidyl))-1,2,3,4-Tetrahydroisoquinoline (1:1) Hydrochloride Salt.

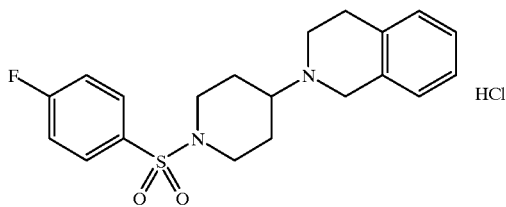 HCl

Part A: 1-(4-Fluorophenylsulfonyl)-4-Oxopiperidine (30A).

4-Piperidone-HCl Hydrate (8.0 g, 52 mmol), 4-Fluorobenzenesulfonyl Chloride (10 g, 52 mmol), and 1.0 M NaOH (120 mL) were stirred in THF (200 mL) from 0° C to RT overnight. After phase separation, the aqueous layer was extracted further with EtOAc (1 L). The combined organic phases were extracted with 1 _HCl (180 mL), H$_{2O}$ (100 mL), and brine (50 mL). The solution was dried (Na$_2$SO$_4$), filtered, and concentrated in vacuo to yield sulfonamide 30A (12.1 g) as a pale yellow solid. MS(GC-MS, H$_{2O}$) m/e 258 (base, M+H$^+$), 188 (13%). HRMS(CI, NH$_3$) m/e Calc'd for (M+H$^+$): 258.0600. Found: 258.0601.

Part B: 2-((1-(4-Fluorophenylsulfonyl)-4-Piperidyl))-1,2,3,4-Tetrahydroisoquinoline (1:1) Hydrochloride Salt (30).

Crude ketone 30A (6.0 g, 23 mmol) and titanium (IV) isopropoxide (8.5 mL, 29 mmol) were stirred at RT under N$_2$ for 1 h. Absolute EtOH (25 mL) and sodium cyanoborohydride (0.97 g, 15 mmol) were added, and the resulting mixture was stirred overnight. More NaBH$_3$CN (1.0 g) was added, and stirring was continued for 1 h. The reaction was quenched with 1 M NaOH (5 mL), filtered through a Celite pad, and rinsed well with MeOH. After concentration, the product was purified by flash chromatography on silica gel 60, eluting with hexane to 9:1 EtOAc/hexane to yield the free base amine (1.7 g) as a pale yellow solid. Hydrochloride salt formation as usual, followed by recrystallization from MeOH afforded salt 30 (1.0 g) as a colorless solid. m.p.>240°. Elemental analysis. Calc'd for $C_{20}H_{24}ClFN_2O_2S$: C, 58.46; H, 5.90; Cl, 8.64; N, 6.83; F, 4.62; S, 7.80. Found: C, 58.48; H, 5.93; Cl, 8.30; N, 6.80; F, 4.33; S, 7.44. $^1$H NMR(300 MHz, DMSO-$d_6$, δ): 11.70 (br s, 1H), 7.88–7.82 (m, 2H), 7.56–7.49 (m, 2H), 7.27–7.17 (m, 4H), 4.40–4.30 (m, 2H), 3.82–3.78 (m, 3H), 3.67–3.59 (m, 1H), 3.40–3.22 (m, 2H), 3.02–2.94 (m, 1H), 2.33–2.20 (m, 4H), 1.96–1.81 (m, 2H). $^{13}$C NMR(300 MHz, DMSO-$d_6$, δ): 165.16 (d, J=251 Hz), 132.20, 131.93, 131.06, (d, J=10 Hz), 129.01, 128.80, 127.92, 127.13, 126.95, 117.12 (d, J=23 Hz), 60.58, 48.84, 46.35, 45.16, 25.93, 25.40. IR(KBr, cm$^{-1}$): 2800–2300 (m, br), 1592 (m), 1328 (m), 1170 (s). UV(MeOH): λmax 225 nm, 9 10,000. MS(ESI) m/e 375 (base, M+H$^+$). HRMS(CI, NH$_3$) m/e Calc'd for (M+H$^+$): 375.1543. Found: 375.1525.

The following tables contain examples of the present invention. The values of p and q are taken to be 1–3. When no substitution is desired, $R^{1a}$ and $R^5$ are designated as hydrogen.

TABLE 1

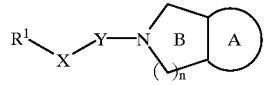

| Ex | $R^1$ | X | Y | n | B + A | MS |
|---|---|---|---|---|---|---|
| 1 | 4-fluorophenyl | 1,3-dioxolan-2-yl | n-propyl | 1 | 1,3-dihydroisoindole | 328 |

TABLE 1-continued

| Ex | R¹ | X | Y | n | B + A | MS |
|---|---|---|---|---|---|---|
| 2 | 4-bromo-phenyl | 1,3-dioxolan-2-yl | n-propyl | 1 | 1,3-dihydro-isoindole | 390.1 |
| 3 | 4-methyl-phenyl | 1,3-dioxolan-2-yl | n-propyl | 1 | 1,3-dihydro-isoindole | 324.2 |
| 4 | 4-fluoro-phenyl | 1,3-dioxolan-2-yl | n-propyl | 2 | 1,2,3,4-tetrahydro-iso-quinoline | 342.2 |
| 5 | 4-fluoro-phenyl | —C(=O)— | n-propyl | 1 | 1,3-dihydro-isoindole | 284.1 |
| 9 | 4-fluoro-phenyl | —CH(OH)— | n-propyl | 1 | 1,3-dihydro-isoindole | 286.2 |
| 10 | 4-fluoro-phenyl | —CH(OAc)— | n-propyl | 1 | 1,3-dihydro-isoindole | 328.2 |
| 11 | 4-fluoro-phenyl | —C(=O)— | n-propyl | 2 | 1,2,3,4-tetrahydro-iso-quinoline | 298.2 |
| 12 | 4-fluoro-phenyl | —C(=O)— | n-propyl | 1 | 1,3-dihydro-benz[f]isoindole | 334.2 |
| 13 | 4-pyridyl | —C(=O)— | n-propyl | 2 | 1,2,3,4-tetrahydro-iso-quinoline | 281.2 |
| 14 | 3-fluoro-phenyl | —C(=O)— | n-propyl | 2 | 1,2,3,4-tetrahydro-iso-quinoline | 298.2 |
| 15 | 3-fluoro-phenyl | —C(=O)— | n-propyl | 1 | 1,3-dihydro-isoindole | 283.1 |
| 16 | 4-fluoro-phenyl | —C(=O)— | n-propyl | 2 | 1,3-dihydro-benz[de]isoindole | 333.2 |
| 17 | 2-thienyl | —C(=O)— | n-propyl | 2 | 1,2,3,4-tetrahydro-iso-quinoline | 286.1 |
| 18 | 4-fluoro-phenyl | —C(=O)— | n-propyl | 2 | 6,7-dimethoxy-1,2,3,4-tetrahydro-iso-quinoline | 358.2 |
| 19 | 4-fluoro-phenyl | —C(=O)— | n-propyl | 2 | (+/−)-trans perhydro-iso-quinoline | 304.2 |
| 20 | 1,3-Dihydro-2H-benzimidazol-2-one)-1-yl | | n-propyl | 2 | 1,2,3,4-tetrahydro-iso-quinoline | 308.2 |
| 21 | 3-phenyl-isoxazol-5-yl | —CH₂— | | 2 | 1,2,3,4-tetrahydro-iso-quinoline | 290.1 |
| 22 | 3-(4-Fluorophenyl)-2-isoxazolin-5-yl | —CH₂— | | 2 | 1,2,3,4-tetrahydro-iso-quinoline | 311.2 |
| 23 | 4-fluoro-phenyl | —O— | n-propyl | 1 | 1,3-dihydro-isoindole | 272.1 |
| 24 | 4-fluoro-phenyl | —S— | n-propyl | 2 | 1,2,3,4-tetrahydro-iso-quinoline | 302.1 |
| 25 | 4-fluoro-phenyl | —S— | n-propyl | 1 | 1,3-dihydro-isoindole | 288.1 |

TABLE 1-continued
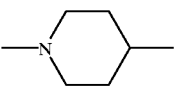
| Ex | R¹ | X | Y | n | B + A | MS |
|---|---|---|---|---|---|---|
| 26 | 4-fluoro-phenyl | —SO₂— | n-propyl | 1 | 1,3-dihydro-isoindole | 320.1 |
| 27 | 4-fluoro-phenyl | —SO₂— | n-propyl | 2 | 1,2,3,4-tetrahydro-iso-quinoline | 334.1 |
| 28 | 3-fluoro-phenyl | —S— | n-propyl | 2 | 1,2,3,4-tetrahydro-iso-quinoline | 302.1 |
| 29 | 3-fluoro-phenyl | —SO₂— | n-propyl | 2 | 1,2,3,4-tetrahydro-iso-quinoline | 334.1 |
| 30 | 4-fluoro-phenyl | —SO₂— | (N-methylpiperidinyl) | 2 | 1,2,3,4-tetrahydro-iso-quinoline | 375.2 |
TABLE 2
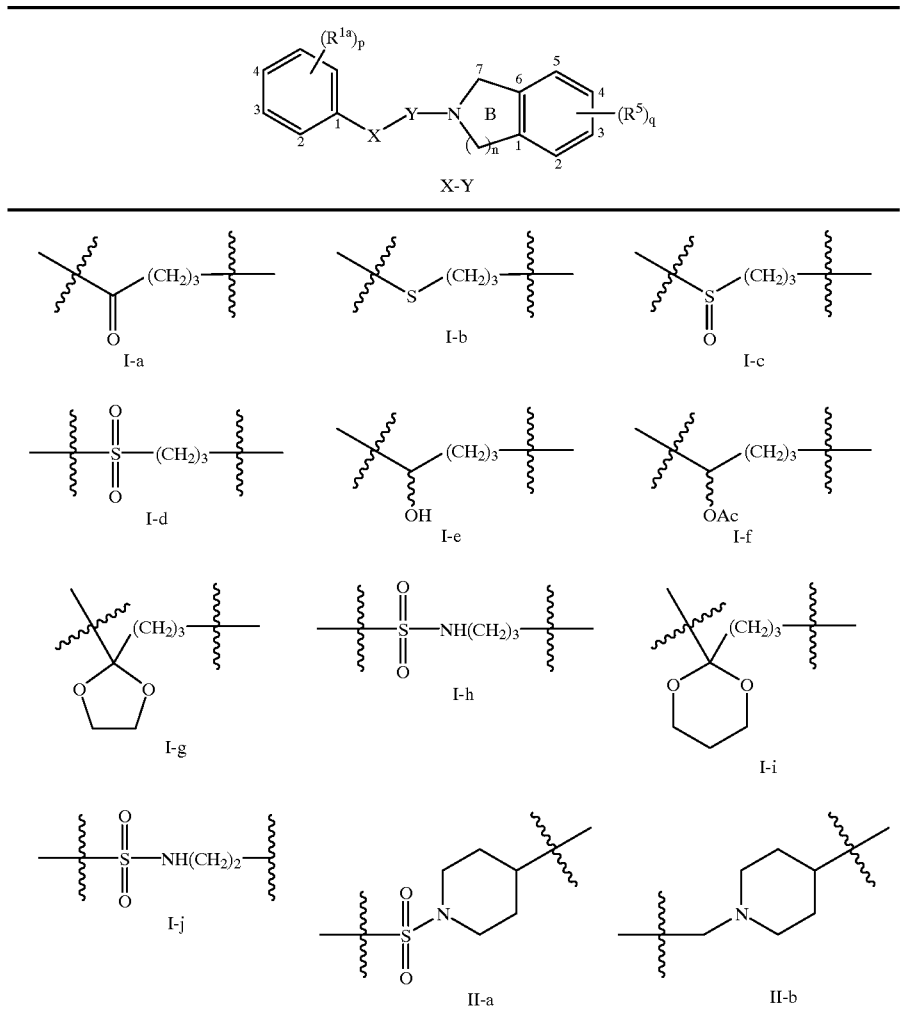

TABLE 2-continued

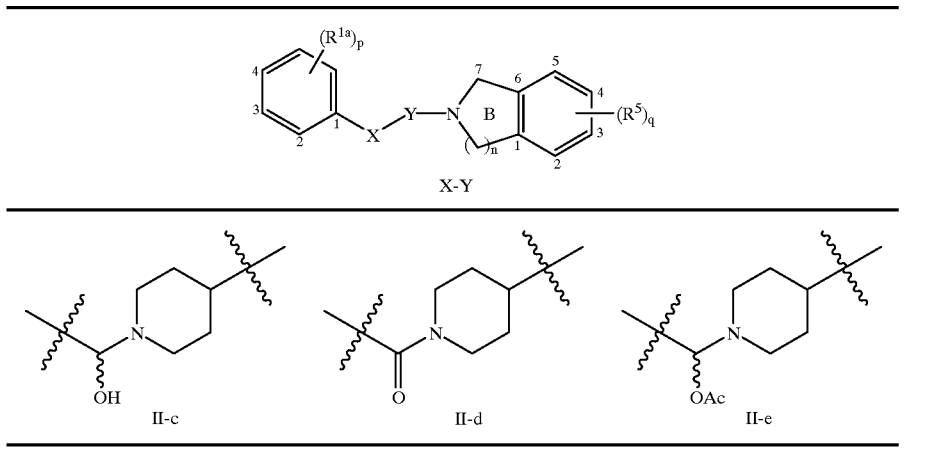

| Ex. # | $R^{1a}$ | n | $R^5$ |
|---|---|---|---|
| 1 | H | 1 | 2-CH$_3$ |
| 2 | H | 1 | 3-CH$_3$ |
| 3 | H | 1 | 2-CH$_2$CH$_3$ |
| 4 | H | 1 | 3-CH$_2$CH$_3$ |
| 5 | H | 1 | 2-CH$_2$CH$_2$CH$_3$ |
| 6 | H | 1 | 3-CH$_2$CH$_2$CH$_3$ |
| 7 | H | 1 | 2-isopropyl |
| 8 | H | 1 | 3-isopropyl |
| 9 | H | 1 | 2-butyl |
| 10 | H | 1 | 3-butyl |
| 11 | H | 1 | 2-isobutyl |
| 12 | H | 1 | 3-isobutyl |
| 13 | H | 1 | 2-t-butyl |
| 14 | H | 1 | 3-t-butyl |
| 15 | H | 1 | 2-Cl |
| 16 | H | 1 | 3-Cl |
| 17 | H | 1 | 2-F |
| 18 | H | 1 | 3-F |
| 19 | H | 1 | 2-Br |
| 20 | H | 1 | 3-Br |
| 21 | H | 1 | 2-OCH$_3$ |
| 22 | H | 1 | 3-OCH$_3$ |
| 23 | H | 1 | 2,3-CH$_3$ |
| 24 | H | 1 | 2,4-CH$_3$ |
| 25 | H | 1 | 2,5-CH$_3$ |
| 26 | H | 1 | 3,4-CH$_3$ |
| 27 | H | 1 | 2,3-Cl |
| 28 | H | 1 | 2,4-Cl |
| 29 | H | 1 | 2,5-Cl |
| 30 | H | 1 | 3,4-Cl |
| 31 | H | 1 | 2,3-F |
| 32 | H | 1 | 2,4-F |
| 33 | H | 1 | 2,5-F |
| 34 | H | 1 | 3,4-F |
| 35 | H | 1 | 2,3-Br |
| 36 | H | 1 | 2,4-Br |
| 37 | H | 1 | 2,5-Br |
| 38 | H | 1 | 3,4-Br |
| 39 | H | 1 | 2,3-OCH$_3$ |
| 40 | H | 1 | 2,4-OCH$_3$ |
| 41 | H | 1 | 2,5-OCH$_3$ |
| 42 | H | 1 | 3,4-OCH$_3$ |
| 43 | 4-F | 1 | 2-CH$_3$ |
| 44 | 4-F | 1 | 3-CH$_3$ |
| 45 | 4-F | 1 | 2-CH$_2$CH$_3$ |
| 46 | 4-F | 1 | 3-CH$_2$CH$_3$ |
| 47 | 4-F | 1 | 2-CH$_2$CH$_2$CH$_3$ |
| 48 | 4-F | 1 | 3-CH$_2$CH$_2$CH$_3$ |
| 49 | 4-F | 1 | 2-isopropyl |
| 50 | 4-F | 1 | 3-isopropyl |
| 51 | 4-F | 1 | 2-butyl |
| 52 | 4-F | 1 | 3-butyl |
| 53 | 4-F | 1 | 2-isobutyl |
| 54 | 4-F | 1 | 3-isobutyl |
| 55 | 4-F | 1 | 2-t-butyl |
| 56 | 4-F | 1 | 3-t-butyl |
| 57 | 4-F | 1 | 2-Cl |
| 58 | 4-F | 1 | 3-Cl |
| 59 | 4-F | 1 | 2-F |
| 60 | 4-F | 1 | 3-F |
| 61 | 4-F | 1 | 2-Br |
| 62 | 4-F | 1 | 3-Br |
| 63 | 4-F | 1 | 2-OCH$_3$ |
| 64 | 4-F | 1 | 3-OCH$_3$ |
| 65 | 4-F | 1 | 2,3-CH$_3$ |
| 66 | 4-F | 1 | 2,4-CH$_3$ |
| 67 | 4-F | 1 | 2,5-CH$_3$ |
| 68 | 4-F | 1 | 3,4-CH$_3$ |
| 69 | 4-F | 1 | 2,3-Cl |
| 70 | 4-F | 1 | 2,4-Cl |
| 71 | 4-F | 1 | 2,5-Cl |
| 72 | 4-F | 1 | 3,4-Cl |
| 73 | 4-F | 1 | 2,3-F |
| 74 | 4-F | 1 | 2,4-F |
| 75 | 4-F | 1 | 2,5-F |
| 76 | 4-F | 1 | 3,4-F |
| 77 | 4-F | 1 | 2,3-Br |
| 78 | 4-F | 1 | 2,4-Br |
| 79 | 4-F | 1 | 2,5-Br |
| 80 | 4-F | 1 | 3,4-Br |
| 81 | 4-F | 1 | 2,3-OCH$_3$ |
| 82 | 4-F | 1 | 2,4-OCH$_3$ |
| 83 | 4-F | 1 | 2,5-OCH$_3$ |
| 84 | 4-F | 1 | 3,4-OCH$_3$ |
| 85 | 3-F | 1 | 2-CH$_3$ |
| 86 | 3-F | 1 | 3-CH$_3$ |
| 87 | 3-F | 1 | 2-CH$_2$CH$_3$ |
| 88 | 3-F | 1 | 3-CH$_2$CH$_3$ |
| 89 | 3-F | 1 | 2-CH$_2$CH$_2$CH$_3$ |
| 90 | 3-F | 1 | 3-CH$_2$CH$_2$CH$_3$ |
| 91 | 3-F | 1 | 2-isopropyl |
| 92 | 3-F | 1 | 3-isopropyl |
| 93 | 3-F | 1 | 2-butyl |
| 94 | 3-F | 1 | 3-butyl |
| 95 | 3-F | 1 | 2-isobutyl |
| 96 | 3-F | 1 | 3-isobutyl |
| 97 | 3-F | 1 | 2-t-butyl |
| 98 | 3-F | 1 | 3-t-butyl |
| 99 | 3-F | 1 | 2-Cl |
| 100 | 3-F | 1 | 3-Cl |
| 101 | 3-F | 1 | 2-F |
| 102 | 3-F | 1 | 3-F |

-continued

| Ex. # | $R^{1a}$ | n | $R^5$ |
|---|---|---|---|
| 103 | 3-F | 1 | 2-Br |
| 104 | 3-F | 1 | 3-Br |
| 105 | 3-F | 1 | 2-OCH$_3$ |
| 106 | 3-F | 1 | 3-OCH$_3$ |
| 107 | 3-F | 1 | 2,3-CH$_3$ |
| 108 | 3-F | 1 | 2,4-CH$_3$ |
| 109 | 3-F | 1 | 2,5-CH$_3$ |
| 110 | 3-F | 1 | 3,4-CH$_3$ |
| 111 | 3-F | 1 | 2,3-Cl |
| 112 | 3-F | 1 | 2,4-Cl |
| 113 | 3-F | 1 | 2,5-Cl |
| 114 | 3-F | 1 | 3,4-Cl |
| 115 | 3-F | 1 | 2,3-F |
| 116 | 3-F | 1 | 2,4-F |
| 117 | 3-F | 1 | 2,5-F |
| 118 | 3-F | 1 | 3,4-F |
| 119 | 3-F | 1 | 2,3-Br |
| 120 | 3-F | 1 | 2,4-Br |
| 121 | 3-F | 1 | 2,5-Br |
| 122 | 3-F | 1 | 3,4-Br |
| 123 | 3-F | 1 | 2,3-OCH$_3$ |
| 124 | 3-F | 1 | 2,4-OCH$_3$ |
| 125 | 3-F | 1 | 2,5-OCH$_3$ |
| 126 | 3-F | 1 | 3,4-OCH$_3$ |
| 127 | 2,3-F | 1 | 2-CH$_3$ |
| 128 | 2,3-F | 1 | 3-CH$_3$ |
| 129 | 2,3-F | 1 | 2-CH$_2$CH$_3$ |
| 130 | 2,3-F | 1 | 3-CH$_2$CH$_3$ |
| 131 | 2,3-F | 1 | 2-CH$_2$CH$_2$CH$_3$ |
| 132 | 2,3-F | 1 | 3-CH$_2$CH$_2$CH$_3$ |
| 133 | 2,3-F | 1 | 2-isopropyl |
| 134 | 2,3-F | 1 | 3-isopropyl |
| 135 | 2,3-F | 1 | 2-butyl |
| 136 | 2,3-F | 1 | 3-butyl |
| 137 | 2,3-F | 1 | 2-isobutyl |
| 138 | 2,3-F | 1 | 3-isobutyl |
| 139 | 2,3-F | 1 | 2-t-butyl |
| 140 | 2,3-F | 1 | 3-t-butyl |
| 141 | 2,3-F | 1 | 2-Cl |
| 142 | 2,3-F | 1 | 3-Cl |
| 143 | 2,3-F | 1 | 2-F |
| 144 | 2,3-F | 1 | 3-F |
| 145 | 2,3-F | 1 | 2-Br |
| 146 | 2,3-F | 1 | 3-Br |
| 147 | 2,3-F | 1 | 2-OCH$_3$ |
| 148 | 2,3-F | 1 | 3-OCH$_3$ |
| 149 | 2,3-F | 1 | 2,3-CH$_3$ |
| 150 | 2,3-F | 1 | 2,4-CH$_3$ |
| 151 | 2,3-F | 1 | 2,5-CH$_3$ |
| 152 | 2,3-F | 1 | 3,4-CH$_3$ |
| 153 | 2,3-F | 1 | 2,3-Cl |
| 154 | 2,3-F | 1 | 2,4-Cl |
| 155 | 2,3-F | 1 | 2,5-Cl |
| 156 | 2,3-F | 1 | 3,4-Cl |
| 157 | 2,3-F | 1 | 2,3-F |
| 158 | 2,3-F | 1 | 2,4-F |
| 159 | 2,3-F | 1 | 2,5-F |
| 160 | 2,3-F | 1 | 3,4-F |
| 161 | 2,3-F | 1 | 2,3-Br |
| 162 | 2,3-F | 1 | 2,4-Br |
| 163 | 2,3-F | 1 | 2,5-Br |
| 164 | 2,3-F | 1 | 3,4-Br |
| 165 | 2,3-F | 1 | 2,3-OCH$_3$ |
| 166 | 2,3-F | 1 | 2,4-OCH$_3$ |
| 167 | 2,3-F | 1 | 2,5-OCH$_3$ |
| 168 | 2,3-F | 1 | 3,4-OCH$_3$ |
| 169 | 3,4-F | 1 | 2-CH$_3$ |
| 170 | 3,4-F | 1 | 3-CH$_3$ |
| 171 | 3,4-F | 1 | 2-CH$_2$CH$_3$ |
| 172 | 3,4-F | 1 | 3-CH$_2$CH$_3$ |
| 173 | 3,4-F | 1 | 2-CH$_2$CH$_2$CH$_3$ |
| 174 | 3,4-F | 1 | 3-CH$_2$CH$_2$CH$_3$ |
| 175 | 3,4-F | 1 | 2-isopropyl |
| 176 | 3,4-F | 1 | 3-isopropyl |
| 177 | 3,4-F | 1 | 2-butyl |
| 178 | 3,4-F | 1 | 3-butyl |
| 179 | 3,4-F | 1 | 2-isobutyl |
| 180 | 3,4-F | 1 | 3-isobutyl |
| 181 | 3,4-F | 1 | 2-t-butyl |
| 182 | 3,4-F | 1 | 3-t-butyl |
| 183 | 3,4-F | 1 | 2-Cl |
| 184 | 3,4-F | 1 | 3-Cl |
| 185 | 3,4-F | 1 | 2-F |
| 186 | 3,4-F | 1 | 3-F |
| 187 | 3,4-F | 1 | 2-Br |
| 188 | 3,4-F | 1 | 3-Br |
| 189 | 3,4-F | 1 | 2-OCH$_3$ |
| 190 | 3,4-F | 1 | 3-OCH$_3$ |
| 191 | 3,4-F | 1 | 2,3-CH$_3$ |
| 192 | 3,4-F | 1 | 2,4-CH$_3$ |
| 193 | 3,4-F | 1 | 2,5-CH$_3$ |
| 194 | 3,4-F | 1 | 3,4-CH$_3$ |
| 195 | 3,4-F | 1 | 2,3-Cl |
| 196 | 3,4-F | 1 | 2,4-Cl |
| 197 | 3,4-F | 1 | 2,5-Cl |
| 198 | 3,4-F | 1 | 3,4-Cl |
| 199 | 3,4-F | 1 | 2,3-F |
| 200 | 3,4-F | 1 | 2,4-F |
| 201 | 3,4-F | 1 | 2,5-F |
| 202 | 3,4-F | 1 | 3,4-F |
| 203 | 3,4-F | 1 | 2,3-Br |
| 204 | 3,4-F | 1 | 2,4-Br |
| 205 | 3,4-F | 1 | 2,5-Br |
| 206 | 3,4-F | 1 | 3,4-Br |
| 207 | 3,4-F | 1 | 2,3-OCH$_3$ |
| 208 | 3,4-F | 1 | 2,4-OCH$_3$ |
| 209 | 3,4-F | 1 | 2,5-OCH$_3$ |
| 210 | 3,4-F | 1 | 3,4-OCH$_3$ |
| 211 | 4-Cl | 1 | 2-CH$_3$ |
| 212 | 4-Cl | 1 | 3-CH$_3$ |
| 213 | 4-Cl | 1 | 2-CH$_2$CH$_3$ |
| 214 | 4-Cl | 1 | 3-CH$_2$CH$_3$ |
| 215 | 4-Cl | 1 | 2-CH$_2$CH$_2$CH$_3$ |
| 216 | 4-Cl | 1 | 3-CH$_2$CH$_2$CH$_3$ |
| 217 | 4-Cl | 1 | 2-isopropyl |
| 218 | 4-Cl | 1 | 3-isopropyl |
| 219 | 4-Cl | 1 | 2-butyl |
| 220 | 4-Cl | 1 | 3-butyl |
| 221 | 4-Cl | 1 | 2-isobutyl |
| 222 | 4-Cl | 1 | 3-isobutyl |
| 223 | 4-Cl | 1 | 2-t-butyl |
| 224 | 4-Cl | 1 | 3-t-butyl |
| 225 | 4-Cl | 1 | 2-Cl |
| 226 | 4-Cl | 1 | 3-Cl |
| 227 | 4-Cl | 1 | 2-F |
| 228 | 4-Cl | 1 | 3-F |
| 229 | 4-Cl | 1 | 2-Br |
| 230 | 4-Cl | 1 | 3-Br |
| 231 | 4-Cl | 1 | 2-OCH$_3$ |
| 232 | 4-Cl | 1 | 3-OCH$_3$ |
| 233 | 4-Cl | 1 | 2,3-CH$_3$ |
| 234 | 4-Cl | 1 | 2,4-CH$_3$ |
| 235 | 4-Cl | 1 | 2,5-CH$_3$ |
| 236 | 4-Cl | 1 | 3,4-CH$_3$ |
| 237 | 4-Cl | 1 | 2,3-Cl |
| 238 | 4-Cl | 1 | 2,4-Cl |
| 239 | 4-Cl | 1 | 2,5-Cl |
| 240 | 4-Cl | 1 | 3,4-Cl |
| 241 | 4-Cl | 1 | 2,3-F |
| 242 | 4-Cl | 1 | 2,4-F |
| 243 | 4-Cl | 1 | 2,5-F |
| 244 | 4-Cl | 1 | 3,4-F |
| 245 | 4-Cl | 1 | 2,3-Br |
| 246 | 4-Cl | 1 | 2,4-Br |
| 247 | 4-Cl | 1 | 2,5-Br |
| 248 | 4-Cl | 1 | 3,4-Br |
| 249 | 4-Cl | 1 | 2,3-OCH$_3$ |
| 250 | 4-Cl | 1 | 2,4-OCH$_3$ |
| 251 | 4-Cl | 1 | 2,5-OCH$_3$ |
| 252 | 4-Cl | 1 | 3,4-OCH$_3$ |
| 253 | 3-Cl | 1 | 2-CH$_3$ |
| 254 | 3-Cl | 1 | 3-CH$_3$ |
| 255 | 3-Cl | 1 | 2-CH$_2$CH$_3$ |
| 256 | 3-Cl | 1 | 3-CH$_2$CH$_3$ |

-continued

| Ex. # | R¹ᵃ | n | R⁵ |
|---|---|---|---|
| 257 | 3-Cl | 1 | 2-CH₂CH₂CH₃ |
| 258 | 3-Cl | 1 | 3-CH₂CH₂CH₃ |
| 259 | 3-Cl | 1 | 2-isopropyl |
| 260 | 3-Cl | 1 | 3-isopropyl |
| 261 | 3-Cl | 1 | 2-butyl |
| 262 | 3-Cl | 1 | 3-butyl |
| 263 | 3-Cl | 1 | 2-isobutyl |
| 264 | 3-Cl | 1 | 3-isobutyl |
| 265 | 3-Cl | 1 | 2-t-butyl |
| 266 | 3-Cl | 1 | 3-t-butyl |
| 267 | 3-Cl | 1 | 2-Cl |
| 268 | 3-Cl | 1 | 3-Cl |
| 269 | 3-Cl | 1 | 2-F |
| 270 | 3-Cl | 1 | 3-F |
| 271 | 3-Cl | 1 | 2-Br |
| 272 | 3-Cl | 1 | 3-Br |
| 273 | 3-Cl | 1 | 2-OCH₃ |
| 274 | 3-Cl | 1 | 3-OCH₃ |
| 275 | 3-Cl | 1 | 2,3-CH₃ |
| 276 | 3-Cl | 1 | 2,4-CH₃ |
| 277 | 3-Cl | 1 | 2,5-CH₃ |
| 278 | 3-Cl | 1 | 3,4-CH₃ |
| 279 | 3-Cl | 1 | 2,3-Cl |
| 280 | 3-Cl | 1 | 2,4-Cl |
| 281 | 3-Cl | 1 | 2,5-Cl |
| 282 | 3-Cl | 1 | 3,4-Cl |
| 283 | 3-Cl | 1 | 2,3-F |
| 284 | 3-Cl | 1 | 2,4-F |
| 285 | 3-Cl | 1 | 2,5-F |
| 286 | 3-Cl | 1 | 3,4-F |
| 287 | 3-Cl | 1 | 2,3-Br |
| 288 | 3-Cl | 1 | 2,4-Br |
| 289 | 3-Cl | 1 | 2,5-Br |
| 290 | 3-Cl | 1 | 3,4-Br |
| 291 | 3-Cl | 1 | 2,3-OCH₃ |
| 292 | 3-Cl | 1 | 2,4-OCH₃ |
| 293 | 3-Cl | 1 | 2,5-OCH₃ |
| 294 | 3-Cl | 1 | 3,4-OCH₃ |
| 295 | 3-CF₃ | 1 | 2-CH₃ |
| 296 | 3-CF₃ | 1 | 3-CH₃ |
| 297 | 3-CF₃ | 1 | 2-CH₂CH₃ |
| 298 | 3-CF₃ | 1 | 3-CH₂CH₃ |
| 299 | 3-CF₃ | 1 | 2-CH₂CH₂CH₃ |
| 300 | 3-CF₃ | 1 | 3-CH₂CH₂CH₃ |
| 301 | 3-CF₃ | 1 | 2-isopropyl |
| 302 | 3-CF₃ | 1 | 3-isopropyl |
| 303 | 3-CF₃ | 1 | 2-butyl |
| 304 | 3-CF₃ | 1 | 3-butyl |
| 305 | 3-CF₃ | 1 | 2-isobutyl |
| 306 | 3-CF₃ | 1 | 3-isobutyl |
| 307 | 3-CF₃ | 1 | 2-t-butyl |
| 308 | 3-CF₃ | 1 | 3-t-butyl |
| 309 | 3-CF₃ | 1 | 2-Cl |
| 310 | 3-CF₃ | 1 | 3-Cl |
| 311 | 3-CF₃ | 1 | 2-F |
| 312 | 3-CF₃ | 1 | 3-F |
| 313 | 3-CF₃ | 1 | 2-Br |
| 314 | 3-CF₃ | 1 | 3-Br |
| 315 | 3-CF₃ | 1 | 2-OCH₃ |
| 316 | 3-CF₃ | 1 | 3-OCH₃ |
| 317 | 3-CF₃ | 1 | 2,3-CH₃ |
| 318 | 3-CF₃ | 1 | 2,4-CH₃ |
| 319 | 3-CF₃ | 1 | 2,5-CH₃ |
| 320 | 3-CF₃ | 1 | 3,4-CH₃ |
| 321 | 3-CF₃ | 1 | 2,3-Cl |
| 322 | 3-CF₃ | 1 | 2,4-Cl |
| 323 | 3-CF₃ | 1 | 2,5-Cl |
| 324 | 3-CF₃ | 1 | 3,4-Cl |
| 325 | 3-CF₃ | 1 | 2,3-F |
| 326 | 3-CF₃ | 1 | 2,4-F |
| 327 | 3-CF₃ | 1 | 2,5-F |
| 328 | 3-CF₃ | 1 | 3,4-F |
| 329 | 3-CF₃ | 1 | 2,3-Br |
| 330 | 3-CF₃ | 1 | 2,4-Br |
| 331 | 3-CF₃ | 1 | 2,5-Br |
| 332 | 3-CF₃ | 1 | 3,4-Br |
| 333 | 3-CF₃ | 1 | 2,3-OCH₃ |
| 334 | 3-CF₃ | 1 | 2,4-OCH₃ |
| 335 | 3-CF₃ | 1 | 2,5-OCH₃ |
| 336 | 3-CF₃ | 1 | 3,4-OCH₃ |
| 337 | 4-CF₃ | 1 | 2-CH₃ |
| 338 | 4-CF₃ | 1 | 3-CH₃ |
| 339 | 4-CF₃ | 1 | 2-CH₂CH₃ |
| 340 | 4-CF₃ | 1 | 3-CH₂CH₃ |
| 341 | 4-CF₃ | 1 | 2-CH₂CH₂CH₃ |
| 342 | 4-CF₃ | 1 | 3-CH₂CH₂CH₃ |
| 343 | 4-CF₃ | 1 | 2-isopropyl |
| 344 | 4-CF₃ | 1 | 3-isopropyl |
| 345 | 4-CF₃ | 1 | 2-butyl |
| 346 | 4-CF₃ | 1 | 3-butyl |
| 347 | 4-CF₃ | 1 | 2-isobutyl |
| 348 | 4-CF₃ | 1 | 3-isobutyl |
| 349 | 4-CF₃ | 1 | 2-t-butyl |
| 350 | 4-CF₃ | 1 | 3-t-butyl |
| 351 | 4-CF₃ | 1 | 2-Cl |
| 352 | 4-CF₃ | 1 | 3-Cl |
| 353 | 4-CF₃ | 1 | 2-F |
| 354 | 4-CF₃ | 1 | 3-F |
| 355 | 4-CF₃ | 1 | 2-Br |
| 356 | 4-CF₃ | 1 | 3-Br |
| 357 | 4-CF₃ | 1 | 2-OCH₃ |
| 358 | 4-CF₃ | 1 | 3-OCH₃ |
| 359 | 4-CF₃ | 1 | 2,3-CH₃ |
| 360 | 4-CF₃ | 1 | 2,4-CH₃ |
| 361 | 4-CF₃ | 1 | 2,5-CH₃ |
| 362 | 4-CF₃ | 1 | 3,4-CH₃ |
| 363 | 4-CF₃ | 1 | 2,3-Cl |
| 364 | 4-CF₃ | 1 | 2,4-Cl |
| 365 | 4-CF₃ | 1 | 2,5-Cl |
| 366 | 4-CF₃ | 1 | 3,4-Cl |
| 367 | 4-CF₃ | 1 | 2,3-F |
| 368 | 4-CF₃ | 1 | 2,4-F |
| 369 | 4-CF₃ | 1 | 2,5-F |
| 370 | 4-CF₃ | 1 | 3,4-F |
| 371 | 4-CF₃ | 1 | 2,3-Br |
| 372 | 4-CF₃ | 1 | 2,4-Br |
| 373 | 4-CF₃ | 1 | 2,5-Br |
| 374 | 4-CF₃ | 1 | 3,4-Br |
| 375 | 4-CF₃ | 1 | 2,3-OCH₃ |
| 376 | 4-CF₃ | 1 | 2,4-OCH₃ |
| 377 | 4-CF₃ | 1 | 2,5-OCH₃ |
| 378 | 4-CF₃ | 1 | 3,4-OCH₃ |
| 379 | 4-CN | 1 | 2-CH₃ |
| 380 | 4-CN | 1 | 3-CH₃ |
| 381 | 4-CN | 1 | 2-CH₂CH₃ |
| 382 | 4-CN | 1 | 3-CH₂CH₃ |
| 383 | 4-CN | 1 | 2-CH₂CH₂CH₃ |
| 384 | 4-CN | 1 | 3-CH₂CH₂CH₃ |
| 385 | 4-CN | 1 | 2-isopropyl |
| 386 | 4-CN | 1 | 3-isopropyl |
| 387 | 4-CN | 1 | 2-butyl |
| 388 | 4-CN | 1 | 3-butyl |
| 389 | 4-CN | 1 | 2-isobutyl |
| 390 | 4-CN | 1 | 3-isobutyl |
| 391 | 4-CN | 1 | 2-t-butyl |
| 392 | 4-CN | 1 | 3-t-butyl |
| 393 | 4-CN | 1 | 2-Cl |
| 394 | 4-CN | 1 | 3-Cl |
| 395 | 4-CN | 1 | 2-F |
| 396 | 4-CN | 1 | 3-F |
| 397 | 4-CN | 1 | 2-Br |
| 398 | 4-CN | 1 | 3-Br |
| 399 | 4-CN | 1 | 2-OCH₃ |
| 400 | 4-CN | 1 | 3-OCH₃ |
| 401 | 4-CN | 1 | 2,3-CH₃ |
| 402 | 4-CN | 1 | 2,4-CH₃ |
| 403 | 4-CN | 1 | 2,5-CH₃ |
| 404 | 4-CN | 1 | 3,4-CH₃ |
| 405 | 4-CN | 1 | 2,3-Cl |
| 406 | 4-CN | 1 | 2,4-Cl |
| 407 | 4-CN | 1 | 2,5-Cl |
| 408 | 4-CN | 1 | 3,4-Cl |
| 409 | 4-CN | 1 | 2,3-F |
| 410 | 4-CN | 1 | 2,4-F |

-continued

| Ex. # | R¹ᵃ | n | R⁵ |
|---|---|---|---|
| 411 | 4-CN | 1 | 2,5-F |
| 412 | 4-CN | 1 | 3,4-F |
| 413 | 4-CN | 1 | 2,3-Br |
| 414 | 4-CN | 1 | 2,4-Br |
| 415 | 4-CN | 1 | 2,5-Br |
| 416 | 4-CN | 1 | 3,4-Br |
| 417 | 4-CN | 1 | 2,3-OCH₃ |
| 418 | 4-CN | 1 | 2,4-OCH₃ |
| 419 | 4-CN | 1 | 2,5-OCH₃ |
| 420 | 4-CN | 1 | 3,4-OCH₃ |
| 421 | 3-CN | 1 | 2-CH₃ |
| 422 | 3-CN | 1 | 3-CH₃ |
| 423 | 3-CN | 1 | 2-CH₂CH₃ |
| 424 | 3-CN | 1 | 3-CH₂CH₃ |
| 425 | 3-CN | 1 | 2-CH₂CH₂CH₃ |
| 426 | 3-CN | 1 | 3-CH₂CH₂CH₃ |
| 427 | 3-CN | 1 | 2-isopropyl |
| 428 | 3-CN | 1 | 3-isopropyl |
| 429 | 3-CN | 1 | 2-butyl |
| 430 | 3-CN | 1 | 3-butyl |
| 431 | 3-CN | 1 | 2-isobutyl |
| 432 | 3-CN | 1 | 3-isobutyl |
| 433 | 3-CN | 1 | 2-t-butyl |
| 434 | 3-CN | 1 | 3-t-butyl |
| 435 | 3-CN | 1 | 2-Cl |
| 436 | 3-CN | 1 | 3-Cl |
| 437 | 3-CN | 1 | 2-F |
| 438 | 3-CN | 1 | 3-F |
| 439 | 3-CN | 1 | 2-Br |
| 440 | 3-CN | 1 | 3-Br |
| 441 | 3-CN | 1 | 2-OCH₃ |
| 442 | 3-CN | 1 | 3-OCH₃ |
| 443 | 3-CN | 1 | 2,3-CH₃ |
| 444 | 3-CN | 1 | 2,4-CH₃ |
| 445 | 3-CN | 1 | 2,5-CH₃ |
| 446 | 3-CN | 1 | 3,4-CH₃ |
| 447 | 3-CN | 1 | 2,3-Cl |
| 448 | 3-CN | 1 | 2,4-Cl |
| 449 | 3-CN | 1 | 2,5-Cl |
| 450 | 3-CN | 1 | 3,4-Cl |
| 451 | 3-CN | 1 | 2,3-F |
| 452 | 3-CN | 1 | 2,4-F |
| 453 | 3-CN | 1 | 2,5-F |
| 454 | 3-CN | 1 | 3,4-F |
| 455 | 3-CN | 1 | 2,3-Br |
| 456 | 3-CN | 1 | 2,4-Br |
| 457 | 3-CN | 1 | 2,5-Br |
| 458 | 3-CN | 1 | 3,4-Br |
| 459 | 3-CN | 1 | 2,3-OCH₃ |
| 460 | 3-CN | 1 | 2,4-OCH₃ |
| 461 | 3-CN | 1 | 2,5-OCH₃ |
| 462 | 3-CN | 1 | 3,4-OCH₃ |
| 463 | 2-F | 1 | H |
| 464 | 3-F | 1 | H |
| 465 | 4-F | 1 | H |
| 466 | 2-Cl | 1 | H |
| 467 | 3-Cl | 1 | H |
| 468 | 4-Cl | 1 | H |
| 469 | 2-Br | 1 | H |
| 470 | 3-Br | 1 | H |
| 471 | 4-Br | 1 | H |
| 472 | 3,4-F | 1 | H |
| 473 | 2,3-F | 1 | H |
| 474 | 2,4-F | 1 | H |
| 475 | 2-CN | 1 | H |
| 476 | 3-CN | 1 | H |
| 477 | 4-CN | 1 | H |
| 478 | 2-CF₃ | 1 | H |
| 479 | 3-CF₃ | 1 | H |
| 480 | 4-CF₃ | 1 | H |
| 481 | H | 1 | H |
| 482 | 2-OCH₃ | 1 | H |
| 483 | 3-OCH₃ | 1 | H |
| 484 | 4-OCH₃ | 1 | H |
| 485 | 2-CH₃ | 1 | H |
| 486 | 3-CH₃ | 1 | H |
| 487 | 4-CH₃ | 1 | H |
| 488 | 4-F | 2 | 2-CH₃ |
| 489 | 4-F | 2 | 3-CH₃ |
| 490 | 4-F | 2 | 2-CH₂CH₃ |
| 491 | 4-F | 2 | 3-CH₂CH₃ |
| 492 | 4-F | 2 | 2-CH₂CH₂CH₃ |
| 493 | 4-F | 2 | 3-CH₂CH₂CH₃ |
| 494 | 4-F | 2 | 2-isopropyl |
| 495 | 4-F | 2 | 3-isopropyl |
| 496 | 4-F | 2 | 2-butyl |
| 497 | 4-F | 2 | 3-butyl |
| 498 | 4-F | 2 | 2-isobutyl |
| 499 | 4-F | 2 | 3-isobutyl |
| 500 | 4-F | 2 | 2-t-butyl |
| 601 | 4-F | 2 | 3-t-butyl |
| 602 | 4-F | 2 | 2-Cl |
| 603 | 4-F | 2 | 3-Cl |
| 604 | 4-F | 2 | 2-F |
| 605 | 4-F | 2 | 3-F |
| 606 | 4-F | 2 | 2-Br |
| 607 | 4-F | 2 | 3-Br |
| 608 | 4-F | 2 | 2-OCH₃ |
| 609 | 4-F | 2 | 3-OCH₃ |
| 610 | 4-F | 2 | 2,3-CH₃ |
| 611 | 4-F | 2 | 2,4-CH₃ |
| 612 | 4-F | 2 | 2,5-CH₃ |
| 613 | 4-F | 2 | 3,4-CH₃ |
| 614 | 4-F | 2 | 3,5-CH₃ |
| 615 | 4-F | 2 | 4,5-CH₃ |
| 616 | 4-F | 2 | 2,3-Cl |
| 617 | 4-F | 2 | 2,4-Cl |
| 618 | 4-F | 2 | 2,5-Cl |
| 619 | 4-F | 2 | 3,4-Cl |
| 620 | 4-F | 2 | 3,5-Cl |
| 621 | 4-F | 2 | 4,5-Cl |
| 622 | 4-F | 2 | 2,3-F |
| 623 | 4-F | 2 | 2,4-F |
| 624 | 4-F | 2 | 2,5-F |
| 625 | 4-F | 2 | 3,4-F |
| 626 | 4-F | 2 | 3,5-F |
| 627 | 4-F |   | 4,5-F |
| 628 | 4-F | 2 | 2,3-Br |
| 629 | 4-F | 2 | 2,4-Br |
| 630 | 4-F | 2 | 2,5-Br |
| 631 | 4-F | 2 | 3,4-Br |
| 632 | 4-F | 2 | 3,5-Br |
| 633 | 4-F | 2 | 4,5-Br |
| 634 | 4-F | 2 | 2,3-OCH₃ |
| 635 | 4-F | 2 | 2,4-OCH₃ |
| 636 | 4-F | 2 | 2,5-OCH₃ |
| 637 | 4-F | 2 | 3,4-OCH₃ |
| 638 | 4-F | 2 | 3,5-OCH₃ |
| 639 | 4-F | 2 | 4,5-OCH₃ |
| 640 | 3-F | 2 | 2-CH₃ |
| 641 | 3-F | 2 | 3-CH₃ |
| 642 | 3-F | 2 | 2-CH₂CH₃ |
| 643 | 3-F | 2 | 3-CH₂CH₃ |
| 644 | 3-F | 2 | 2-CH₂CH₂CH₃ |
| 645 | 3-F | 2 | 3-CH₂CH₂CH₃ |
| 646 | 3-F | 2 | 2-isopropyl |
| 647 | 3-F | 2 | 3-isopropyl |
| 648 | 3-F | 2 | 2-butyl |
| 649 | 3-F | 2 | 3-butyl |
| 650 | 3-F | 2 | 2-isobutyl |
| 651 | 3-F | 2 | 3-isobutyl |
| 652 | 3-F | 2 | 2-t-butyl |
| 653 | 3-F | 2 | 3-t-butyl |
| 654 | 3-F | 2 | 2-Cl |
| 655 | 3-F | 2 | 3-Cl |
| 656 | 3-F | 2 | 2-F |
| 657 | 3-F | 2 | 3-F |
| 658 | 3-F | 2 | 2-Br |
| 659 | 3-F | 2 | 3-Br |
| 660 | 3-F | 2 | 2-OCH₃ |
| 661 | 3-F | 2 | 3-OCH₃ |
| 662 | 3-F | 2 | 2,3-CH₃ |
| 663 | 3-F | 2 | 2,4-CH₃ |
| 664 | 3-F | 2 | 2,5-CH₃ |

| Ex. # | $R^{1a}$ | n | $R^5$ |
|---|---|---|---|
| 665 | 3-F | 2 | 3,4-CH$_3$ |
| 666 | 3-F | 2 | 2,3-Cl |
| 667 | 3-F | 2 | 2,4-Cl |
| 668 | 3-F | 2 | 2,5-Cl |
| 669 | 3-F | 2 | 3,4-Cl |
| 670 | 3-F | 2 | 2,3-F |
| 671 | 3-F | 2 | 2,4-F |
| 672 | 3-F | 2 | 2,5-F |
| 673 | 3-F | 2 | 3,4-F |
| 674 | 3-F | 2 | 2,3-Br |
| 675 | 3-F | 2 | 2,4-Br |
| 676 | 3-F | 2 | 2,5-Br |
| 677 | 3-F | 2 | 3,4-Br |
| 678 | 3-F | 2 | 2,3-OCH$_3$ |
| 679 | 3-F | 2 | 2,4-OCH$_3$ |
| 680 | 3-F | 2 | 2,5-OCH$_3$ |
| 681 | 3-F | 2 | 3,4-OCH$_3$ |
| 682 | 2,3-F | 2 | 2-CH$_3$ |
| 683 | 2,3-F | 2 | 3-CH$_3$ |
| 684 | 2,3-F | 2 | 2-CH$_2$CH$_3$ |
| 685 | 2,3-F | 2 | 3-CH$_2$CH$_3$ |
| 686 | 2,3-F | 2 | 2-CH$_2$CH$_2$CH$_3$ |
| 687 | 2,3-F | 2 | 3-CH$_2$CH$_2$CH$_3$ |
| 688 | 2,3-F | 2 | 2-isopropyl |
| 689 | 2,3-F | 2 | 3-isopropyl |
| 690 | 2,3-F | 2 | 2-butyl |
| 691 | 2,3-F | 2 | 3-butyl |
| 692 | 2,3-F | 2 | 2-isobutyl |
| 693 | 2,3-F | 2 | 3-isobutyl |
| 694 | 2,3-F | 2 | 2-t-butyl |
| 695 | 2,3-F | 2 | 3-t-butyl |
| 696 | 2,3-F | 2 | 2-Cl |
| 697 | 2,3-F | 2 | 3-Cl |
| 698 | 2,3-F | 2 | 2-F |
| 699 | 2,3-F | 2 | 3-F |
| 700 | 2,3-F | 2 | 2-Br |
| 701 | 2,3-F | 2 | 3-Br |
| 702 | 2,3-F | 2 | 2-OCH$_3$ |
| 703 | 2,3-F | 2 | 3-OCH$_3$ |
| 704 | 2,3-F | 2 | 2,3-CH$_3$ |
| 705 | 2,3-F | 2 | 2,4-CH$_3$ |
| 706 | 2,3-F | 2 | 2,5-CH$_3$ |
| 707 | 2,3-F | 2 | 3,4-CH$_3$ |
| 708 | 2,3-F | 2 | 2,3-Cl |
| 709 | 2,3-F | 2 | 2,4-Cl |
| 710 | 2,3-F | 2 | 2,5-Cl |
| 711 | 2,3-F | 2 | 3,4-Cl |
| 712 | 2,3-F | 2 | 2,3-F |
| 713 | 2,3-F | 2 | 2,4-F |
| 714 | 2,3-F | 2 | 2,5-F |
| 715 | 2,3-F | 2 | 3,4-F |
| 716 | 2,3-F | 2 | 2,3-Br |
| 717 | 2,3-F | 2 | 2,4-Br |
| 718 | 2,3-F | 2 | 2,5-Br |
| 719 | 2,3-F | 2 | 3,4-Br |
| 720 | 2,3-F | 2 | 2,3-OCH$_3$ |
| 721 | 2,3-F | 2 | 2,4-OCH$_3$ |
| 722 | 2,3-F | 2 | 2,5-OCH$_3$ |
| 723 | 2,3-F | 2 | 3,4-OCH$_3$ |
| 724 | 3,4-F | 2 | 2-CH$_3$ |
| 725 | 3,4-F | 2 | 3-CH$_3$ |
| 726 | 3,4-F | 2 | 2-CH$_2$CH$_3$ |
| 727 | 3,4-F | 2 | 3-CH$_2$CH$_3$ |
| 728 | 3,4-F | 2 | 2-CH$_2$CH$_2$CH$_3$ |
| 729 | 3,4-F | 2 | 3-CH$_2$CH$_2$CH$_3$ |
| 730 | 3,4-F | 2 | 2-isopropyl |
| 731 | 3,4-F | 2 | 3-isopropyl |
| 732 | 3,4-F | 2 | 2-butyl |
| 733 | 3,4-F | 2 | 3-butyl |
| 734 | 3,4-F | 2 | 2-isobutyl |
| 735 | 3,4-F | 2 | 3-isobutyl |
| 736 | 3,4-F | 2 | 2-t-butyl |
| 737 | 3,4-F | 2 | 3-t-butyl |
| 738 | 3,4-F | 2 | 2-Cl |
| 739 | 3,4-F | 2 | 3-Cl |
| 740 | 3,4-F | 2 | 2-F |
| 741 | 3,4-F | 2 | 3-F |
| 742 | 3,4-F | 2 | 2-Br |
| 743 | 3,4-F | 2 | 3-Br |
| 744 | 3,4-F | 2 | 2-OCH$_3$ |
| 745 | 3,4-F | 2 | 3-OCH$_3$ |
| 746 | 3,4-F | 2 | 2,3-CH$_3$ |
| 747 | 3,4-F | 2 | 2,4-CH$_3$ |
| 748 | 3,4-F | 2 | 2,5-CH$_3$ |
| 749 | 3,4-F | 2 | 3,4-CH$_3$ |
| 750 | 3,4-F | 2 | 2,3-Cl |
| 751 | 3,4-F | 2 | 2,4-Cl |
| 752 | 3,4-F | 2 | 2,5-Cl |
| 753 | 3,4-F | 2 | 3,4-Cl |
| 754 | 3,4-F | 2 | 2,3-F |
| 755 | 3,4-F | 2 | 2,4-F |
| 756 | 3,4-F | 2 | 2,5-F |
| 757 | 3,4-F | 2 | 3,4-F |
| 758 | 3,4-F | 2 | 2,3-Br |
| 759 | 3,4-F | 2 | 2,4-Br |
| 760 | 3,4-F | 2 | 2,5-Br |
| 761 | 3,4-F | 2 | 3,4-Br |
| 762 | 3,4-F | 2 | 2,3-OCH$_3$ |
| 763 | 3,4-F | 2 | 2,4-OCH$_3$ |
| 764 | 3,4-F | 2 | 2,5-OCH$_3$ |
| 765 | 3,4-F | 2 | 3,4-OCH$_3$ |
| 766 | 4-Cl | 2 | 2-CH$_3$ |
| 767 | 4-Cl | 2 | 3-CH$_3$ |
| 768 | 4-Cl | 2 | 2-CH$_2$CH$_3$ |
| 769 | 4-Cl | 2 | 3-CH$_2$CH$_3$ |
| 770 | 4-Cl | 2 | 2-CH$_2$CH$_2$CH$_3$ |
| 771 | 4-Cl | 2 | 3-CH$_2$CH$_2$CH$_3$ |
| 772 | 4-Cl | 2 | 2-isopropyl |
| 773 | 4-Cl | 2 | 3-isopropyl |
| 774 | 4-Cl | 2 | 2-butyl |
| 775 | 4-Cl | 2 | 3-butyl |
| 776 | 4-Cl | 2 | 2-isobutyl |
| 777 | 4-Cl | 2 | 3-isobutyl |
| 778 | 4-Cl | 2 | 2-t-butyl |
| 779 | 4-Cl | 2 | 3-t-butyl |
| 780 | 4-Cl | 2 | 2-Cl |
| 781 | 4-Cl | 2 | 3-Cl |
| 782 | 4-Cl | 2 | 2-F |
| 783 | 4-Cl | 2 | 3-F |
| 784 | 4-Cl | 2 | 2-Br |
| 785 | 4-Cl | 2 | 3-Br |
| 786 | 4-Cl | 2 | 2-OCH$_3$ |
| 787 | 4-Cl | 2 | 3-OCH$_3$ |
| 788 | 4-Cl | 2 | 2,3-CH$_3$ |
| 789 | 4-Cl | 2 | 2,4-CH$_3$ |
| 790 | 4-Cl | 2 | 2,5-CH$_3$ |
| 791 | 4-Cl | 2 | 3,4-CH$_3$ |
| 792 | 4-Cl | 2 | 2,3-Cl |
| 793 | 4-Cl | 2 | 2,4-Cl |
| 794 | 4-Cl | 2 | 2,5-Cl |
| 795 | 4-Cl | 2 | 3,4-Cl |
| 796 | 4-Cl | 2 | 2,3-F |
| 797 | 4-Cl | 2 | 2,4-F |
| 798 | 4-Cl | 2 | 2,5-F |
| 799 | 4-Cl | 2 | 3,4-F |
| 800 | 4-Cl | 2 | 2,3-Br |
| 801 | 4-Cl | 2 | 2,4-Br |
| 802 | 4-Cl | 2 | 2,5-Br |
| 803 | 4-Cl | 2 | 3,4-Br |
| 804 | 4-Cl | 2 | 2,3-OCH$_3$ |
| 805 | 4-Cl | 2 | 2,4-OCH$_3$ |
| 806 | 4-Cl | 2 | 2,5-OCH$_3$ |
| 807 | 4-Cl | 2 | 3,4-OCH$_3$ |
| 808 | 3-Cl | 2 | 2-CH$_3$ |
| 809 | 3-Cl | 2 | 3-CH$_3$ |
| 810 | 3-Cl | 2 | 2-CH$_2$CH$_3$ |
| 811 | 3-Cl | 2 | 3-CH$_2$CH$_3$ |
| 812 | 3-Cl | 2 | 2-CH$_2$CH$_2$CH$_3$ |
| 813 | 3-Cl | 2 | 3-CH$_2$CH$_2$CH$_3$ |
| 814 | 3-Cl | 2 | 2-isopropyl |
| 815 | 3-Cl | 2 | 3-isopropyl |
| 816 | 3-Cl | 2 | 2-butyl |
| 817 | 3-Cl | 2 | 3-butyl |
| 818 | 3-Cl | 2 | 2-isobutyl |

-continued

| Ex. # | R$^{1a}$ | n | R$^5$ |
|---|---|---|---|
| 819 | 3-Cl | 2 | 3-isobutyl |
| 820 | 3-Cl | 2 | 2-t-butyl |
| 821 | 3-Cl | 2 | 3-t-butyl |
| 822 | 3-Cl | 2 | 2-Cl |
| 823 | 3-Cl | 2 | 3-Cl |
| 824 | 3-Cl | 2 | 2-F |
| 825 | 3-Cl | 2 | 3-F |
| 826 | 3-Cl | 2 | 2-Br |
| 827 | 3-Cl | 2 | 3-Br |
| 828 | 3-Cl | 2 | 2-OCH$_3$ |
| 829 | 3-Cl | 2 | 3-OCH$_3$ |
| 830 | 3-Cl | 2 | 2,3-CH$_3$ |
| 831 | 3-Cl | 2 | 2,4-CH$_3$ |
| 832 | 3-Cl | 2 | 2,5-CH$_3$ |
| 833 | 3-Cl | 2 | 3,4-CH$_3$ |
| 834 | 3-Cl | 2 | 2,3-Cl |
| 835 | 3-Cl | 2 | 2,4-Cl |
| 836 | 3-Cl | 2 | 2,5-Cl |
| 837 | 3-Cl | 2 | 3,4-Cl |
| 838 | 3-Cl | 2 | 2,3-F |
| 839 | 3-Cl | 2 | 2,4-F |
| 840 | 3-Cl | 2 | 2,5-F |
| 841 | 3-Cl | 2 | 3,4-F |
| 842 | 3-Cl | 2 | 2,3-Br |
| 843 | 3-Cl | 2 | 2,4-Br |
| 844 | 3-Cl | 2 | 2,5-Br |
| 845 | 3-Cl | 2 | 3,4-Br |
| 846 | 3-Cl | 2 | 2,3-OCH$_3$ |
| 847 | 3-Cl | 2 | 2,4-OCH$_3$ |
| 848 | 3-Cl | 2 | 2,5-OCH$_3$ |
| 849 | 3-Cl | 2 | 3,4-OCH$_3$ |
| 850 | 3-CF$_3$ | 2 | 2-CH$_3$ |
| 851 | 3-CF$_3$ | 2 | 3-CH$_3$ |
| 852 | 3-CF$_3$ | 2 | 2-CH$_2$CH$_3$ |
| 853 | 3-CF$_3$ | 2 | 3-CH$_2$CH$_3$ |
| 854 | 3-CF$_3$ | 2 | 2-CH$_2$CH$_2$CH$_3$ |
| 855 | 3-CF$_3$ | 2 | 3-CH$_2$CH$_2$CH$_3$ |
| 856 | 3-CF$_3$ | 2 | 2-isopropyl |
| 857 | 3-CF$_3$ | 2 | 3-isopropyl |
| 858 | 3-CF$_3$ | 2 | 2-butyl |
| 859 | 3-CF$_3$ | 2 | 3-butyl |
| 860 | 3-CF$_3$ | 2 | 2-isobutyl |
| 861 | 3-CF$_3$ | 2 | 3-isobutyl |
| 862 | 3-CF$_3$ | 2 | 2-t-butyl |
| 863 | 3-CF$_3$ | 2 | 3-t-butyl |
| 864 | 3-CF$_3$ | 2 | 2-Cl |
| 865 | 3-CF$_3$ | 2 | 3-Cl |
| 866 | 3-CF$_3$ | 2 | 2-F |
| 867 | 3-CF$_3$ | 2 | 3-F |
| 868 | 3-CF$_3$ | 2 | 2-Br |
| 869 | 3-CF$_3$ | 2 | 3-Br |
| 870 | 3-CF$_3$ | 2 | 2-OCH$_3$ |
| 871 | 3-CF$_3$ | 2 | 3-OCH$_3$ |
| 872 | 3-CF$_3$ | 2 | 2,3-CH$_3$ |
| 873 | 3-CF$_3$ | 2 | 2,4-CH$_3$ |
| 874 | 3-CF$_3$ | 2 | 2,5-CH$_3$ |
| 875 | 3-CF$_3$ | 2 | 3,4-CH$_3$ |
| 876 | 3-CF$_3$ | 2 | 2,3-Cl |
| 877 | 3-CF$_3$ | 2 | 2,4-Cl |
| 878 | 3-CF$_3$ | 2 | 2,5-Cl |
| 879 | 3-CF$_3$ | 2 | 3,4-Cl |
| 880 | 3-CF$_3$ | 2 | 2,3-F |
| 881 | 3-CF$_3$ | 2 | 2,4-F |
| 882 | 3-CF$_3$ | 2 | 2,5-F |
| 883 | 3-CF$_3$ | 2 | 3,4-F |
| 884 | 3-CF$_3$ | 2 | 2,3-Br |
| 885 | 3-CF$_3$ | 2 | 2,4-Br |
| 886 | 3-CF$_3$ | 2 | 2,5-Br |
| 887 | 3-CF$_3$ | 2 | 3,4-Br |
| 888 | 3-CF$_3$ | 2 | 2,3-OCH$_3$ |
| 889 | 3-CF$_3$ | 2 | 2,4-OCH$_3$ |
| 890 | 3-CF$_3$ | 2 | 2,5-OCH$_3$ |
| 891 | 3-CF$_3$ | 2 | 3,4-OCH$_3$ |
| 892 | 4-CF$_3$ | 2 | 2-CH$_3$ |
| 893 | 4-CF$_3$ | 2 | 3-CH$_3$ |
| 894 | 4-CF$_3$ | 2 | 2-CH$_2$CH$_3$ |
| 895 | 4-CF$_3$ | 2 | 3-CH$_2$CH$_3$ |

-continued

| Ex. # | R$^{1a}$ | n | R$^5$ |
|---|---|---|---|
| 896 | 4-CF$_3$ | 2 | 2-CH$_2$CH$_2$CH$_3$ |
| 897 | 4-CF$_3$ | 2 | 3-CH$_2$CH$_2$CH$_3$ |
| 898 | 4-CF$_3$ | 2 | 2-isopropyl |
| 899 | 4-CF$_3$ | 2 | 3-isopropyl |
| 900 | 4-CF$_3$ | 2 | 2-butyl |
| 901 | 4-CF$_3$ | 2 | 3-butyl |
| 902 | 4-CF$_3$ | 2 | 2-isobutyl |
| 903 | 4-CF$_3$ | 2 | 3-isobutyl |
| 904 | 4-CF$_3$ | 2 | 2-t-butyl |
| 905 | 4-CF$_3$ | 2 | 3-t-butyl |
| 906 | 4-CF$_3$ | 2 | 2-Cl |
| 907 | 4-CF$_3$ | 2 | 3-Cl |
| 908 | 4-CF$_3$ | 2 | 2-F |
| 909 | 4-CF$_3$ | 2 | 3-F |
| 910 | 4-CF$_3$ | 2 | 2-Br |
| 911 | 4-CF$_3$ | 2 | 3-Br |
| 912 | 4-CF$_3$ | 2 | 2-OCH$_3$ |
| 913 | 4-CF$_3$ | 2 | 3-OCH$_3$ |
| 914 | 4-CF$_3$ | 2 | 2,3-CH$_3$ |
| 915 | 4-CF$_3$ | 2 | 2,4-CH$_3$ |
| 916 | 4-CF$_3$ | 2 | 2,5-CH$_3$ |
| 917 | 4-CF$_3$ | 2 | 3,4-CH$_3$ |
| 918 | 4-CF$_3$ | 2 | 2,3-Cl |
| 919 | 4-CF$_3$ | 2 | 2,4-Cl |
| 920 | 4-CF$_3$ | 2 | 2,5-Cl |
| 921 | 4-CF$_3$ | 2 | 3,4-Cl |
| 922 | 4-CF$_3$ | 2 | 2,3-F |
| 923 | 4-CF$_3$ | 2 | 2,4-F |
| 924 | 4-CF$_3$ | 2 | 2,5-F |
| 925 | 4-CF$_3$ | 2 | 3,4-F |
| 926 | 4-CF$_3$ | 2 | 2,3-Br |
| 927 | 4-CF$_3$ | 2 | 2,4-Br |
| 928 | 4-CF$_3$ | 2 | 2,5-Br |
| 929 | 4-CF$_3$ | 2 | 3,4-Br |
| 930 | 4-CF$_3$ | 2 | 2,3-OCH$_3$ |
| 931 | 4-CF$_3$ | 2 | 2,4-OCH$_3$ |
| 932 | 4-CF$_3$ | 2 | 2,5-OCH$_3$ |
| 933 | 4-CF$_3$ | 2 | 3,4-OCH$_3$ |
| 934 | 4-CN | 2 | 2-CH$_3$ |
| 935 | 4-CN | 2 | 3-CH$_3$ |
| 936 | 4-CN | 2 | 2-CH$_2$CH$_3$ |
| 937 | 4-CN | 2 | 3-CH$_2$CH$_3$ |
| 938 | 4-CN | 2 | 2-CH$_2$CH$_2$CH$_3$ |
| 939 | 4-CN | 2 | 3-CH$_2$CH$_2$CH$_3$ |
| 940 | 4-CN | 2 | 2-isopropyl |
| 941 | 4-CN | 2 | 3-isopropyl |
| 942 | 4-CN | 2 | 2-butyl |
| 943 | 4-CN | 2 | 3-butyl |
| 944 | 4-CN | 2 | 2-isobutyl |
| 945 | 4-CN | 2 | 3-isobutyl |
| 946 | 4-CN | 2 | 2-t-butyl |
| 947 | 4-CN | 2 | 3-t-butyl |
| 948 | 4-CN | 2 | 2-Cl |
| 949 | 4-CN | 2 | 3-Cl |
| 950 | 4-CN | 2 | 2-F |
| 951 | 4-CN | 2 | 3-F |
| 952 | 4-CN | 2 | 2-Br |
| 953 | 4-CN | 2 | 3-Br |
| 954 | 4-CN | 2 | 2-OCH$_3$ |
| 955 | 4-CN | 2 | 3-OCH$_3$ |
| 956 | 4-CN | 2 | 2,3-CH$_3$ |
| 957 | 4-CN | 2 | 2,4-CH$_3$ |
| 958 | 4-CN | 2 | 2,5-CH$_3$ |
| 959 | 4-CN | 2 | 3,4-CH$_3$ |
| 960 | 4-CN | 2 | 2,3-Cl |
| 961 | 4-CN | 2 | 2,4-Cl |
| 962 | 4-CN | 2 | 2,5-Cl |
| 963 | 4-CN | 2 | 3,4-Cl |
| 964 | 4-CN | 2 | 2,3-F |
| 965 | 4-CN | 2 | 2,4-F |
| 966 | 4-CN | 2 | 2,5-F |
| 967 | 4-CN | 2 | 3,4-F |
| 968 | 4-CN | 2 | 2,3-Br |
| 969 | 4-CN | 2 | 2,4-Br |
| 970 | 4-CN | 2 | 2,5-Br |
| 971 | 4-CN | 2 | 3,4-Br |
| 972 | 4-CN | 2 | 2,3-OCH$_3$ |

| Ex. # | R¹ᵃ | n | R⁵ |
|---|---|---|---|
| 973 | 4-CN | 2 | 2,4-OCH₃ |
| 974 | 4-CN | 2 | 2,5-OCH₃ |
| 975 | 4-CN | 2 | 3,4-OCH₃ |
| 976 | 3-CN | 2 | 2-CH₃ |
| 977 | 3-CN | 2 | 3-CH₃ |
| 978 | 3-CN | 2 | 2-CH₂CH₃ |
| 979 | 3-CN | 2 | 3-CH₂CH₃ |
| 980 | 3-CN | 2 | 2-CH₂CH₂CH₃ |
| 981 | 3-CN | 2 | 3-CH₂CH₂CH₃ |
| 982 | 3-CN | 2 | 2-isopropyl |
| 983 | 3-CN | 2 | 3-isopropyl |
| 984 | 3-CN | 2 | 2-butyl |
| 985 | 3-CN | 2 | 3-butyl |
| 986 | 3-CN | 2 | 2-isobutyl |
| 987 | 3-CN | 2 | 3-isobutyl |
| 988 | 3-CN | 2 | 2-t-butyl |
| 989 | 3-CN | 2 | 3-t-butyl |
| 990 | 3-CN | 2 | 2-Cl |
| 991 | 3-CN | 2 | 3-Cl |
| 992 | 3-CN | 2 | 2-F |
| 993 | 3-CN | 2 | 3-F |
| 994 | 3-CN | 2 | 2-Br |
| 995 | 3-CN | 2 | 3-Br |
| 996 | 3-CN | 2 | 2-OCH₃ |
| 997 | 3-CN | 2 | 3-OCH₃ |
| 998 | 3-CN | 2 | 2,3-CH₃ |
| 999 | 3-CN | 2 | 2,4-CH₃ |
| 1000 | 3-CN | 2 | 2,5-CH₃ |
| 1001 | 3-CN | 2 | 3,4-CH₃ |
| 1002 | 3-CN | 2 | 2,3-Cl |
| 1003 | 3-CN | 2 | 2,4-Cl |
| 1004 | 3-CN | 2 | 2,5-Cl |
| 1005 | 3-CN | 2 | 3,4-Cl |
| 1006 | 3-CN | 2 | 2,3-F |
| 1007 | 3-CN | 2 | 2,4-F |
| 1008 | 3-CN | 2 | 2,5-F |
| 1009 | 3-CN | 2 | 3,4-F |
| 1010 | 3-CN | 2 | 2,3-Br |
| 1011 | 3-CN | 2 | 2,4-Br |
| 1012 | 3-CN | 2 | 2,5-Br |
| 1013 | 3-CN | 2 | 3,4-Br |
| 1014 | 3-CN | 2 | 2,3-OCH₃ |
| 1015 | 3-CN | 2 | 2,4-OCH₃ |
| 1016 | 3-CN | 2 | 2,5-OCH₃ |
| 1017 | 3-CN | 2 | 3,4-OCH₃ |
| 1018 | 2-F | 2 | H |
| 1019 | 3-F | 2 | H |
| 1020 | 4-F | 2 | H |
| 1021 | 2-Cl | 2 | H |
| 1022 | 3-Cl | 2 | H |
| 1023 | 4-Cl | 2 | H |
| 1024 | 2-Br | 2 | H |
| 1025 | 3-Br | 2 | H |
| 1026 | 4-Br | 2 | H |
| 1027 | 3,4-F | 2 | H |
| 1028 | 2,3-F | 2 | H |
| 1029 | 2,4-F | 2 | H |
| 1030 | 2-CN | 2 | H |
| 1031 | 3-CN | 2 | H |
| 1032 | 4-CN | 2 | H |
| 1033 | 2-CF₃ | 2 | H |
| 1034 | 3-CF₃ | 2 | H |
| 1035 | 4-CF₃ | 2 | H |
| 1036 | H | 2 | H |
| 1037 | 2-OCH₃ | 2 | H |
| 1038 | 3-OCH₃ | 2 | H |
| 1039 | 4-OCH₃ | 2 | H |
| 1040 | 2-CH₃ | 2 | H |
| 1041 | 3-CH₃ | 2 | H |
| 1042 | 4-CH₃ | 2 | H |
| 1043 | 2-F | 2 | 3,4-fused phenyl |
| 1044 | 3-F | 2 | 3,4-fused phenyl |
| 1045 | 4-F | 2 | 3,4-fused phenyl |
| 1046 | 2-Cl | 2 | 3,4-fused phenyl |
| 1047 | 3-Cl | 2 | 3,4-fused phenyl |
| 1048 | 4-Cl | 2 | 3,4-fused phenyl |
| 1049 | 2-Br | 2 | 3,4-fused phenyl |
| 1050 | 3-Br | 2 | 3,4-fused phenyl |
| 1051 | 4-Br | 2 | 3,4-fused phenyl |
| 1052 | 3,4-F | 2 | 3,4-fused phenyl |
| 1053 | 2,3-F | 2 | 3,4-fused phenyl |
| 1054 | 2,4-F | 2 | 3,4-fused phenyl |
| 1055 | 2-CN | 2 | 3,4-fused phenyl |
| 1056 | 3-CN | 2 | 3,4-fused phenyl |
| 1057 | 4-CN | 2 | 3,4-fused phenyl |
| 1058 | 2-CF₃ | 2 | 3,4-fused phenyl |
| 1059 | 3-CF₃ | 2 | 3,4-fused phenyl |
| 1060 | 4-CF₃ | 2 | 3,4-fused phenyl |
| 1061 | H | 2 | 3,4-fused phenyl |
| 1062 | 2-OCH₃ | 2 | 3,4-fused phenyl |
| 1063 | 3-OCH₃ | 2 | 3,4-fused phenyl |
| 1064 | 4-OCH₃ | 2 | 3,4-fused phenyl |
| 1065 | 2-CH₃ | 2 | 3,4-fused phenyl |
| 1066 | 3-CH₃ | 2 | 3,4-fused phenyl |
| 1067 | 4-CH₃ | 2 | 3,4-fused phenyl |
| 1068 | 2-F | 1 | 3,4-fused phenyl |
| 1069 | 3-F | 1 | 3,4-fused phenyl |
| 1070 | 4-F | 1 | 3,4-fused phenyl |
| 1071 | 2-Cl | 1 | 3,4-fused phenyl |
| 1072 | 3-Cl | 1 | 3,4-fused phenyl |
| 1073 | 4-Cl | 1 | 3,4-fused phenyl |
| 1074 | 2-Br | 1 | 3,4-fused phenyl |
| 1075 | 3-Br | 1 | 3,4-fused phenyl |
| 1076 | 4-Br | 1 | 3,4-fused phenyl |
| 1077 | 3,4-F | 1 | 3,4-fused phenyl |
| 1078 | 2,3-F | 1 | 3,4-fused phenyl |
| 1079 | 2,4-F | 1 | 3,4-fused phenyl |
| 1080 | 2-CN | 1 | 3,4-fused phenyl |
| 1081 | 3-CN | 1 | 3,4-fused phenyl |
| 1082 | 4-CN | 1 | 3,4-fused phenyl |
| 1083 | 2-CF₃ | 1 | 3,4-fused phenyl |
| 1084 | 3-CF₃ | 1 | 3,4-fused phenyl |
| 1085 | 4-CF₃ | 1 | 3,4-fused phenyl |
| 1086 | H | 1 | 3,4-fused phenyl |
| 1087 | 2-OCH₃ | 1 | 3,4-fused phenyl |
| 1088 | 3-OCH₃ | 1 | 3,4-fused phenyl |
| 1089 | 4-OCH₃ | 1 | 3,4-fused phenyl |
| 1090 | 2-CH₃ | 1 | 3,4-fused phenyl |
| 1091 | 3-CH₃ | 1 | 3,4-fused phenyl |
| 1092 | 4-CH₃ | 1 | 3,4-fused phenyl |
| 1093 | 2-F | 2 | Q |
| 1094 | 3-F | 2 | Q |
| 1095 | 4-F | 2 | Q |
| 1096 | 2-Cl | 2 | Q |
| 1097 | 3-Cl | 2 | Q |
| 1098 | 4-Cl | 2 | Q |
| 1099 | 2-Br | 2 | Q |
| 1100 | 3-Br | 2 | Q |
| 1101 | 4-Br | 2 | Q |
| 1102 | 3,4-F | 2 | Q |
| 1103 | 2,3-F | 2 | Q |
| 1104 | 2,4-F | 2 | Q |
| 1105 | 2-CN | 2 | Q |
| 1106 | 3-CN | 2 | Q |
| 1107 | 4-CN | 2 | Q |
| 1108 | 2-CF₃ | 2 | Q |
| 1109 | 3-CF₃ | 2 | Q |
| 1110 | 4-CF₃ | 2 | Q |
| 1111 | H | 2 | Q |
| 1112 | 2-OCH₃ | 2 | Q |
| 1113 | 3-OCH₃ | 2 | Q |
| 1114 | 4-OCH₃ | 2 | Q |
| 1115 | 2-CH₃ | 2 | Q |
| 1116 | 3-CH₃ | 2 | Q |
| 1117 | 4-CH₃ | 2 | Q |
| 1118 | 2-F | 1 | 2,3-fused phenyl |
| 1119 | 3-F | 1 | 2,3-fused phenyl |
| 1120 | 4-F | 1 | 2,3-fused phenyl |
| 1121 | 2-Cl | 1 | 2,3-fused phenyl |
| 1122 | 3-Cl | 1 | 2,3-fused phenyl |
| 1123 | 4-Cl | 1 | 2,3-fused phenyl |
| 1124 | 2-Br | 1 | 2,3-fused phenyl |
| 1125 | 3-Br | 1 | 2,3-fused phenyl |
| 1126 | 4-Br | 1 | 2,3-fused phenyl |

-continued

| Ex. # | $R^{1a}$ | n | $R^5$ |
|---|---|---|---|
| 1127 | 3,4-F | 1 | 2,3-fused phenyl |
| 1128 | 2,3-F | 1 | 2,3-fused phenyl |
| 1129 | 2,4-F | 1 | 2,3-fused phenyl |
| 1130 | 2-CN | 1 | 2,3-fused phenyl |
| 1131 | 3-CN | 1 | 2,3-fused phenyl |
| 1132 | 4-CN | 1 | 2,3-fused phenyl |
| 1133 | 2-$CF_3$ | 1 | 2,3-fused phenyl |
| 1134 | 3-$CF_3$ | 1 | 2,3-fused phenyl |
| 1135 | 4-$CF_3$ | 1 | 2,3-fused phenyl |
| 1196 | H | 1 | 2,3-fused phenyl |
| 1137 | 2-$OCH_3$ | 1 | 2,3-fused phenyl |
| 1138 | 3-$OCH_3$ | 1 | 2,3-fused phenyl |
| 1139 | 4-$OCH_3$ | 1 | 2,3-fused phenyl |
| 1140 | 2-$CH_3$ | 1 | 2,3-fused phenyl |
| 1141 | 3-$CH_3$ | 1 | 2,3-fused phenyl |
| 1142 | 4-$CH_3$ | 1 | 2,3-fused phenyl |
| 1143 | 2-F | 2 | 2,3-fused phenyl |
| 1144 | 3-F | 2 | 2,3-fused phenyl |
| 1145 | 4-F | 2 | 2,3-fused phenyl |
| 1146 | 2-Cl | 2 | 2,3-fused phenyl |
| 1147 | 3-Cl | 2 | 2,3-fused phenyl |
| 1148 | 4-Cl | 2 | 2,3-fused phenyl |
| 1149 | 2-Br | 2 | 2,3-fused phenyl |
| 1150 | 3-Br | 2 | 2,3-fused phenyl |
| 1151 | 4-Br | 2 | 2,3-fused phenyl |
| 1152 | 3,4-F | 2 | 2,3-fused phenyl |
| 1153 | 2,3-F | 2 | 2,3-fused phenyl |
| 1154 | 2,4-F | 2 | 2,3-fused phenyl |
| 1155 | 2-CN | 2 | 2,3-fused phenyl |
| 1156 | 3-CN | 2 | 2,3-fused phenyl |
| 1157 | 4-CN | 2 | 2,3-fused phenyl |
| 1158 | 2-$CF_3$ | 2 | 2,3-fused phenyl |
| 1159 | 3-$CF_3$ | 2 | 2,3-fused phenyl |
| 1160 | 4-$CF_3$ | 2 | 2,3-fused phenyl |
| 1161 | H | 2 | 2,3-fused phenyl |
| 1162 | 2-$OCH_3$ | 2 | 2,3-fused phenyl |
| 1163 | 3-$OCH_3$ | 2 | 2,3-fused phenyl |
| 1164 | 4-$OCH_3$ | 2 | 2,3-fused phenyl |
| 1165 | 2-$CH_3$ | 2 | 2,3-fused phenyl |
| 1166 | 3-$CH_3$ | 2 | 2,3-fused phenyl |
| 1167 | 4-$CH_3$ | 2 | 2,3-fused phenyl |
| 1168 | 2-F | 2 | 4,5-fused phenyl |
| 1169 | 3-F | 2 | 4,5-fused phenyl |
| 1170 | 4-F | 2 | 4,5-fused phenyl |
| 1171 | 2-Cl | 2 | 4,5-fused phenyl |
| 1172 | 3-Cl | 2 | 4,5-fused phenyl |
| 1173 | 4-Cl | 2 | 4,5-fused phenyl |
| 1174 | 2-Br | 2 | 4,5-fused phenyl |
| 1175 | 3-Br | 2 | 4,5-fused phenyl |
| 1176 | 4-Br | 2 | 4,5-fused phenyl |
| 1177 | 3,4-F | 2 | 4,5-fused phenyl |
| 1178 | 2,3-F | 2 | 4,5-fused phenyl |
| 1179 | 2,4-F | 2 | 4,5-fused phenyl |
| 1180 | 2-CN | 2 | 4,5-fused phenyl |
| 1181 | 3-CN | 2 | 4,5-fused phenyl |
| 1182 | 4-CN | 2 | 4,5-fused phenyl |
| 1183 | 2-$CF_3$ | 2 | 4,5-fused phenyl |
| 1184 | 3-$CF_3$ | 2 | 4,5-fused phenyl |
| 1185 | 4-$CF_3$ | 2 | 4,5-fused phenyl |
| 1186 | H | 2 | 4,5-fused phenyl |
| 1187 | 2-$OCH_3$ | 2 | 4,5-fused phenyl |
| 1188 | 3-$OCH_3$ | 2 | 4,5-fused phenyl |
| 1189 | 4-$OCH_3$ | 2 | 4,5-fused phenyl |
| 1190 | 2-$CH_3$ | 2 | 4,5-fused phenyl |
| 1191 | 3-$CH_3$ | 2 | 4,5-fused phenyl |
| 1192 | 4-$CH_3$ | 2 | 4,5-fused phenyl |

In Examples 1093–1117, $R^5$ is taken with ring B when n=2 to from ring Q as follow:

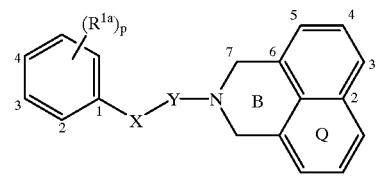

Utility

The compounds of this invention are useful as antagonsts for the treatment or prevention of CNS disorders such as anxiety, depression, sleep disorders, and schizophrenia.

Serotonin-7 (5-$HT_7$) Binding Assay

Serotonin-7 (5-$HT_7$) receptor binding was conducted using the method of Roth et al (1994). The cloned rat 5-$HT_7$ receptor was expressed in HEK-293 cells. An aliquot of frozen membranes was thawed and diluted with ice cold buffer containing 50 mM Tris, 10 mM $MgCl_2$, and 0.5 mM EDTA (pH 7.4 at 2° C.) to approximately 102 µg/ml. Binding of [$^3$H]-LSD to the 5-$HT_7$ receptor was initiated by the addition of 20.4 µg of membranes, 0.5 nM [$^3$H]-LSD, and concentrations of compounds ranging from $1\times10-5$ to $1\times10^{-11}$ M in total volume of 200 µl. Each concentration was run in duplicate. Nonspecific binding was defined by 100 mM unlabeled 5-HT.

After 60 minutes at 22° C., bound and free ligand were separated by rapid filtration through Packard glass fiber filters (presoaked in 0.2% PEI-polyethyline-amine) on a Tomtec harvester. Filters were air or oven dried and placed in a Packard Topcount for counting.

Inibition of the binding of the radiolabelled ligand was analyzed by using linear regression analysis of the logit transformation of the percent bound data. Inhibition constants ($K_i$) are the concentration of the inhibitors that inhibit binding by 50% divided by the sum of "one plus the quotient of the radioligand concentration" divided by "the affinity constant of the radioligand". The relationship between inhibition constant ($K_i$) and the concentration of inhibitor which causes 50 percent inhibition ($IC_{50}$) of an enzymatic reaction may be established by methods described by Cheng Y C and Prusoff W H., *Biochem. Pharrmacol.* 1973, 22, 3099–3108, and the binding of typical and atypical antipsychotic agents to 5-hydroxytryptamine-6 and 5-hydroxytryptamine-7 receptors is described in Roth B L, Craigo S C, Choudhary M S, Uluer A, Monsma F J Jr, Shen Y, Meltzer H Y and Sibley D R. in *J. Pharmacol Exp Ther.* 1994, 268, 1403–1410, the disclosures of which are both hereby incorporated by reference.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its alts and sodium EDTA. In addition, parenteral solutions an contain preservatives, such as benzalkonium chloride, ethyl- or propyl-paraben, and chlorobutanol. Suitable pharmaceutical carriers are described in *Remington's Pharmaceutical Sciences,* Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

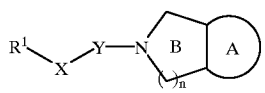

(I)

or a stereoisomer or pharmaceutically acceptable salt form thereof, wherein:

$R^1$ is selected from a $C_{6-10}$ carbocyclic aromatic residue substituted with 1–3 $R^{1a}$, and a 5–10 membered aromatic heterocyclic system containing from 1–4 heteroatoms selected from N, O, and S, substituted with 0–2 $R^{1a}$;

$R^1$ a is independently selected at each occurrence from halo, $-NO_2$, $-CN$, $-CF_3$ and $-CF_2CF_3$; X is selected from $-C(O)-$, $-CH(OH)-$, and $-CH(OC(O)CH_3)-$;

$R^4$ is selected from hydrogen and $C_{16}$ alkyl:

$R^4a$ is taken together with R1 to form a 5 or 6-membered fused heterocyclic ring containing 1–2 heteroatoms selected from O and N, substituted with 1 or 2 carbonyl groups;

Y is $C_{1-3}$ alkylene;

A is a 6 membered saturated or partially saturated ring fused with ring B, substituted with 0–3 $R^5$;

$R^5$ is selected from $C_{1-5}$ alkyl, halo and $-OCH_3$; and n is 2.

2. The compound of claim 1, wherein:

$R^1$ is phenyl substituted with 1–3 $R^{1a}$;

$R^{1a}$ is selected independently at each occurrence from halo, $-CN$, $-CF_3$ and $-CF_2CF_3$;

X is $-C(O)-$;

$R^{4a}$ is taken together when $R^1$ is phenyl to form a 5 membered fused cyclic urea;

Y is propylene; and

A is a 6 membered saturated or partially saturated ring fused with ring B, substituted with 0–3 $R^5$;

$R^5$ is selected independently at each occurrence from $C_{1-5}$ alkyl, halo and $-OCH_3$.

3. The compound of claim 2, wherein:

$R^1$ is phenyl substituted with 1–3 $R^{1a}$;

$R^{1a}$ is selected independently at each occurrence from para-halo and meta-fluoro;

X is $-C(O)-$;

Y is propylene; and

A is a 6 membered saturated or partially saturated ring fused with ring B, substituted with 0–2 $R^5$ $R^5$ is selected independently at each occurrence from $C_{1-5}$ alkyl, halo and $-OCH_3$.

4. The compound of claim 3, wherein:

$R^1$ is phenyl substituted with 1–3 $R^{1a}$;

$R^{1a}$ is meta-fluoro;

X is $-C(O)-$;

Y is propylene;

A is a 6 membered saturated or partially saturated ring fused with ring B, substituted with 0–2 $R^5$ $R^5$ is selected independently at each occurrence from $C_{1-5}$ alkyl, halo and $-OCH_3$.

5. A compound of selected from:

2-((4-(4-Fluorophenyl)-4-oxobutyl))-1,2,3,4-tetrahydroisoquinoline, 2-((4-(4-Pyridyl)-4-oxobutyl))-1,2,3,4-tetrahydroisoquinoline, 2-((4-(3-Fluorophenyl)-4-oxobutyl))-1,2,3,4-tetrahydroisoquinoline, 1,3-Dihydro-2-((4-(4-fluorophenyl)-4-oxobutyl))-1H-benz[de] isoquinoline, 2-((4-Oxo-4-(2-thienyl)butyl))-1,2,3,4-tetrahydroisoquinoline, 2-((3-(1,3-Dihydro-2H-benzimidazol-2-one)-1-ylpropyl))-1,2,3,4-tetrahydroisoquinoline, 2-(3-Phenylisoxazol-5-yl)methyl-1,2,3,4-tetrahydroisoquinoline, (+/−)-2-((3-(4-Fluorophenyl)-2-isoxazolin-5-yl)methyl-1,2,3,4-tetrahydroisoquinoline, 2-((3-(4-Fluorophenylthio)propyl))-1,2,3,4-tetrahydroisoquinoline, 2-((3-(4-Fluorophenyisulfonyl)propyl))-1,2,3,4-tetrahydro-isoquinoline 2-((3-(3-Fluorophenylthio)propyl))-1,2,3,4-tetrahydroisoquinoline 2-((3-(3-Fluorophenylsulfonyl)propyl))-1,2,3,4-tetrahydroisoquinoline 2-((4-(3-Pyridyl)-4-oxobutyl))-1,2,3,4-tetrahydro-isoquinoline, 2-((4-(4-Nitrophenyl)-4-oxobutyl))-1,2,3,4-tetrahydroisoquinoline, 2-((4-(3-Nitrophenyl)-4-oxobutyl))-1,2,3,4-tetrahydroisoquinoline, 2-((4-(3-Thienyl)-4-oxobutyi))-1,2,3,4-tetrahydro-isoquinoline, 2-((3-(4-FluorophenyIsulfonyl)propyl))-1,2,3,4-tetrahydro-isoquinoline, 2-((3-(4-Pyridylsulfonyl)propyl))-1,2,3,4-tetrahydroisoquinoline, 2-((3-(4-Nitrophenylsulfonyl)propyl))-1,2,3,4-tetrahydroisoquinoline, 2-((3-(3-Nitrophenylsulfonyl)propyl))-1,2,3,4-tetrahydroisoquinoline, 2-((3-(2-Thienylsulfonyl)propyl))-1,2,3,4-tetrahydroisoquinoline, and 2-((3-(3-Thienylsulfonyl)propyl))-1,2,3,4-tetrahydroisoquinoline.

6. A pharmaceutical composition, comprising a pharmaceutically acceptable carrier and a therapeutically effective amount of a compound according to claim 1 or a pharmaceutically acceptable salt thereof.

7. A method for treating or preventing a central nervous system disorder including sleep disorders, depression and schizophrenia, comprising administering to a patient in need thereof a therapeutically effective amount of a compound according to claim 1 or a pharmaceutically acceptable salt thereof.

8. A pharmaceutical composition, comprising a pharmaceutically acceptable carrier and a therapeutically effective amount of a compound according to claim 2 or a pharmaceutically acceptable salt thereof.

9. A pharmaceutical composition, comprising a pharmaceutically acceptable carrier and a therapeutically effective amount of a compound according to claim 3 or a pharmaceutically acceptable salt thereof.

10. A pharmaceutical composition, comprising a pharmaceutically acceptable carrier and a therapeutically effective amount of a compound according to claim 4 or a pharmaceutically acceptable salt thereof.

11. A pharmaceutical composition, comprising a pharmaceutically acceptable carrier and a therapeutically effective amount of a compound according to claim 5 or a pharmaceutically acceptable salt thereof.

12. A method for treating or preventing a central nervous system disorder including sleep disorders, depression and schizophrenia, comprising administering to a patient in need thereof a therapeutically effective amount of a compound according to claim 2 or a pharmaceutically acceptable salt thereof.

13. A method for treating or preventing a central nervous system disorder including sleep disorders, depression and schizophrenia, comprising administering to a patient in need thereof a therapeutically effective amount of a compound according to claim 3 or a pharmaceutically acceptable salt thereof.

14. A method for treating or preventing a central nervous system disorder including sleep disorders, depression and schizophrenia, comprising administering to a patient in need thereof a therapeutically effective amount of a compound according to claim 4 or a pharmaceutically acceptable salt thereof.

15. A method for treating or preventing a central nervous system disorder including sleep disorders, depression and schizophrenia, comprising admimistering to a patient in need thereof a therapeutically effective amount of a compound according to claim 5 or a pharmaceutically acceptable salt thereof.

* * * * *